(12) United States Patent
Chen et al.

(10) Patent No.: US 10,914,729 B2
(45) Date of Patent: Feb. 9, 2021

(54) METHODS FOR DETECTING PROTEIN BINDING SEQUENCES AND TAGGING NUCLEIC ACIDS

(71) Applicant: The Trustees of Princeton University, Princeton, NJ (US)

(72) Inventors: Kai Chen, Lawrenceville, NJ (US); Michael Levine, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 256 days.

(21) Appl. No.: 15/985,692

(22) Filed: May 21, 2018

(65) Prior Publication Data

US 2018/0335424 A1 Nov. 22, 2018

Related U.S. Application Data

(60) Provisional application No. 62/509,328, filed on May 22, 2017.

(51) Int. Cl.
| | |
|---|---|
| *G01N 33/53* | (2006.01) |
| *C12Q 1/68* | (2018.01) |
| *G01N 33/539* | (2006.01) |
| *G01N 33/566* | (2006.01) |
| *C12Q 1/6806* | (2018.01) |
| *C12Q 1/6869* | (2018.01) |
| *C12Q 1/6804* | (2018.01) |
| *C12N 9/12* | (2006.01) |

(52) U.S. Cl.
CPC ....... *G01N 33/5308* (2013.01); *C12Q 1/6804* (2013.01); *C12Q 1/6806* (2013.01); *C12Q 1/6869* (2013.01); *G01N 33/5306* (2013.01); *G01N 33/539* (2013.01); *G01N 33/566* (2013.01); *C12N 9/1241* (2013.01); *C12Y 207/07* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,409,818 A | 4/1995 | Davey et al. |
| 5,523,204 A | 6/1996 | Singer et al. |
| 5,536,649 A | 7/1996 | Fraiser et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,609 A | 1/1997 | Auerbach |
| 5,614,389 A | 3/1997 | Auerbach |
| 5,624,825 A | 4/1997 | Walker et al. |
| 5,625,126 A | 4/1997 | Lonberg et al. |
| 5,631,147 A | 5/1997 | Lohman et al. |
| 5,633,425 A | 5/1997 | Lonberg et al. |
| 5,635,400 A | 6/1997 | Brenner |
| 5,648,211 A | 7/1997 | Fraiser et al. |
| 5,661,016 A | 8/1997 | Lonberg et al. |
| 5,733,752 A | 3/1998 | Lohman et al. |
| 5,744,311 A | 4/1998 | Fraiser et al. |
| 5,756,702 A | 5/1998 | Lohman et al. |
| 5,773,733 A | 6/1998 | Tuan et al. |
| 5,786,183 A | 7/1998 | Ryder et al. |
| 5,834,202 A | 11/1998 | Auerbach |
| 5,849,547 A | 12/1998 | Cleuziat et al. |
| 5,874,260 A | 2/1999 | Cleuziat et al. |
| 5,916,779 A | 6/1999 | Pearson et al. |
| 5,981,179 A | 11/1999 | Lorincz et al. |
| 6,063,604 A | 5/2000 | Wick et al. |
| 6,087,133 A | 7/2000 | Dattagupta et al. |
| 6,124,120 A | 9/2000 | Lizardi |
| 6,159,736 A | 12/2000 | Reznikoff et al. |
| 6,214,587 B1 | 4/2001 | Dattagupta et al. |
| 6,218,151 B1 | 4/2001 | Cleuziat et al. |
| 6,238,868 B1 | 5/2001 | Carrino et al. |
| 6,251,639 B1 | 5/2001 | Kurn |
| 6,280,949 B1 | 8/2001 | Lizardi |
| 6,309,833 B1 | 10/2001 | Edman et al. |
| 6,326,173 B1 | 12/2001 | Edman et al. |
| 6,410,278 B1 | 6/2002 | Notomi et al. |
| 6,448,017 B1 | 9/2002 | Auerbach |
| 7,413,857 B2 | 8/2008 | Dahl et al. |
| 8,367,334 B2 | 2/2013 | Pugh et al. |
| 8,574,832 B2 | 11/2013 | Adli et al. |
| 9,080,211 B2 | 7/2015 | Grunenwald et al. |
| 2005/0153333 A1 | 7/2005 | Sooknanan |
| 2013/0203605 A1 | 8/2013 | Shendure et al. |

(Continued)

FOREIGN PATENT DOCUMENTS

| | | |
|---|---|---|
| EP | 0 799 897 A1 | 10/1997 |
| EP | 0 799 897 B1 | 10/1997 |

(Continued)

OTHER PUBLICATIONS

Adey, A. et al. (2010). "Rapid, Low-Input, Low-Bias Construction of Shotgun Fragment Libraries by High-Density in vitro Transposition," *Genome Biol.* 11:R119, 17 pages.

Al-Lazikani, B. et al. (Nov. 7, 1997) "Standard Conformations for the Canonical Structures of Immunoglobulins," *J. Mol. Biol.* 273(4):927-948.

Amini, S. et al. (Dec. 2014). "Haplotype-Resolved Whole Genome Sequencing by Contiguity Preserving Transposition and Combinatorial Indexing," *Nat. Genet.* 46(12):1343-1349, 21 pages.

(Continued)

*Primary Examiner* — James Martinell
(74) *Attorney, Agent, or Firm* — Morrison & Foerster LLP

(57) ABSTRACT

The present application provides a method of analyzing protein binding sequence, a method of making sequencing library, and compositions for performing such methods, which employs a transposome complex.

20 Claims, 11 Drawing Sheets

Specification includes a Sequence Listing.

(56) References Cited

U.S. PATENT DOCUMENTS

| | | | |
|---|---|---|---|
| 2015/0111788 A1 | 4/2015 | Fernandez et al. | |
| 2016/0208323 A1 | 7/2016 | Bernstein et al. | |

FOREIGN PATENT DOCUMENTS

| | | | |
|---|---|---|---|
| EP | 2 610 352 B1 | 10/2014 | |
| WO | WO-1991/10741 A1 | 7/1991 | |
| WO | WO-1995/23875 A1 | 9/1995 | |
| WO | WO-1996/33735 A1 | 10/1996 | |
| WO | WO-1996/34096 A1 | 10/1996 | |
| WO | WO-1998/24893 A2 | 6/1998 | |
| WO | WO-1998/24893 A3 | 6/1998 | |
| WO | WO-2000/28082 A1 | 5/2000 | |
| WO | WO-2000/56877 A1 | 9/2000 | |
| WO | WO-2002/16639 A1 | 2/2002 | |
| WO | WO-2013/078470 A2 | 5/2013 | |
| WO | WO-2013/078470 A3 | 5/2013 | |
| WO | WO-2014/189957 A2 | 11/2014 | |
| WO | WO-2014/189957 A3 | 11/2014 | |
| WO | WO-2014/190214 A1 | 11/2014 | |
| WO | WO-2014205296 A1 * | 12/2014 | |
| WO | WO-2016/019360 A1 | 2/2016 | |
| WO | WO-2017/025594 A1 | 2/2017 | |

OTHER PUBLICATIONS

Anderson, M.L.M. et al., (1985). "Quantitative Filter Hybridization," in *Chapter 4: Nucleic Acid Hybridization. A Practical Approach*, Hames, B.D. ed, IRL Press, Oxford, England, pp. 73-111.

Bernstein, B.E. et al. (Sep. 6, 2012). "An Integrated Encyclopedia of DNA Elements in the Human Genome," *Nature* 489:57-74.

Boehmer, P.E. et al. (Feb. 1993). "Herpes Simplex Virus Type 1 ICP8: Helix-Destabilizing Properties," *J. Virology* 67(2):711-715.

Boeke, J.D. et al. (1989). "Transcription and Reverse Transcription of Retrotransposons," *Annu. Rev. Microbiol.* 43:403-434.

Brenner, S. et al. (Feb. 15, 2000). "In vitro Cloning of Complex Mixtures of DNA on Microbeads: Physical Separation of Differentially Expressed cDNAs," *Proc. Natl. Acad. Sci. USA* 97(4):1665-1670.

Brown, P.O. et al. (Apr. 1989). "Retroviral Integration: Structure of the Initial Covalent Product and Its Precursor, and a Role for the Viral IN Protein," *Proc. Natl. Acad. Sci. USA* 86:2525-2529.

Brüggemann, M. et al. (1993). "Designer Mice: The Production of Human Antibody Repertoires in Transgenic Animals," *Year in Immunol.* 7:33-40.

Buenrostro J.D. et al. (Dec. 2013) "Transposition of Native Chromatin for Multimodal Regulatory Analysis and Personal Epigenomics," *Nat Methods.* 10(12):12130-1218, 15 pages.

Chothia, C. et al. (Dec. 5, 1985) "Domain Association in Immunoglobulin Molecules. The Packing of Variable Domains," *J. Mol. Biol.* 186(3):651-663.

Chothia, C. et al. (Aug. 20, 1987) "Canonical Structures for the Hypervariable Regions of Immunoglobulins," *J. Mol. Biol.* 196(4):901-917.

Chothia, C. et al. (Dec. 21-28, 1989) "Conformations of Immunoglobulin Hypervariable Regions," *Nature* 342(6252):877-883.

Clackson, T. et al. (Aug. 15, 1991). "Making Antibody Fragments Using Phage Display Libraries," *Nature* 352:624-628.

Colegio, O.R. et al. (Apr. 2001). "In Vitro Transposition System for Efficient Generation of Random Mutants of *Campylobacter jejuni*," *J. Bacteriol.* 183(7):2384-2388.

Craig, N.L. (Mar. 15, 1996). "V(D)J Recombination and Transposition: Closer Than Expected," *Science* 271(5255):1512.

Craig, N.L. (1996). "Transposon Tn7," Current Topic Microbiology Immunology Saedler, H. et al. eds., Springer-Verlag, Berlin, 204:27-48, 241 pages.

Cuthbert, G.L. et al. (Sep. 3, 2004). "Histone Deimination Antagonizes Arginine Methylation," *Cell* 118:545-553.

Devine, S.E. et al. (Sep. 11, 1994). "Efficient Integration of Artificial Transposons Into Plasmid Targets in vitro: A Useful Tool for DNA Mapping, Sequencing and Genetic Analysis," *Nucleic Acids Res.* 22(18):3765-3772.

Ernst, J. et al. (May 5, 2011). "Systematic Analysis of Chromatin State Dynamics in Nine Human Cell Types," *Nature* 473(7345):43-49.

Fellouse, F.A. et al. (2004). "Synthetic Antibodies From a Four-Amino-Acid Code: A Dominant Role for Tyrosine in Antigen Recognition," *Proc. Natl. Acad. Sci. USA* 101(34):12467-12472.

Fire, A. et al. (May 1995). "Rolling Replication of Short DNA Circles," *Proc. Natl. Acad. Sci. USA* 92:4641-4645.

Fishwild, D.M. et al. (Jul. 1996). "High-Avidity human IgGκ Monoclonal Antibodies From a Novel Strain of Minilocus Transgenic Mice," *Nature Biotechnol.* 14:845-851.

Gloor, G.B. (2004). "Gene Targeting in *Drosophila*," *Methods Mol. Biol.* 260:97-114.

Goryshin, I. et al. (Mar. 27, 1998). "Tn5 in Vitro Transposition," *J. Biol. Chem.* 273(13):7367-7374.

Greenleaf, W.J. (2015, e-pub. Oct. 22, 2014). "Assaying the Epigenome in Limited Number of Cells," *Methods* 72:51-56.

Hammerling et al. (1981). "Production of Antibody-Producing Hybridomas in The Rodent Systems," in *Monoclonal Antibodies and T-Cell Hybridomas* pp. 563-587.

Harlow, E. et al. (1988). *Antibodies, A Laboratory Manual*, Cold Spring Harbor Publications, New York, 89 pages.

Hassa, P.O. et al. (Sep. 2006). "Nuclear ADP-Ribosylation Reactions in Mammalian Cells: Where Are We Today and Where Are We Going?" *Microbiol. Mol. Biol. Rev.* 70(3):789-829.

He, Q. et al. (Apr. 2015, e-pub Mar. 9, 2015). "ChIP-Nexus: A Novel ChIP-Exo Protocol for Improved Detection of in vivo Transcription Factor Binding Footprints," *Nat Biotechnol.* 33(4):395-401.

Helgason, C.D. et al. (2005) "Basic Cell Culture Protocols $3^{rd}$ Edition," in *Methods in Molecular Biology*, 365 pages.

Hongo, J.S. et al. (Jun. 1995). "Development and Characterization of Murine Monoclonal Antibodies to the Latency-Associated Peptide of Transforming Growth Factor $β_1$," *Hybridoma* 14(3):253-260.

Ichikawa, H. et al. (Nov. 5, 1990). "In Vitro Transposition of Transposon Tn3," *J. Biol. Chem.* 265(31):18829-18832.

Jakobovits, A. et al. (Mar. 1993). "Analysis of Homozygous Mutant, Chimeric Mice: Deletion of the Immunoglobulin Heavy-Chain Joining Region Blocks B-Cell Development and Antibody Production," *Proc. Natl. Acad. Sci. USA* 90:2551-2555.

Jakobovits, A. et al. (Mar. 18, 1993). "Germ-Line Transmission and Expression of a Human-Derived Yeast Artificial Chromosome," *Nature* 362:255-258.

Jenuwein, T. et al. (Aug. 10, 2001). "Translating the Histone Code," *Science* 293(5532):1074-1080.

Kirby C. et al. (2002). "Cryptic Plasmids of *Mycobacterium avium*: Tn 552 to the Rescue," *Mol. Microbiol.* 43(1):173-186.

Kleckner, N. et al. (1996). "Tn10 and IS10 Transposition and Chromosome Rearrangements: Mechanism and Regulation In Vivo and In Vitro," *Curr. Top Microbiol. Immunol.* 204:49-82.

Kobza, K.A. et al. (2005). "K4, K9 and K18 in Human Histone H3 Are Targets for Biotinylation by Biotinidase," *FEBS J.* 272(16):4249-4259.

Köhler, G. et al. (Aug. 7, 1975). "Continuous Cultures of Fused Cells Secreting Antibody of Predefined Specificity," *Nature* 256:495-497.

Kong, H. et al. (Jan. 25, 1993). "Characterization of a DNA Polymerase From the Hyperthermophile Archea *Thermococcus litoralis*," *J. Biol. Chem.* 268(3):1965-1975.

König, J. et al. (Jul. 2010, e-pub Jul. 4, 2010) "iCLIP Reveals the Function of hnRNP Particles in Splicing At Individual Nucleotide Resolution," *Nat Struct Mol Biol.* 17(7):909-915.

Kuzmichev, A. et al. (Apr. 23, 2004). "Different EZh2-Containing Complexes Target Methylation of Histone H1 or Nucleosomal Histone H3," *Mol. Cell* 14:183-193.

Lampe, D.J. et al. (1996). "A Purified mariner Transposase Is Sufficient to Mediate Transposition in vitro," *EMBO J.* 15(19):5470-5479.

Lee, C.V. et al. (2004). "High-affinity Human Antibodies from Phage-displayed Synthetic Fab Libraries with a Single Framework Scaffold," *J. Mol. Biol.* 340(5):1073-1093.

Lee, C.V. et al. (2004). "Bivalent Antibody Phage Display Mimics Natural Immunoglobulin," *J. Immunol. Methods* 284(1-2):119-132.

(56) References Cited

OTHER PUBLICATIONS

Lonberg, N. et al. (Apr. 28, 1994). "Antigen-Specific Human Antibodies From Mice Comprising Four Distinct Genetics Modifications," *Nature* 368:856-859.
Lonberg, N. et al. (1995). "Human Antibodies From Transgenic Mice," *Intern. Rev. Immunol.* 13:65-93.
Marks, J.D. et al. (1991). "By-Passing Immunization: Human Antibodies From V-Gene Libraries Displayed on Phage," *J. Mol. Biol.* 222:581-597.
Marks, J.D. et al. (Jul. 1992). "By-Passing Immunization: Building High Affinity Human Antibodies by Chain Shuffling," *Bio/Technology* 10:779-783.
Martin, C. et al. (Nov. 2005). "The Diverse Functions of Histone Lysine Methylation," *Nat. Rev. Mol. Cell Biol.* 6:838-849.
Mizuuchi, K. (Dec. 1983). "In Vitro Transposition of Bacteriophage Mu: A Biochemical Approach to a Novel Replication Reaction," *Cell* 35(3 pt 2):785-794, 2 pages. Abstract Only.
Morrison, S.L. (Apr. 28, 1994). "Success in Specification," *Nature* 368:812-813.
Nathan, D. et al. (Sep. 8, 2006). "Histone Sumoylation Is a Negative Regulator in *Saccharomyces cerevisiae* and Shows Dynamic Interplay With Positive-Acting Histone Modifications," *Genes Dev.* 20:966-976.
Nelson, C.J. et al. (Sep. 8, 2006). "Proline Isomerization of Histone H3 Regulates Lysine Methylation and Gene Expression," *Cell* 126:905-916.
Neuberger, M. (Jul. 1996). "Generating High-Avidity Human Mabs in Mice," *Nature Biotechnol.* 14:826.
NEXTERA™ DNA Sample Prep Kit (Illumina®-Compatible), Epicentre® Biotechnologies, retrieved from <http://www.epibio.com/nextera/Nextera™ DNA Sample Prep Kit (Illumina®-Compatible).pdf>, lasted visited Dec. 27, 2018, 9 pages.
Nowak, S.J. et al. (Apr. 2004). "Phosphorylation of histone H3: A Balancing Act Between Chromosome Condensation and Transcriptional Activation," *Trends Genet.* 20(4):214-220.
Ohtsubo, F. et al. (1996). "Bacterial Insertion Sequences," *Curr. Top. Microbiol. Immunol.* 204:1-26.
Plasterk, R.H. (1996). "The Tc1/mariner Transposon Family," *Curr. Top Microbiol. Immunol.* 204:125-143.
Rigler, M.N. et al. (Apr. 14, 1995). "Differences in the Mechanism of Stimulation of T7 DNA Polymerase by Two Binding Modes of *Escherichia coli* Single-Stranded DNA-Binding Protein," *J. Biol. Chem.* 270(15):8910-8919.
Savilahti, H. et al. (1995). "The Phage Mu Transpososome Core: DNA Requirements for Assembly and Function," *EMBO J.* 14(19):4893-4903.
Shilatifard, A. (2006, e-pub. Feb. 22, 2006)."Chromatin Modifications by Methylation and Ubiquitination: Implications in the Regulation of Gene Expression," *Annu. Rev. Biochem.* 75:243-269.
Shoemaker, D.D. et al. (Dec. 1996). "Quantitative Phenotypic Analysis of Yeast Deletion Mutants Using a Highly Parallel Molecular Bar-Coding Strategy," *Nature Genetics* 14:450-456.
Sidhu, S.S. et al. (2004). "Phage-Displayed Antibody Libraries of Synthetic Heavy Chain Complementarity Determining Regions," *J. Mol. Biol.* 338(2): 299-310.
Siegal G. et al. (Jul. 5, 1992). "A Novel DNA Helicase From Calf Thymus," *J. Biol. Chem.* 267(19):13629-13635.
Skaliter, R. et al. (Oct. 1994). "Rolling Circle DNA Replication In Vitro by a Complex of Herpes Simplex Virus Type 1-Encoded Enzymes," *Proc. Natl. Acad. Sci. USA* 91:10665-10669.
Sterner, D.E. et al. (Jun. 2000). "Acetylation of Histones and Transcription-Related Factors," *Microbiol. Mol. Biol. Rev.* 64(2):435-459.
Strahl, B.D. et al. (Jan. 6, 2000). "The Language of Covalent Histone Modifications," *Nature* 403(6765):41-45.
*Thermo Scientific Pierce Cell Lysis Technical Handbook Version 2.* (2012). Thermo Scientific Part, 54 pages.
Tsurumi, T. et al. (Dec. 1993). "Functional Interaction between Epstein-Barr Virus DNA Polymerase Catalytic Subunit and Its Accessory Subunit In Vitro," *J. Virology* 67(12):7648-7653.
Van Opijnen, T et al. (Jul. 2013, e-pub May 28, 2013) "Transposon Insertion Sequencing: A New Tool for Systems-Level Analysis of Microorganisms," *Nat Rev Microbiol.* 11(7):435-442, 18 pages.
Wang, Y. et al. (Oct. 8, 2004). "Human PAD4 Regulates Histone Arginine Methylation Levels via Demethylimination," *Science* 306:279-283.
Yeh. H.E. et al. (Nov. 2013). "Targeting Transcription Factors: Promising New Strategies for Cancer Therapy," *Curr. Opin. Oncol.* 25(6):652-658.
Zhang, Y. et al. (2001). "Transcription Regulation by Histone Methylation: Interplay Between Different Covalent Modifications of the Core Histone Tails," *Genes Dev.* 15:2343-2360.
Zijderveld, D.C. et al. (Feb. 1994). "Helix-Destabilizing Properties of the Adenovirus DNA-Binding Protein," *J. Virology* 68(2):1158-1164.

* cited by examiner

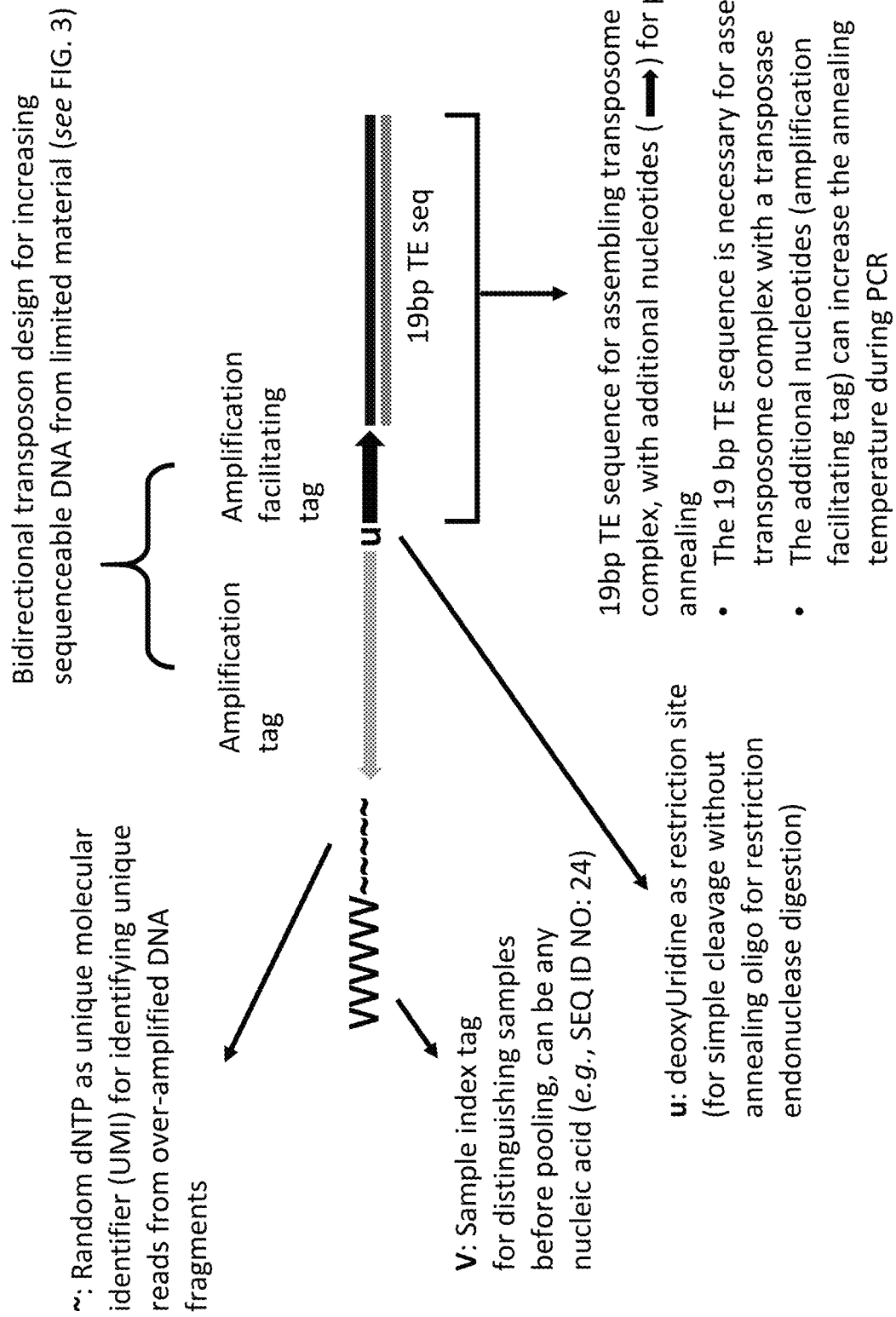
FIG. 1 Transposon end composition design

FIG. 2 Exemplary workflow of ChIP-SMITH

Step 1: mildly crosslink samples, briefly shear chromatin by sonication

Step 2: individually tagment different biological samples with transposon end compositions comprising different sample index tags

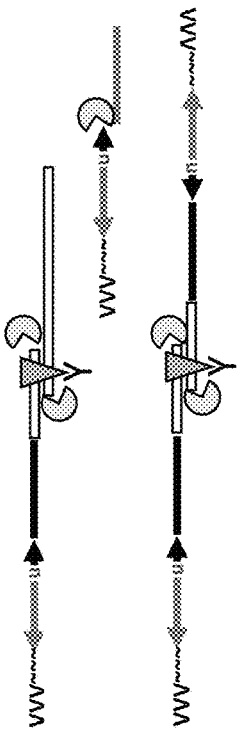

Step 3: pool differentially indexed samples and perform ChIP (ChIPed DNA captured on beads)

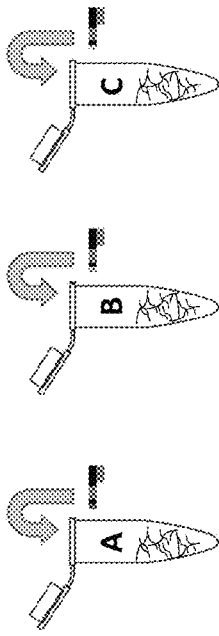

Step 4: digesting ChIPed chromatin with Exo III at 3' end

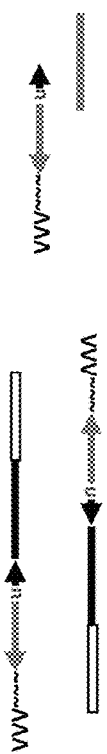

Step 5: quick reverse-crosslink and denature at 95°C for 60 min

Step 6: self-circularize with CircLigase

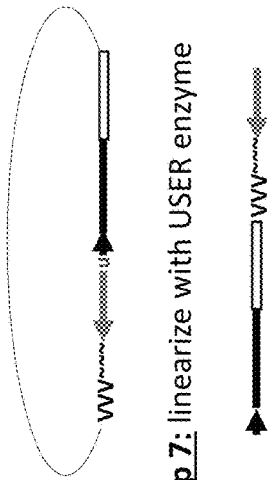

Step 7: linearize with USER enzyme

Step 8: DNA clean up, PCR using primers comprising sequencing barcode (experimental index)

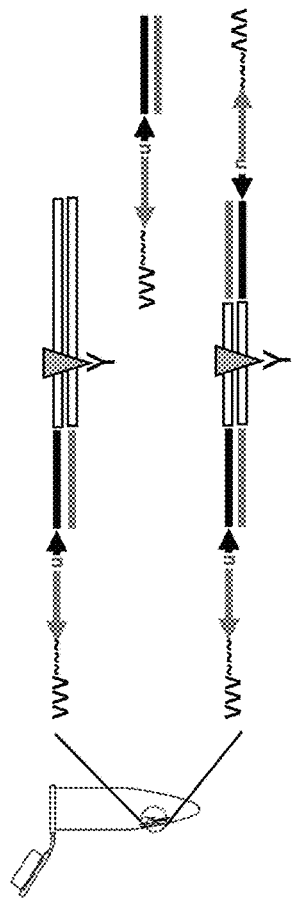

Y: antibody against X
▽: protein X of interest (*e.g.*, transcription factor X)
◯: Exo III
V: sample index tag

FIG. 3 Advantages of bidirectional transposon design of the transposon end composition
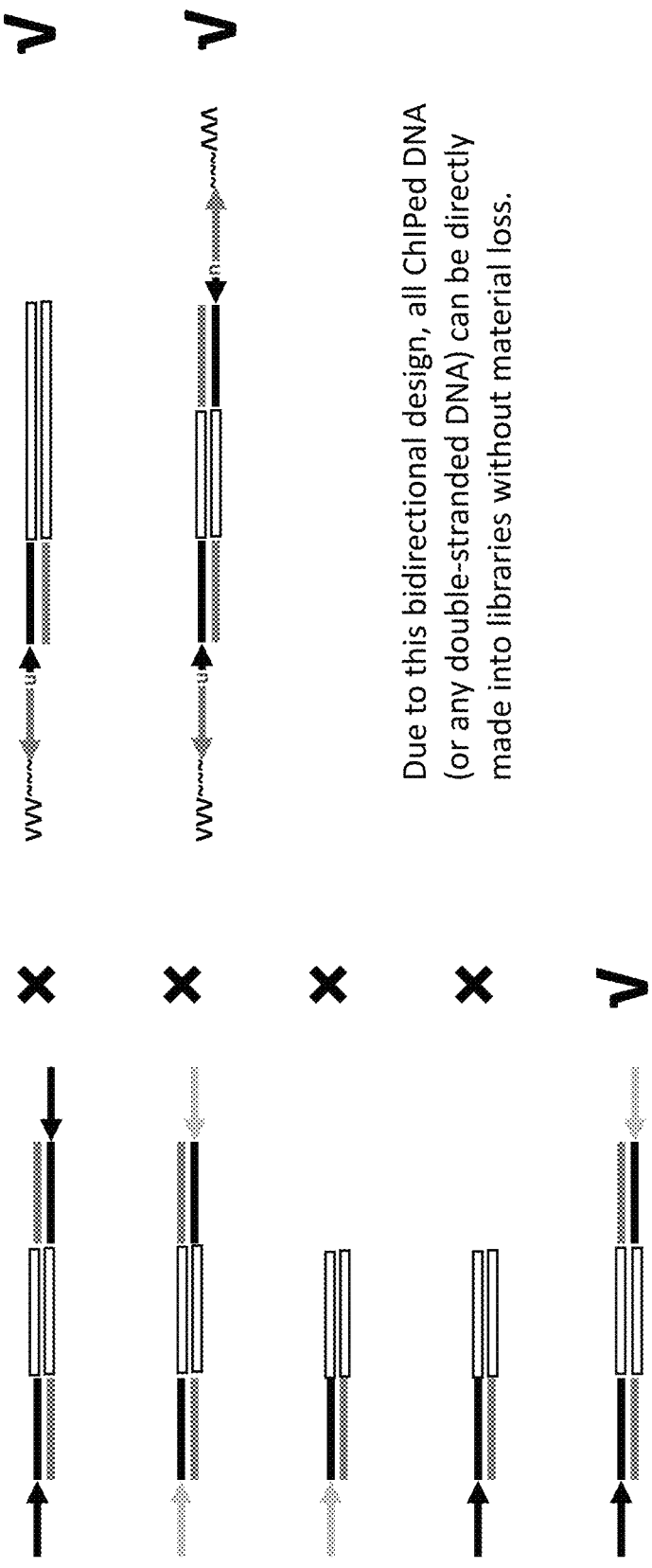

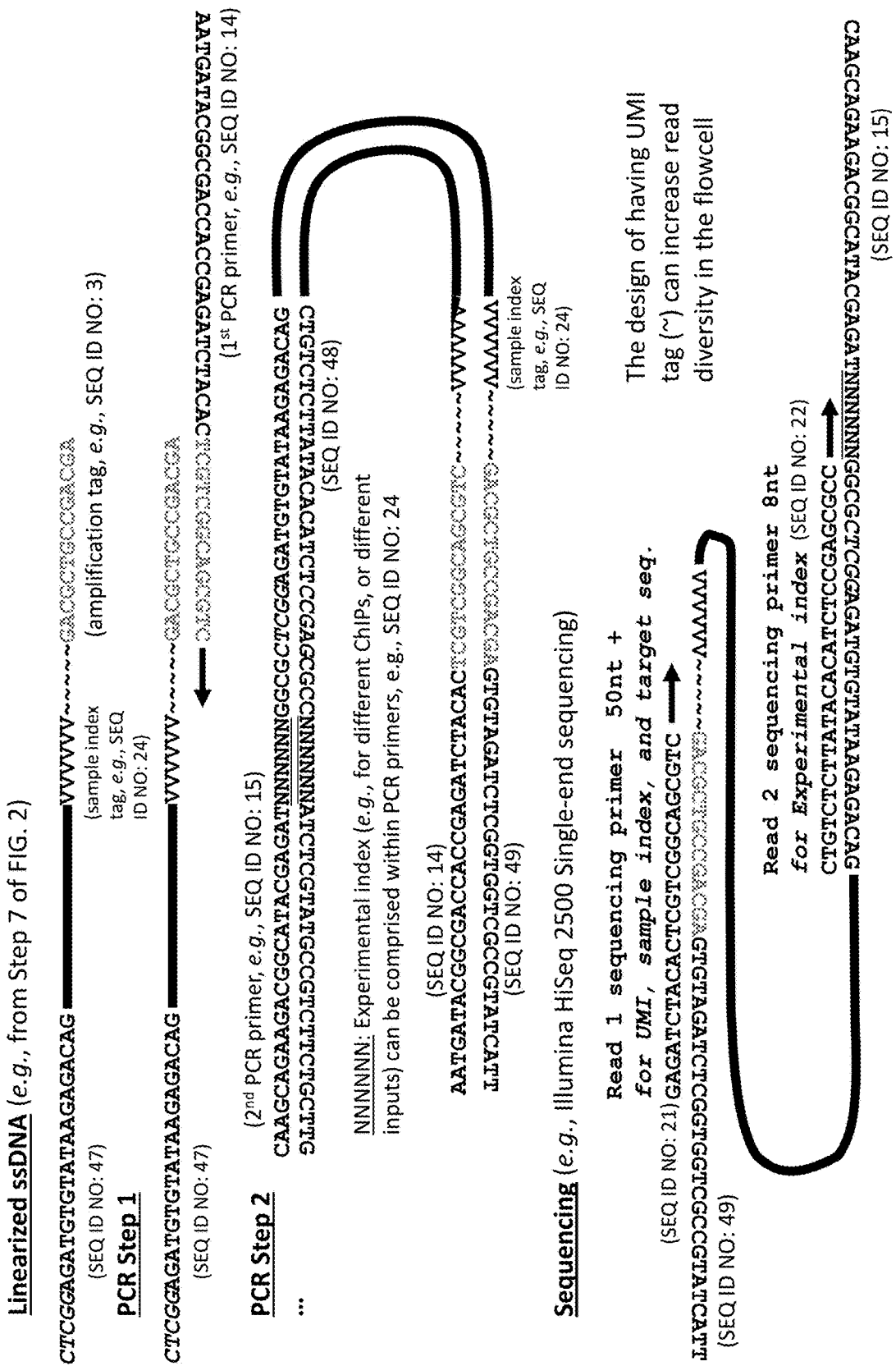
FIG. 4 Exemplary workflow of ChIP-SMITH library preparation and sequencing

FIG. 5 The effect of transposon end composition oligonucleotide length on Tn5 activity
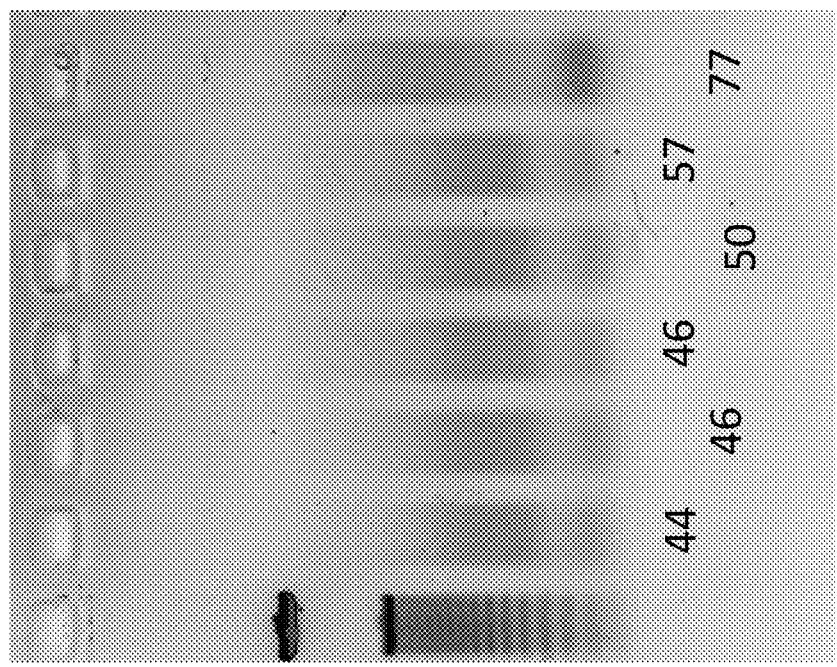
With the same Molar concentration of transposon end composition oligos: the longer the oligos, the more free oligos are left unassembled, and the bigger the size of tagmented DNA. The ideal oligo size for assembling Tn5 should be less than about 50 nt.

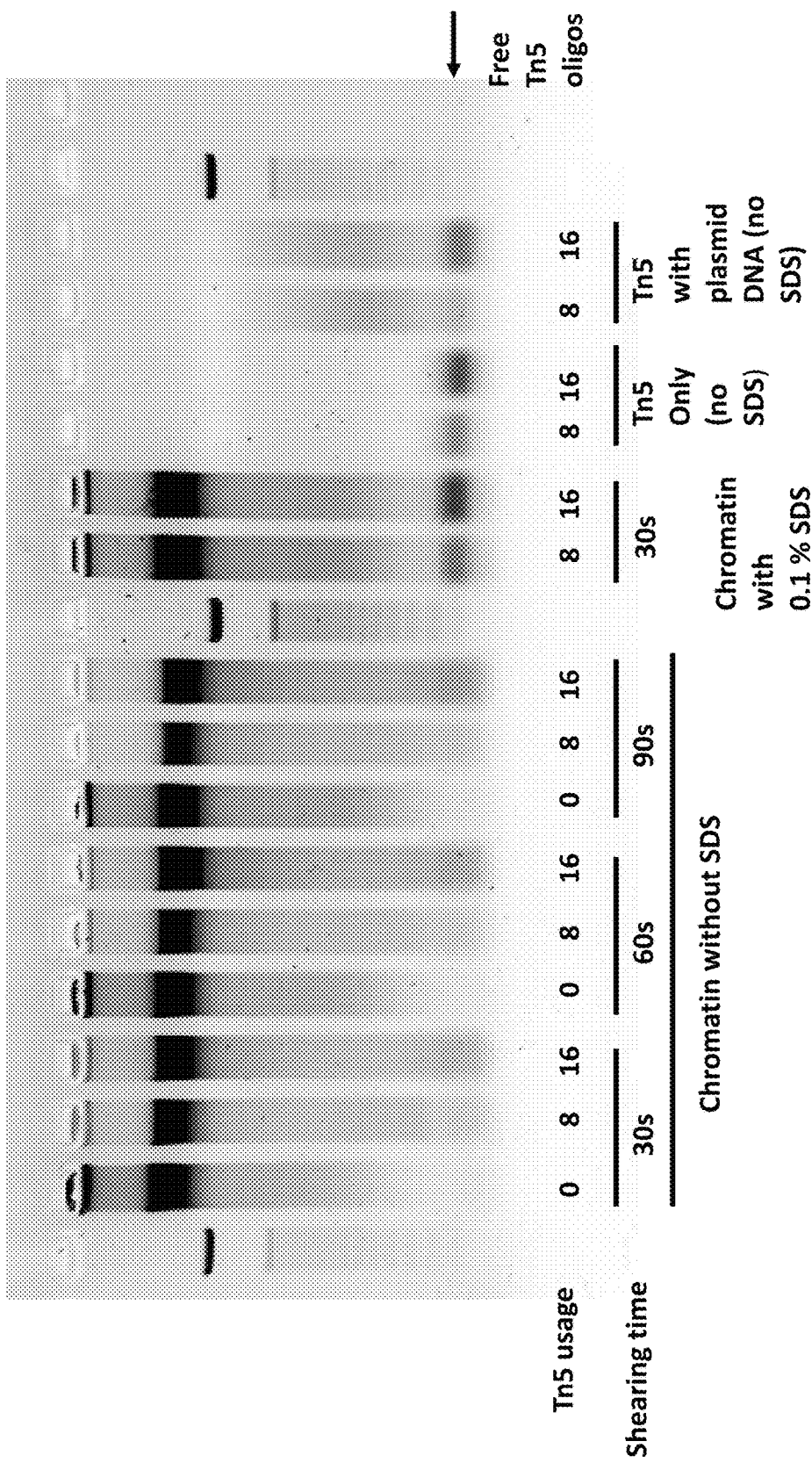
FIG. 6A Tn5 can incorporate transposon end compositions into cross-linked chromatin with little SDS

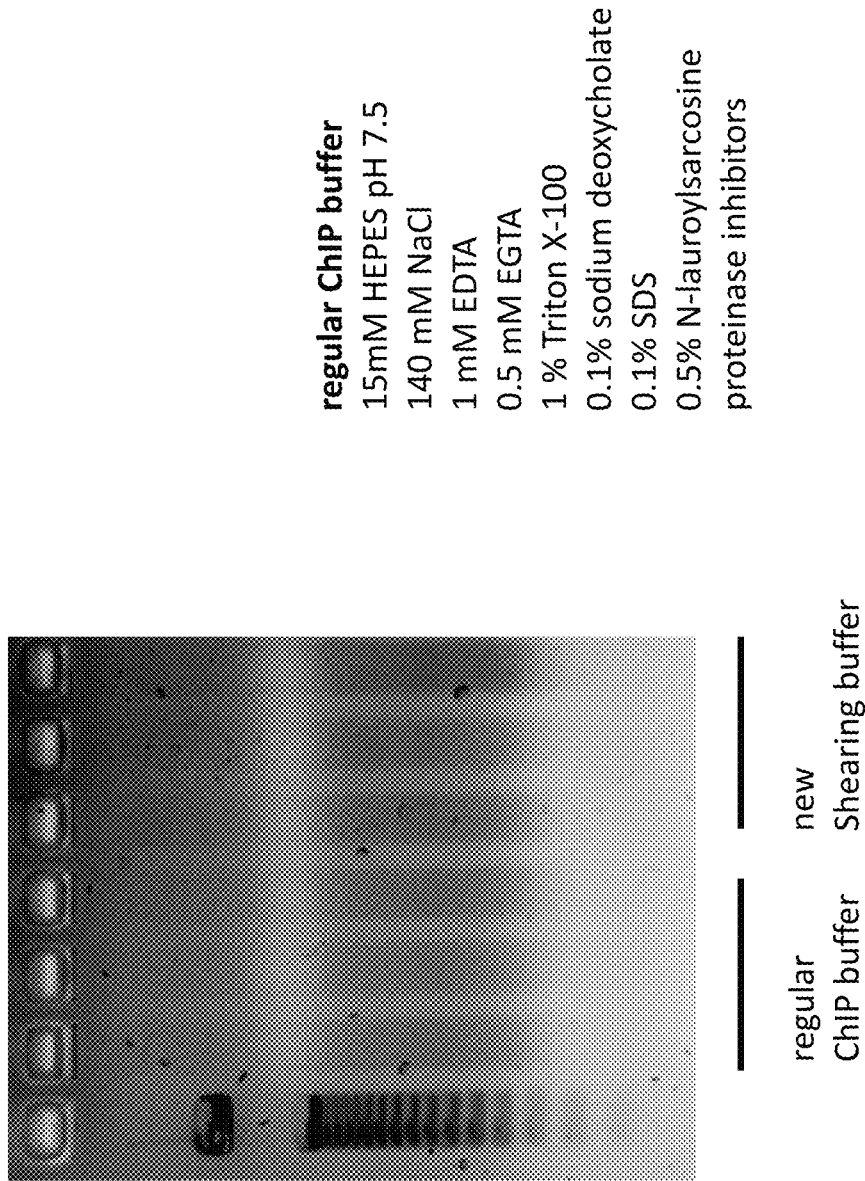

FIG. 6B Comparison between a successful shearing by sonication with regular ChIP buffer with detergents and sonication with new Shearing buffer for Tn5 regular ChIP buffer
15mM HEPES pH 7.5
140 mM NaCl
1 mM EDTA
0.5 mM EGTA
1 % Triton X-100
0.1% sodium deoxycholate
0.1% SDS
0.5% N-lauroylsarcosine
proteinase inhibitors regular ChIP buffer          new Shearing buffer Chromatin in either regular ChIP buffer or undiluted Shearing buffer was sheared with Branson® Sonicator at output 20% for 80 seconds

FIG. 7 The effect of different detergents on Tn5 activity

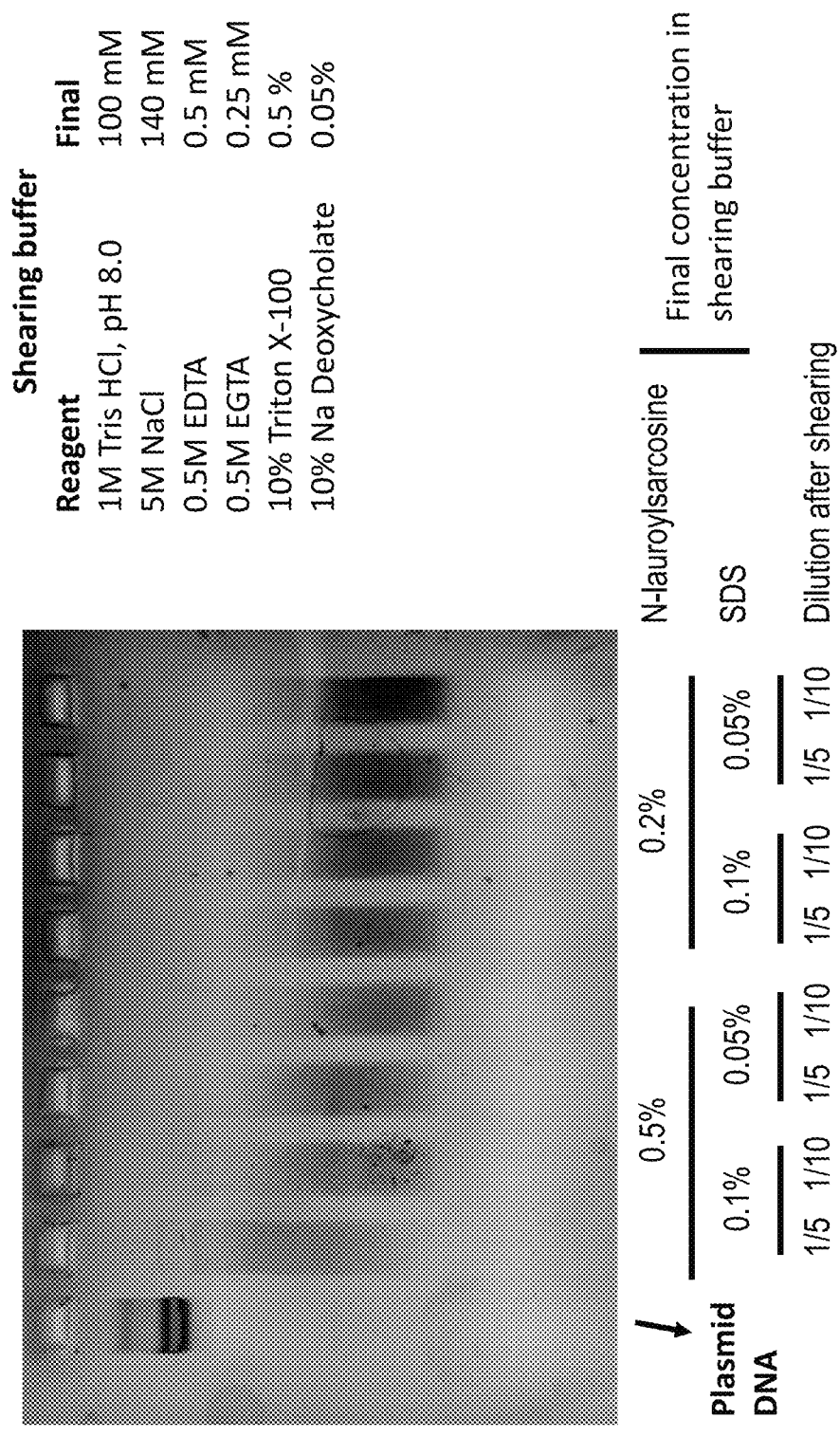
FIG. 8 Dilution with new shearing buffer after shearing can protect Tn5 activity without affecting shearing efficiency

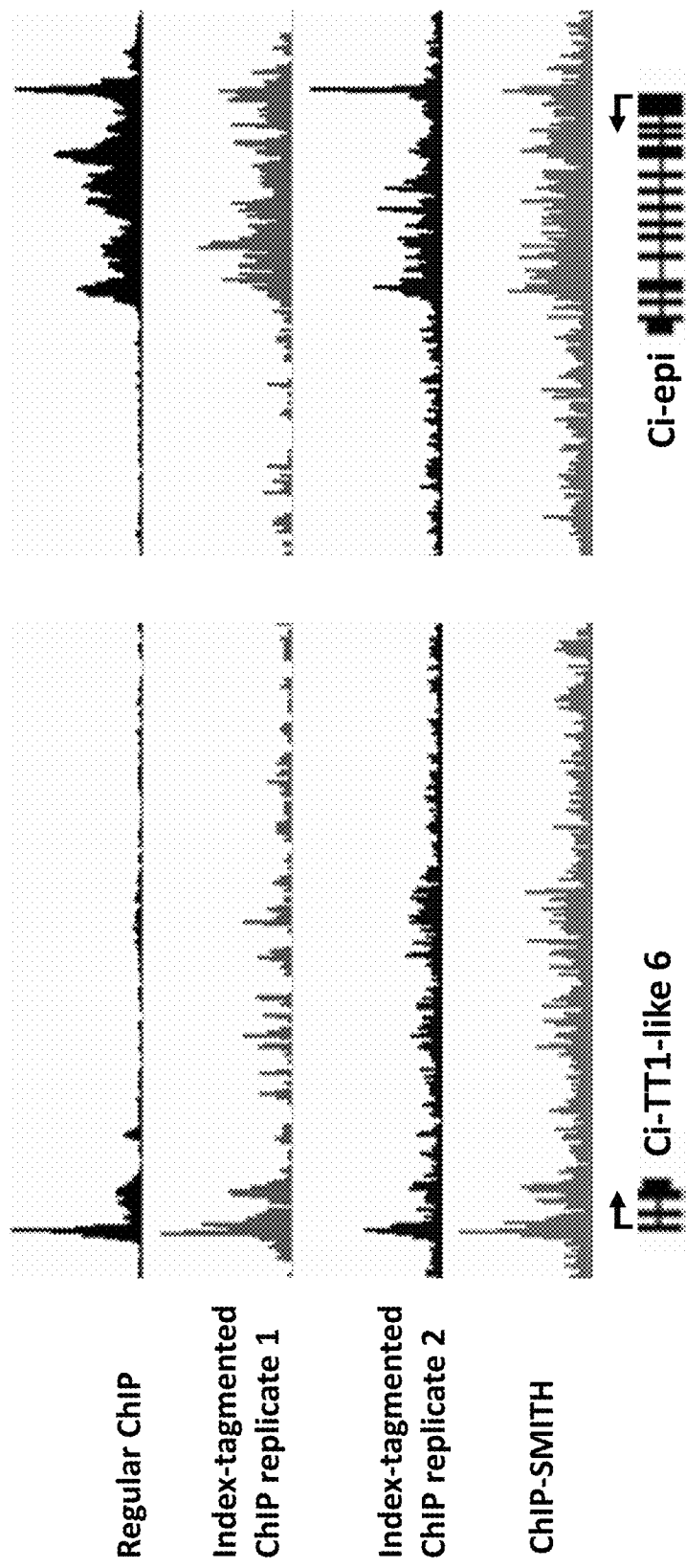
FIG. 9 Snapshot showing comparison between ChIP-SMITH and regular ChIP protocols using antibodies against RNA polymerase II

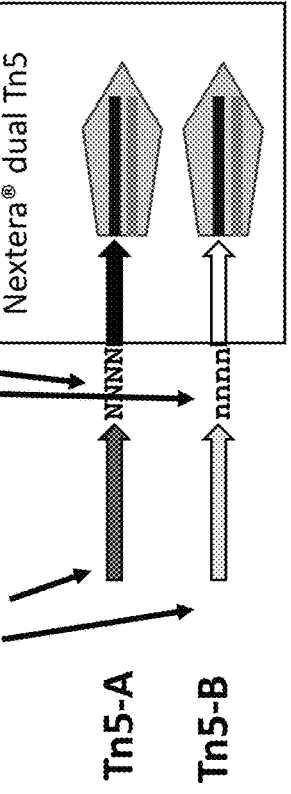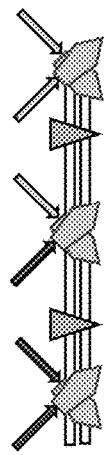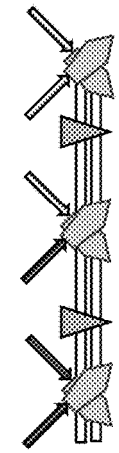

FIG. 10 Exemplary workflow of index-tagmented ChIP with modified Nextera® dual-transposon design

Combination of two different Tn5 (A/B)

Tn5-A / Tn5-B: connector sequence for NEBNext® Multiplex Oligos, Sample barcode, Nextera® dual Tn5

Step 1: mildly crosslink samples, briefly shear chromatin by sonication

Step 2: individually tagment different biological samples with transposon end compositions comprising different sample index tags Step 3: pool differentially indexed samples and perform ChIP (ChIPed DNA captured on beads)

▽ : Tn5 protein
Y: antibody against X
▽ : protein X of interest (e.g., transcription factor X)

Step 4: slow reverse-crosslink at 65°C for > 6 hour

Step 5: Directly PCR with primers annealing to different connector sequences A/B, only sample DNA tagged with different oligos on both ends can be amplified.

SEQUENCE LISTING

<160> NUMBER OF SEQ ID NOS: 49

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
agatgtgtat aagagacag                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
ctgtctctta tacacatct                                                19

<210> SEQ ID NO 3
<211> LENGTH: 14
<212> TYPE: DNA
<213> ORGANISM: Artificial Sequence
<220> FEATURE:
<223> OTHER INFORMATION: Synthetic Construct

<400> SEQUENCE: 3
gacgctgccg acga                                                     14

<210> SEQ ID NO 4
<211> LENGTH: 5
<212> TYPE: DNA
<213> ORGANISM: Artificial Sequence
<220> FEATURE:
<223> OTHER INFORMATION: Synthetic Construct

<400> SEQUENCE: 4 ctcgg                                                                5

<210> SEQ ID NO 5
<211> LENGTH: 50

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 5
nnnnnnnnnn ngacgctgcc gacganctcg gagatgtgta taagagacag          50

<210> SEQ ID NO 6
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 6
atgtcannnn ngacgctgcc gacganctcg gagatgtgta taagagacag          50

<210> SEQ ID NO 7
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 7
agacgtnnnn ngacgctgcc gacganctcg gagatgtgta taagagacag          50

<210> SEQ ID NO 8
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 8
tcagtannnn ngacgctgcc gacganctcg gagatgtgta taagagacag          50

<210> SEQ ID NO 9
```

```
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 9
tatcatnnnn ngacgctgcc gacganctcg gagatgtgta taagagacag          50

<210> SEQ ID NO 10
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 10
gacgtcnnnn ngacgctgcc gacganctcg gagatgtgta taagagacag          50

<210> SEQ ID NO 11
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 11
gcacgcnnnn ngacgctgcc gacganctcg gagatgtgta taagagacag          50

<210> SEQ ID NO 12
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 12
cagtagnnnn ngacgctgcc gacganctcg gagatgtgta taagagacag          50
```

```
<210> SEQ ID NO 13
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 10, 11
<223> OTHER INFORMATION: n = A,T,C or G
<220> FEATURE:
<221> NAME/KEY: misc_feature
<222> LOCATION: 26
<223> OTHER INFORMATION: n = deoxyUridine

<400> SEQUENCE: 13
cgtctgnnnn ngacgctgcc gacganctcg gagatgtgta taagagacag        50

<210> SEQ ID NO 14
<211> LENGTH: 43
<212> TYPE: DNA
<213> ORGANISM: Artificial Sequence
<220> FEATURE:
<223> OTHER INFORMATION: Synthetic Construct

<400> SEQUENCE: 14
aatgatacgg cgaccaccga gatctacact cgtcggcagc gtc               43

<210> SEQ ID NO 15
<211> LENGTH: 58
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 25, 26, 27, 28, 29, 30
<223> OTHER INFORMATION: n = A,T,C or G

<400> SEQUENCE: 15
caagcagaag acggcatacg agatnnnnnn ggcgctcgga gatgtgtata agagacag    58

<210> SEQ ID NO 16
<211> LENGTH: 58
<212> TYPE: DNA
<213> ORGANISM: Artificial Sequence
<220> FEATURE:
<223> OTHER INFORMATION: Synthetic Construct

<400> SEQUENCE: 16
caagcagaag acggcatacg agatcgtgat ggcgctcgga gatgtgtata agagacag    58

<210> SEQ ID NO 17
<211> LENGTH: 58
<212> TYPE: DNA
<213> ORGANISM: Artificial Sequence
<220> FEATURE:
<223> OTHER INFORMATION: Synthetic Construct

<400> SEQUENCE: 17
caagcagaag acggcatacg agatacatcg ggcgctcgga gatgtgtata agagacag    58

<210> SEQ ID NO 18
<211> LENGTH: 58
<212> TYPE: DNA
<213> ORGANISM: Artificial Sequence
<220> FEATURE:
<223> OTHER INFORMATION: Synthetic Construct
```

<400> SEQUENCE: 18
caagcagaag acggcatacg agatgccaat ggcgctcgga gatgtgtata agagacag    58

<210> SEQ ID NO 19
<211> LENGTH: 58
<212> TYPE: DNA
<213> ORGANISM: Artificial Sequence
<220> FEATURE:
<223> OTHER INFORMATION: Synthetic Construct

<400> SEQUENCE: 19
caagcagaag acggcatacg agatgatcag ggcgctcgga gatgtgtata agagacag    58

<210> SEQ ID NO 20
<211> LENGTH: 58
<212> TYPE: DNA
<213> ORGANISM: Artificial Sequence
<220> FEATURE:
<223> OTHER INFORMATION: Synthetic Construct

<400> SEQUENCE: 20
caagcagaag acggcatacg agatcagatc ggcgctcgga gatgtgtata agagacag    58

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
gagatctaca ctcgtcggca gcgtc                                        25

<210> SEQ ID NO 22
<211> LENGTH: 28
<212> TYPE: DNA
<213> ORGANISM: Artificial Sequence
<220> FEATURE:
<223> OTHER INFORMATION: Synthetic Construct

<400> SEQUENCE: 22
ctgtctctta tacacatctc cgagcgcc                                     28

<210> SEQ ID NO 23
<211> LENGTH: 28
<212> TYPE: DNA
<213> ORGANISM: Artificial Sequence
<220> FEATURE:
<223> OTHER INFORMATION: Synthetic Construct

<400> SEQUENCE: 23
ggcgctcgga gatgtgtata agagacag                                     28

<210> SEQ ID NO 24
<211> LENGTH: 6
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 24 nnnnnn                                                             6

```
<210> SEQ ID NO 25
<211> LENGTH: 6
<212> TYPE: DNA
<213> ORGANISM: Artificial Sequence
<220> FEATURE:
<223> OTHER INFORMATION: Synthetic Construct

<400> SEQUENCE: 25 atgtca                                                                     6

<210> SEQ ID NO 26
<211> LENGTH: 6
<212> TYPE: DNA
<213> ORGANISM: Artificial Sequence
<220> FEATURE:
<223> OTHER INFORMATION: Synthetic Construct

<400> SEQUENCE: 26 agacgt                                                                     6

<210> SEQ ID NO 27
<211> LENGTH: 6
<212> TYPE: DNA
<213> ORGANISM: Artificial Sequence
<220> FEATURE:
<223> OTHER INFORMATION: Synthetic Construct

<400> SEQUENCE: 27 tcagta                                                                     6

<210> SEQ ID NO 28
<211> LENGTH: 6
<212> TYPE: DNA
<213> ORGANISM: Artificial Sequence
<220> FEATURE:
<223> OTHER INFORMATION: Synthetic Construct

<400> SEQUENCE: 28 tatcat                                                                     6

<210> SEQ ID NO 29
<211> LENGTH: 6
<212> TYPE: DNA
<213> ORGANISM: Artificial Sequence
<220> FEATURE:
<223> OTHER INFORMATION: Synthetic Construct

<400> SEQUENCE: 29 gacgtc                                                                     6

<210> SEQ ID NO 30
<211> LENGTH: 6
<212> TYPE: DNA
<213> ORGANISM: Artificial Sequence
<220> FEATURE:
<223> OTHER INFORMATION: Synthetic Construct

<400> SEQUENCE: 30 gcacgc                                                                     6

<210> SEQ ID NO 31
<211> LENGTH: 6
<212> TYPE: DNA
<213> ORGANISM: Artificial Sequence
<220> FEATURE:
```

```
<223> OTHER INFORMATION: Synthetic Construct

<400> SEQUENCE: 31 cagtag                                                                    6

<210> SEQ ID NO 32
<211> LENGTH: 6
<212> TYPE: DNA
<213> ORGANISM: Artificial Sequence
<220> FEATURE:
<223> OTHER INFORMATION: Synthetic Construct

<400> SEQUENCE: 32 cgtctg                                                                    6

<210> SEQ ID NO 33
<211> LENGTH: 6
<212> TYPE: DNA
<213> ORGANISM: Artificial Sequence
<220> FEATURE:
<223> OTHER INFORMATION: Synthetic Construct

<400> SEQUENCE: 33 cgtgat                                                                    6

<210> SEQ ID NO 34
<211> LENGTH: 6
<212> TYPE: DNA
<213> ORGANISM: Artificial Sequence
<220> FEATURE:
<223> OTHER INFORMATION: Synthetic Construct

<400> SEQUENCE: 34 acatcg                                                                    6

<210> SEQ ID NO 35
<211> LENGTH: 6
<212> TYPE: DNA
<213> ORGANISM: Artificial Sequence
<220> FEATURE:
<223> OTHER INFORMATION: Synthetic Construct

<400> SEQUENCE: 35 gccaat                                                                    6

<210> SEQ ID NO 36
<211> LENGTH: 6
<212> TYPE: DNA
<213> ORGANISM: Artificial Sequence
<220> FEATURE:
<223> OTHER INFORMATION: Synthetic Construct

<400> SEQUENCE: 36 gatcag                                                                    6

<210> SEQ ID NO 37
<211> LENGTH: 6
<212> TYPE: DNA
<213> ORGANISM: Artificial Sequence
<220> FEATURE:
<223> OTHER INFORMATION: Synthetic Construct

<400> SEQUENCE: 37 cagatc                                                                    6
```

```
<210> SEQ ID NO 38
<211> LENGTH: 5
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5
<223> OTHER INFORMATION: n = A,T,C or G

<400> SEQUENCE: 38 nnnnn                                                                       5

<210> SEQ ID NO 39
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20, 21, 22
<223> OTHER INFORMATION: n = A,T,C or G

<400> SEQUENCE: 39
cgtgtgctct tccgatctnn nntcgtcggc agcgtcagat gtgtataaga gacag            55

<210> SEQ ID NO 40
<211> LENGTH: 55
<212> TYPE: DNA
<213> ORGANISM: Artificial Sequence
<220> FEATURE:
<223> OTHER INFORMATION: Synthetic Construct

<400> SEQUENCE: 40
cgtgtgctct tccgatctat cgtcgtcggc agcgtcagat gtgtataaga gacag            55

<210> SEQ ID NO 41
<211> LENGTH: 55
<212> TYPE: DNA
<213> ORGANISM: Artificial Sequence
<220> FEATURE:
<223> OTHER INFORMATION: Synthetic Construct

<400> SEQUENCE: 41
cgtgtgctct tccgatcttg actcgtcggc agcgtcagat gtgtataaga gacag            55

<210> SEQ ID NO 42
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19, 20, 21
<223> OTHER INFORMATION: n = A,T,C or G

<400> SEQUENCE: 42
cgacgctctt ccgatctnnn ngtctcgtgg gctcggagat gtgtataaga gacag            55

<210> SEQ ID NO 43
<211> LENGTH: 55
<212> TYPE: DNA
<213> ORGANISM: Artificial Sequence
<220> FEATURE:
<223> OTHER INFORMATION: Synthetic Construct
```

```
<400> SEQUENCE: 43
cgacgctctt ccgatctcta ggtctcgtgg gctcggagat gtgtataaga gacag        55

<210> SEQ ID NO 44
<211> LENGTH: 55
<212> TYPE: DNA
<213> ORGANISM: Artificial Sequence
<220> FEATURE:
<223> OTHER INFORMATION: Synthetic Construct

<400> SEQUENCE: 44
cgacgctctt ccgatctgca tgtctcgtgg gctcggagat gtgtataaga gacag        55

<210> SEQ ID NO 45
<211> LENGTH: 4
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4
<223> OTHER INFORMATION: n = A,T,C or G

<400> SEQUENCE: 45 nnnn                                                                  4

<210> SEQ ID NO 46
<211> LENGTH: 1
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = deoxyUridine

<400> SEQUENCE: 46 n                                                                     1

<210> SEQ ID NO 47
<211> LENGTH: 24
<212> TYPE: DNA
<213> ORGANISM: Artificial Sequence
<220> FEATURE:
<223> OTHER INFORMATION: Synthetic Construct

<400> SEQUENCE: 47
ctcggagatg tgtataagag acag                                           24

<210> SEQ ID NO 48
<211> LENGTH: 58
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 29, 30, 31, 32, 33, 34
<223> OTHER INFORMATION: n = A,T,C or G

<400> SEQUENCE: 48
ctgtctctta tacacatctc cgagcgccnn nnnnatctcg tatgccgtct tctgcttg      58

<210> SEQ ID NO 49
<211> LENGTH: 43
```

```
<212> TYPE: DNA
<213> ORGANISM: Artificial Sequence
<220> FEATURE:
<223> OTHER INFORMATION: Synthetic Construct

<400> SEQUENCE: 49
gacgctgccg acgagtgtag atctcggtgg tcgccgtatc att                    43
```

METHODS FOR DETECTING PROTEIN BINDING SEQUENCES AND TAGGING NUCLEIC ACIDS

RELATED APPLICATIONS

This application claims priority benefit from U.S. Provisional Patent Application No. 62/509,328, filed on May 22, 2017, the content of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 153822000200SEQLIST.TXT, date recorded: May 18, 2018, size: 11 KB).

FIELD OF THE INVENTION

The present invention relates to a method of analyzing protein binding sequence, a method of making sequencing library, and compositions for performing such methods.

BACKGROUND OF THE INVENTION

Chromatin immunoprecipitation (ChIP) is an affinity assay for detecting the interaction between a particular protein and DNA in cells. It is widely applied for studying not only DNA-binding proteins involved in transcription, splicing, replication, and DNA repair, but also histone modifications associated with different chromatin status. Conventional ChIP uses a protein specific antibody to enrich sheared chromatin (with or without fixation) associated with the protein of interest or target histone modifications, then the underlying DNA can be recovered and detected at small scale by qPCR (ChIP-qPCR), or at large scale by DNA microarray (ChIP-chip) or high throughput sequencing (ChIP-seq). ChIP-seq provides better resolution and coverage with less artifacts and bias. Genomic data obtained from numerous ChIP-seq experiments have significantly improved our understanding of the molecular mechanisms underlying complex biological events such as embryogenesis, tissue homeostasis, and pathogenesis.

Despite of their indispensability in studying gene regulation and epigenetic mechanisms, ChIP-seq experiments are time-consuming, less user-friendly for trouble-shooting, and require a large amount of starting materials, which is very challenging when experimental materials are limited. One major limitation of current ChIP-seq methods is the inadequacy of quantitatively comparing ChIPed DNA between experiments. Sometimes it is even difficult to compare results between experiments performed with the same antibody. Certain solutions have been recently developed but are still not ideal. For example, using chromatin from another species as spike-in control is limited to study of conserved proteins and histone modifications; and indexing chromatin after Micrococcal Nuclease (MNase) digestion is restricted to study certain histone modifications. Furthermore, both strategies increase the complexity of experiments and require greater expertise in performing such assays. Thus, a sufficiently robust and easier method to identify DNA sequence of interest or molecular interactions is needed.

The disclosures of all publications, patents, patent applications and published patent applications referred to herein are hereby incorporated herein by reference in their entirety.

BRIEF SUMMARY OF THE INVENTION

The present invention provides methods of analyzing binding sequences on a chromatin to which a protein of interest binds, methods of sequencing a nucleic acid sequence on a chromosome, methods of making sequencing library, methods of tagging nucleic acids, methods of tagmenting nucleic acids using Tn5 transposome complex, and compositions for performing such methods.

One aspect of the present application provides a method of analyzing the binding sequences on a chromosome to which a protein of interest binds, comprising: (a) randomly inserting a plurality of transposon end compositions comprising transposon end into the chromatin or double-stranded nucleic acid fragments thereof in the presence of a transposase; (b) subjecting the double-stranded nucleic acid fragments inserted with transposon end compositions comprising transposon end to immunoprecipitation using an antibody specifically recognizing the protein of interest; and (c) analyzing the nucleic acid fragment sequences to which the protein of interest binds. In some embodiments, the protein of interest binds directly to the chromatin. In some embodiments, the protein of interest binds indirectly to the chromatin. In some embodiments, the protein of interest is selected from the group consisting of transcription factor, histone, histone modification, chromatin remodeler, chromatin modifier, transcription machinery elements, insulator binding protein such as CTCF.

In some embodiments according to any one of the methods described above, step (a) further comprises extracting chromatin from a sample.

In some embodiments according to any one of the methods described above, the chromatin in step (a) is cross-linked with a reversible cross-linking agent. In some embodiments, the reversible cross-linking agent is formaldehyde. In some embodiments, the final formaldehyde concentration during cross-linking is about 0.05% to about 1%, such as about 0.5%. In some embodiments, the cross-linking time is no more than about 10 min, such as about 5 min to about 10 min.

In some embodiments according to any one of the methods described above, the chromatin in step (a) is pre-fragmented before transposon insertion. In some embodiments, the pre-fragmentation is generated by sonication or enzyme digestion. In some embodiments, at least about 50% to about 95% of the fragmented chromatin is about 100 bp to about 5000 bp. In some embodiments, at least about 50% to at least about 95% of the fragmented chromatin is about 100 bp to about 500 bp.

In some embodiments according to any one of the methods described above, the transposase and transposon end compositions in step (a) are pre-incubated to form a transposome complex comprising a transposase and two transposon end compositions comprising transposon end.

In some embodiments according to any one of the methods described above, the transposase in step (a) is from an organism selected from the group consisting of bacteria, plants, insects, or animals. In some embodiments, the transposase is from bacteria. In some embodiments, the transposase is an *E. coli* transposase. In some embodiments, the transposase is Tn5.

In some embodiments according to any one of the methods described above, the transposon end composition comprising transposon end further comprises an amplification tag and a restriction site tag, wherein the transposon end composition comprises, from 5' to 3': an amplification tag, a restriction site tag, and a transposon end.

In some embodiments according to any one of the methods described above, the transposon end is a double-stranded nucleic acid.

In some embodiments according to any one of the methods described above, the transferred strand of the transposon end comprises SEQ ID NO: 1.

In some embodiments according to any one of the methods described above, the amplification tag is a single-strand nucleic acid.

In some embodiments according to any one of the methods described above, the amplification tag comprises high GC content with a melting temperature Tm of about 65° C. in NEB Q5® DNA polymerase buffer.

In some embodiments according to any one of the methods described above, the amplification tag comprises SEQ ID NO: 3.

In some embodiments according to any one of the methods described above, the restriction site tag is a single-strand nucleic acid.

In some embodiments according to any one of the methods described above, the restriction site tag is deoxyUridine (U).

In some embodiments according to any one of the methods described above, the transposon end composition comprising amplification tag, restriction site tag, and transposon end further comprises one or more of a sample index tag, a unique molecular identifier tag, and an amplification facilitating tag at the 5' end of the transposon end. In some embodiments, the transposon end composition comprises, from 5' to 3': a sample index tag, an unique molecular identifier tag, an amplification tag, a restriction site tag, an amplification facilitating tag, and a transposon end. In some embodiments, the sample index tag is a single-strand nucleic acid. In some embodiments, the sample index tag comprises a sequence selected from SEQ ID NOs: 24-32. In some embodiments, the unique molecular identifier tag is a single-strand nucleic acid. In some embodiments, the unique molecular identifier tag comprises about 3 nt to about 20 nt random dNTP. In some embodiments, the unique molecular identifier tag comprises about 5 nt random dNTP. In some embodiments, the unique molecular identifier tag comprises SEQ ID NO: 38. In some embodiments, the amplification facilitating tag is a single-strand nucleic acid. In some embodiments, the amplification facilitating tag comprises SEQ ID NO: 4. In some embodiments, the transferred strand of the transposon end composition comprises a sequence selected from SEQ ID NOs: 5-13. In some embodiments, step (b) further comprises pooling at least two chromatin samples inserted with transposon end compositions comprising different sample index tags.

In some embodiments according to any one of the methods described above, the antibody in step (b) can be one or more antibodies specifically recognizing different proteins of interest.

In some embodiments according to any one of the methods described above, the antibody in step (b) can be one or more antibodies specifically recognizing the same protein of interest.

In some embodiments according to any one of the methods described above, the antibody in step (b) is pre-incubated with beads compatible with immunoprecipitation assay. In some embodiments, the beads are magnetic, Agarose, or other resin.

In some embodiments according to any one of the methods described above, step (c) comprises sequencing the nucleic acid fragments. In some embodiments, the sequencing primers comprise a first sequencing primer that can bind to at least a portion of the amplification tag. In some embodiments, the first sequencing primer comprises SEQ ID NO: 21. In some embodiments, the sequencing primers further comprise a second sequencing primer that can bind to at least a portion of the transposon end. In some embodiments, the second sequencing primer comprises SEQ ID NO: 22. In some embodiments, the sequencing primers further comprise a third sequencing primer comprising SEQ ID NO: 23.

In some embodiments according to any one of the methods described above, step (c) comprises quantifying the nucleic acid fragments of interest.

In some embodiments according to any one of the methods described above, step (c) further comprises denaturing the double-stranded nucleic acid fragments associated with the protein of interest specifically recognized by the antibody from step (b) into single-strand nucleic acid fragments. In some embodiments, the denaturation is carried out by heating.

In some embodiments according to any one of the methods described above, step (c) further comprises removing the protein of interest from the nucleic acid fragments. In some embodiments, removing the protein of interest from the nucleic acid fragments is carried out by reverse-crosslinking. In some embodiments, the denaturing and/or reverse-crosslinking is carried out at about 95° C. for about 60 min.

In some embodiments according to any one of the methods described above, step (c) further comprises removing nucleotide(s) from 3'-hydroxyl termini of the double-stranded nucleic acid fragments associated with the protein of interest until the nicking is blocked by the protein of interest or associated protein thereof. In some embodiments, the nucleotide removing is carried out by a 3'→5' exonuclease, such as Exonuclease III.

In some embodiments according to any one of the methods described above, step (c) further comprises self-circularizing the single-strand nucleic acid fragments after denaturation. In some embodiments, the self-circularization is carried out by a single-strand DNA (ssDNA) ligase, such as CircLigase™ or *Methanobacterium* thermoautotrophicum RNA ligase 1 (MthRn1). In some embodiments, step (c) further comprises linearizing the self-circularized single-strand nucleic acid fragments by generating a breakage at the restriction site tag. In some embodiments, linearizing the self-circularized single-strand nucleic acid fragments by generating a breakage at the restriction site tag is carried out by USER™ enzyme, or a mixture of Uracil DNA glycosylase (UDG) and the DNA glycosylase-lyase Endonuclease VIII. In some embodiments, step (c) further comprises PCR amplifying the linearized single-strand nucleic acid fragments. In some embodiments, the PCR primers comprise a first PCR primer comprising a first sequencing tag and a first annealing tag, and a second PCR primer comprising a second sequencing tag, an experimental index tag and a second annealing tag. In some embodiments, the first and second sequencing tags can bind to complementary sequencing tags conjugated on a surface. In some embodiments, the surface is a parallel sequencing flow cell surface. In some embodiments, the first annealing tag can bind to at least a portion of the amplification tag, wherein the second annealing tag can bind to at least a portion of the transposon end. In some embodiments, the first PCR primer comprises SEQ ID NO: 14, and the second PCR primer comprises a sequence selected from SEQ ID NOs: 15-20.

In some embodiments according to any one of the methods described above, the chromosome is from an organism selected from bacteria, plant, invertebrates, insects, fish, reptiles, amphibians, arachnids, avian, non-human mammals, and human.

Another aspect of the present application provides a method of sequencing a nucleic acid sequence on a chromosome, comprising: (a) randomly inserting a plurality of transposon end compositions comprising transposon end into the chromatin or double-stranded nucleic acid fragments thereof in the presence of a transposase, wherein the transposon end composition comprises, from 5' to 3': a sample index tag, an amplification tag, a restriction site tag, and a transposon end; and (b) determining the nucleic acid fragment sequences. In some embodiments, step (a) further comprises extracting chromatin from a sample.

In some embodiments according to any one of the methods described above, the chromatin in step (a) is cross-linked with a reversible cross-linking agent. In some embodiments, the reversible cross-linking agent is formaldehyde. In some embodiments, the final formaldehyde concentration during cross-linking is about 0.05% to about 1%, such as about 0.5%. In some embodiments, the cross-linking time is no more than about 10 min, such as about 5 min to about 10 min.

In some embodiments according to any one of the methods described above, the chromatin in step (a) is pre-fragmented. In some embodiments, the pre-fragmentation is generated by sonication or enzyme digestion. In some embodiments, at least about 50% to about 95% of the fragmented chromatin is about 100 bp to about 5000 bp. In some embodiments, at least about 50% to at least about 95% of the fragmented chromatin is about 100 bp to about 500 bp.

In some embodiments according to any one of the methods described above, the transposase and transposon end compositions in step (a) are pre-incubated to form a transposome complex comprising a transposase and two transposon end compositions comprising transposon end.

In some embodiments according to any one of the methods described above, the transposase in step (a) is from an organism selected from the group consisting of bacteria, plants, insects, or animals. In some embodiments, the transposase is from bacteria. In some embodiments, the transposase is an *E. coli* transposase, such as Tn5.

In some embodiments according to any one of the methods described above, the transposon end is a double-stranded nucleic acid.

In some embodiments according to any one of the methods described above, the transferred strand of the transposon end comprises SEQ ID NO: 1.

In some embodiments according to any one of the methods described above, the sample index tag is a single-strand nucleic acid.

In some embodiments according to any one of the methods described above, the sample index tag comprises a sequence selected from SEQ ID NOs: 24-32.

In some embodiments according to any one of the methods described above, the amplification tag is a single-strand nucleic acid.

In some embodiments according to any one of the methods described above, the amplification tag comprises high GC content with a melting temperature Tm of about 65° C. in NEB Q5® DNA polymerase buffer.

In some embodiments according to any one of the methods described above, the amplification tag comprises SEQ ID NO: 3.

In some embodiments according to any one of the methods described above, the restriction site tag is a single-strand nucleic acid.

In some embodiments according to any one of the methods described above, the restriction site tag is deoxyUridine (U).

In some embodiments according to any one of the methods described above, the transposon end composition comprising sample index tag, amplification tag, restriction site tag, and transposon end further comprises one or both of a unique molecular identifier tag and an amplification facilitating tag at the 5' end of the transposon end. In some embodiments, the transposon end composition comprises, from 5' to 3': a sample index tag, an unique molecular identifier tag, an amplification tag, a restriction site tag, an amplification facilitating tag, and a transposon end. In some embodiments, the transferred strand of the transposon end composition comprises a sequence selected from SEQ ID NOs: 5-13.

In some embodiments according to any one of the methods described above, the unique molecular identifier tag is a single-strand nucleic acid.

In some embodiments according to any one of the methods described above, the unique molecular identifier tag comprises about 3 nt to about 20 nt random dNTP. In some embodiments, the unique molecular identifier tag comprises about 5 nt random dNTP. In some embodiments, the unique molecular identifier tag comprises SEQ ID NO: 38.

In some embodiments according to any one of the methods described above, the amplification facilitating tag is a single-strand nucleic acid.

In some embodiments according to any one of the methods described above, the amplification facilitating tag comprises SEQ ID NO: 4.

In some embodiments according to any one of the methods described above, step (b) further comprises pooling at least two chromatin samples inserted with transposon end compositions comprising different sample index tags.

In some embodiments according to any one of the methods described above, step (b) comprises sequencing the nucleic acid fragments. In some embodiments, the sequencing primers comprise a first sequencing primer and a second sequencing primer, wherein the first sequencing primer can bind to at least a portion of the amplification tag, wherein the second sequencing primer can bind to at least a portion of the transposon end. In some embodiments, the sequencing primers comprise a first sequencing primer comprising SEQ ID NO: 21. In some embodiments, the sequencing primers further comprise a second sequencing primer comprising SEQ ID NO: 22. In some embodiments, the sequencing primers further comprise a third sequencing primer comprising SEQ ID NO: 23.

In some embodiments according to any one of the methods described above, step (b) comprises quantifying the nucleic acid fragment of interest.

In some embodiments according to any one of the methods described above, step (b) further comprises denaturing the double-stranded nucleic acid fragments from step (a) into single-strand nucleic acid fragments. In some embodiments, the denaturation is carried out by heating.

In some embodiments according to any one of the methods described above, step (b) further comprises removing any protein associated with the nucleic acid fragments. In some embodiments, removing the protein from the nucleic acid fragments is carried out by reverse-crosslinking. In some embodiments, the denaturing and/or reverse-crosslinking is carried out at about 95° C. for about 60 min.

In some embodiments according to any one of the methods described above, step (b) further comprises removing nucleotide(s) from 3'-hydroxyl termini of the double-stranded nucleic acid fragments associated with the protein of interest until the nicking is blocked by the protein of interest or associated protein thereof. In some embodiments, the nucleotide removing is carried out by a 3'→5' exonuclease. In some embodiments, the 3'→5' exonuclease is Exonuclease III.

In some embodiments according to any one of the methods described above, step (b) further comprises self-circularizing the single-strand nucleic acid fragments after denaturation. In some embodiments, the self-circularization is carried out by a single-strand DNA (ssDNA) ligase, such as CircLigase™ or *Methanobacterium* thermoautotrophicum RNA ligase 1 (MthRn1). In some embodiments, step (b) further comprises linearizing the self-circularized single-strand nucleic acid fragments by generating a breakage at the restriction site tag. In some embodiments, linearizing the self-circularized single-strand nucleic acid fragments by generating a breakage at the restriction site tag is carried out by USER™ enzyme or a mixture of Uracil DNA glycosylase (UDG) and the DNA glycosylase-lyase Endonuclease VIII. In some embodiments, step (b) further comprises PCR amplifying the linearized single-strand nucleic acid fragments. In some embodiments, the PCR primers comprise a first PCR primer comprising a first sequencing tag and a first annealing tag, and a second PCR primer comprising a second sequencing tag, an experimental index tag and a second annealing tag. In some embodiments, the first and second sequencing tags can bind to complementary sequencing tags conjugated on a surface. In some embodiments, the surface is a parallel sequencing flow cell surface. In some embodiments, the first annealing tag can bind to at least a portion of the amplification tag, wherein the second annealing tag can bind to at least a portion of the transposon end. In some embodiments, the first PCR primer comprises SEQ ID NO: 14, and the second PCR primer comprises a sequence selected from SEQ ID NOs: 15-20.

In some embodiments according to any one of the methods described above, the chromatin is from an organism selected from bacteria, plant, invertebrates, insects, fish, reptiles, amphibians, arachnids, avian, non-human mammals, and human.

Further provided is a transposon end composition comprising, from 5' to 3': an amplification tag, a restriction site tag, and a transposon end. In some embodiments, the transposon end is double-stranded nucleic acid. In some embodiments, the transferred strand of the transposon end comprises SEQ ID NO: 1.

In some embodiments according to any one of the transposon end compositions described above, the amplification tag is a single-strand nucleic acid.

In some embodiments according to any one of the transposon end compositions described above, the amplification tag comprises SEQ ID NO: 3.

In some embodiments according to any one of the transposon end compositions described above, the restriction site tag is a single-strand nucleic acid.

In some embodiments according to any one of the transposon end compositions described above, the restriction site tag is deoxyUridine (U).

In some embodiments according to any one of the transposon end compositions described above, further comprises one or more of a sample index tag, a unique molecular identifier tag, and an amplification facilitating tag at the 5' end of the transposon end. In some embodiments, the transposon end composition comprises, from 5' to 3': a sample index tag, an unique molecular identifier tag, an amplification tag, a restriction site tag, an amplification facilitating tag, a transposon end. In some embodiments, the sample index tag is a single-strand nucleic acid. In some embodiments, the sample index tag comprises a sequence selected from SEQ ID NOs: 24-32. In some embodiments, the unique molecular identifier tag is a single-strand nucleic acid. In some embodiments, the unique molecular identifier tag comprises about 3 nt to about 20 nt random dNTP. In some embodiments, the unique molecular identifier tag comprises about 5 nt random dNTP. In some embodiments, the unique molecular identifier tag comprises SEQ ID NO: 38. In some embodiments, the amplification facilitating tag is a single-strand nucleic acid. In some embodiments, the amplification facilitating tag comprises SEQ ID NO: 4. In some embodiments, the transferred strand of the transposon end composition comprises a sequence selected from SEQ ID NOs: 5-13.

Further provided is a transposome complex comprising a transposase and two transposon end compositions of any one of the transposon end compositions described above.

Further provided is a kit for preparing nucleic acid sequencing library, comprising: (a) a transposase; (b) transposon end compositions of any one of the transposon end compositions described above; (c) PCR primers comprising a first PCR primer comprising SEQ ID NO: 14, and the second PCR primer comprising a sequence selected from SEQ ID NOs: 15-20; and (d) sequencing primers comprising a first sequencing primer comprising SEQ ID NO: 21, and a second sequencing primer comprising SEQ ID NO: 22. In some embodiments, the transposase is Tn5.

In some embodiments according to any one of the kits described above, further comprises an CircLigase™ enzyme or *Methanobacterium* thermoautotrophicum RNA ligase 1 (MthRn1).

In some embodiments according to any one of the kits described above, further comprises an USER™ enzyme, or a mixture of Uracil DNA glycosylase (UDG) and the DNA glycosylase-lyase Endonuclease VIII.

In some embodiments according to any one of the kits described above, further comprises an Exonuclease III.

In some embodiments according to any one of the kits described above, further comprises magnetic beads for DNA clean up.

BRIEF DESCRIPTION OF THE DRAWINGS

FIG. 1 depicts an exemplary design of the transposon end composition described herein.

FIG. 2 depicts an exemplary workflow of ChIP-SMITH described herein.

FIG. 3 depicts advantages of the bidirectional transposon design of the transposon end compositions described herein.

FIG. 4 depicts an exemplary workflow of ChIP-SMITH library preparation and sequencing.

FIG. 5 depicts the effects of transposon end composition oligonucleotide length on Tn5 activity.

FIG. 6A depicts the effects of cross-linked chromatin and/or SDS on Tn5 activity. FIG. 6B depicts the chromatin shearing comparison by sonicator between shearing in regular ChIP buffer and shearing in Tn5 Shearing buffer with 0.02% SDS.

FIG. 7 depicts the effects of different detergents on Tn5 activity.

FIG. 8 depicts Tn5 activities under different detergent treatments and further buffer dilution.

FIG. 9 shows the sequencing results comparison among ChIP-SMITH, index-tagmenting ChIP using dual-transposon design, and regular ChIP using antibodies against RNA polymerase II. Genomic snapshots were exemplified at Ci-TT1-like 6 gene and Ci-epi gene. "Regular ChIP" was performed using regular ChIP-seq method, comprising sonication, ChIP, library preparation using commercially available kits. "Index-tagmented ChIP" was shown with two replicates, performed using Tn5 transposome complex (modified Tn5 dual-transposon design) to tagment chromatin, ChIP (following index-tagmented ChIP method described herein), reverse-crosslinking at 65° C., then PCR using the primers from the Kit. "ChIP-SMITH" was performed using the bidirectional transposon design described herein, following ChIP-SMITH method described herein.

FIG. 10 shows exemplary workflow of index-tagmented ChIP with modified Nextera® dual-transposon design.

DETAILED DESCRIPTION OF THE INVENTION

The present invention provides a novel method of analyzing binding sequences on a chromatin to which a protein of interest binds, a method of sequencing a nucleic acid sequence on a chromosome, a method of making sequencing library, and compositions for performing such methods. Briefly, a Tn5 transposome complex is employed to fragment and tag chromatin or DNA from different biological samples with different indexes, so different chromatin or DNA samples can be pooled in one tube for ChIPing with the same antibody or making sequencing libraries. The method is herein referred to as "ChIP-SMITH" (Simple Multiplexing Index by Transposase with High-resolution ChIP), but is not limited to the use in ChIP.

The present invention has the following advantages. 1) Efficient: compared to conventional ChIP in which each individual sample has to be ChIPed separately, even when using the same antibody, the present invention allows pooling multiple barcoded biological samples into one tube before ChIP, which significantly shorted the time and reduced complexity of the experiment. 2) Quantitative: compared to conventional ChIP which is difficult to normalize across multiple sequencing experiments, the present invention allows direct quantitative comparison among samples, because the relative portion among samples in the pooled ChIP and control reactions is fixed throughout the entire experiment, such as during immunoprecipitation, library preparation, and amplification for high-throughput sequencing. 3) Sensitive and requires less starting materials: each step during conventional ChIP and library preparation involves certain percentage of material loss. By pooling multiple barcoded samples together, the recovery rate per sample will be increased, which is extremely beneficial for experiments with limited amount of starting materials. In addition, un-tagged chromatin in the experiment can serve as "carrier" chromatin to reduce loss and facilitate precipitation of the tagged chromatin. Furthermore, the bidirectional transposon design of the present invention enables much higher recovery rate during library preparation, which minimizes the required amount of starting material (see, e.g., FIG. 1 and FIG. 3). 4) High resolution: the present invention employs an exonuclease which gets rid of free, unbound DNA, and digests DNA bound by protein of interest (e.g., transcription factors, or nucleosomes) till the protein binding boundary, which fine-maps the protein binding position. 5) Broad application: the present invention is applicable for both cross-linked and uncross-linked chromatin sample, can be used for detecting both histone modifications and protein binding (e.g., transcription factor binding, or nucleosome occupancy), as well as for making sequencing libraries. The present invention is compatible with any ChIP-grade antibodies. 6) Easy to perform: tagging chromatin before ChIP makes the whole experiment simple and straightforward. There is only one step of barcoding between the optional brief shearing step and ChIP, and only one step of library preparation after DNA cleanup, which allows the entire assay to be finished within two days. 7) Moreover, due to the size-limitation of what the transposon can cut (larger than about 50 bp), the present invention prevents the risk of over-shearing, which is a mistake easily made by sonication or enzymatic digestion and may greatly affect the result.

Accordingly, one aspect of the present application provides a method of analyzing the binding sequences on a chromosome to which a protein of interest (e.g., transcription factor, chromatin remodeler, histone modifier, histone modification, or nucleosome) binds, comprising: (a) randomly inserting a plurality of transposon end compositions comprising transposon end into the chromatin or double-stranded nucleic acid fragments thereof in the presence of a transposase; (b) subjecting the double-stranded nucleic acid fragments inserted with transposon end compositions comprising transposon end to immunoprecipitation using an antibody specifically recognizing the protein of interest; and (c) analyzing the nucleic acid fragment sequences to which the protein of interest binds.

Another aspect of the present application provides method of sequencing a nucleic acid sequence on a chromosome, comprising: (a) randomly inserting a plurality of transposon end compositions comprising transposon end into the chromatin or double-stranded nucleic acid fragments thereof in the presence of a transposase, wherein the transposon end composition comprises, from 5' to 3': a sample index tag, an amplification tag, a restriction site tag, and a transposon end; and (b) determining the nucleic acid fragment sequences.

Also provided are transposon end composition, transposome complex comprising a transposase and transposon end compositions thereof, and kit for preparing nucleic acid sequencing library.

I. Definitions

A "mononucleoside" or "nucleoside", as used herein, refers to a compound consisting of a purine (guanine (G) or adenine (A)) or pyrimidine (thymine (T), uridine (U), or cytidine (C)) base covalently linked to a pentose sugar, whereas "nucleotide" refers to a nucleoside phosphorylated at one of the hydroxyl groups of the pentose sugar. The term "canonical" is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyribonucleosides, deoxyribonucleotides, or 2'-deoxyribonucleoside-5'-triphosphates that contain a non-canonical base. For example, although uracil is a common nucleic acid base in RNA, uracil is a non-canonical base in DNA. "Non-canonical bases" are found in nucleic acids as a result of incorporation of non-canonical nucleotides (e.g., by synthesis using an oligonucleotide synthesizer or by synthesis using a DNA polymerase) or as a result of modification of existing bases (canonical or non-canonical).

A "nucleic acid" or "polynucleotide" means a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5" of or the "5' nucleotide" and the nucleotide that is linked to the 3'-position of the 5' nucleotide is referred to as "3" of or the "3' nucleotide." As used herein, the terms "5'-of" and "3'-of" refer to the position or orientation of a particular chemical group, nucleotide, sequence of nucleotides, or genetic element (e.g., an RNA polymerase promoter sequence) relative to another chemical group, nucleotide, sequence of nucleotides, or genetic element within a single strand of a nucleic acid. If a first nucleic acid sequence is 3'-of a second sequence on one strand, the complement of the first sequence will be 5'-of the complement of the second sequence on the complementary strand. The description of the invention will be understood with respect to the relative 5' or 3' position and orientation of a sequence or genetic element within a particular nucleic acid strand.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common or "canonical" nucleic acid bases (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. In some cases, uridine can be present as a base in DNA. Those in the art commonly think of a small polynucleotide as an "oligonucleotide." The term "oligonucleotide" as used herein is defined as a molecule comprising of two or more deoxyribonucleotides (in which case, it may also be referred to as an "oligodeoxyribonucleotide." or ribonucleotides, preferably about 6 to 100 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include: (1) modification of the $T_m$; (2) changing the susceptibility of the polynucleotide to one or more nucleases; (3) providing a restriction site, such as a dUMP residue, which is cleaved by uracil-N-glycosylase plus alkaline conditions or an endonuclease, e.g., endonuclease IV, or, such as an 8-oxo-dGMP residue, which is cleaved by 8-oxoguanine DNA glycosylase (also known as [fapy-DNA glycosylase or Fpg) plus alkaline conditions or an endonuclease, e.g., endonuclease IV; (4) providing a moiety for attachment of a label or an affinity tag; (5) providing a label or a quencher for a label; or (6) providing a moiety, such as biotin, as an affinity tag for attaching to another molecule which is in solution or bound to a surface.

In order to accomplish the goals of the invention, by way of example, the nucleic acid bases in the mononucleotides of one or more positions of a polynucleotide or oligonucleotide may comprise guanine, adenine, uracil, thymine, or cytidine, or alternatively, one or more of the nucleic acid bases may comprise a modified base, such as, but not limited to xanthine, allyamino-uracil, allyamino-thymidine, hypoxanthine, 2-aminoadenine, 5-propynyl uracil, 5-propynyl cytosine, 4-thiouracil, 6-thioguanine, aza and deaza uracils, thymidines, cytosines, adenines, or guanines Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show an example of the broad range of bases which may be used for a particular purpose in a method.

With respect to nucleic acids or polynucleotides of the invention, one or more of the sugar moieties can comprise 2'-deoxyribose, or alternatively, one or more of the sugar moieties can be some other sugar moiety, such as, but not limited to, ribose, or 2'-fluoro-2'-deoxyribose or 2'-O-methyl-ribose, which provide resistance to some nucleases, or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases.

When referring to an oligonucleotide or a portion of an oligonucleotide that exhibits a "random sequence," we mean that the oligonucleotide or portion thereof is synthesized (e.g., using an oligonucleotide synthesizer) using equal amounts of all four of the canonical nucleotide bases (A, G, C, and T or U) for very nucleotide position within the random sequence portion. This method results in synthesis of a mixture of oligonucleotides comprising (4 to the n power)+1 of different oligonucleotides, where "n" equals the number of nucleotide positions within the random sequence portion. Thus, in these embodiments, the oligonucleotide comprises a mixture of many different oligonucleotides, representing all possible sequences for the random sequence portion. When referring to an oligonucleotide or a portion of an oligonucleotide that exhibits a "semi-random sequence," we mean that the semi-random oligonucleotide or portion is synthesized (e.g., using an oligonucleotide synthesizer) wherein some nucleotide positions are synthesized using equal amounts of all four of the canonical nucleotide bases (A, G, C, and T or U) (i.e., those positions are "random" as described above) but one or more other positions within the semi-random portion are synthesized using only one, two, or three, rather than all four, of the canonical base nucleotides (i.e., A, C, G, and T or U). In some embodiments, an oligonucleotide contains one or more nucleotides with a "degenerate base," by which we mean a nucleic acid base that is capable of base-pairing with one or more nucleic acid bases other than according to the standard base-pairing rules that A pairs with T or U and G pairs with C, and a "degenerate nucleotide" is a nucleotide that contains a degenerate base. A "portion" or "region," used interchangeably herein, of a polynucleotide or oligonucleotide (including a primer) is a contiguous sequence of 2 or more bases. In other embodiments, a region or portion is at least about any of 1, 2, 3, 5, 10, 15, 20, 25, 50, 75, or even more contiguous nucleotides. If the random or semi-random sequence comprises all of the nucleotides in the oligonucleotide, it may be referred to, respectively, as a "random oligonucleotide" or a "semi-random oligonucleotide."

A "primer" is an oligonucleotide ("oligo"), generally with a free 3'-OH group, that can be extended by a nucleic acid polymerase. For a template-dependent polymerase, generally at least the 3'-portion of the primer oligo is complementary to a portion of a template nucleic acid, to which the oligo "binds" (or "complexes," "anneals," or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

A "single-strand-specific DNase" means a DNase that specifically digests single-stranded DNA, but that does not digest single-stranded RNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular base-pairing). The single-strand-specific DNase can be an endonuclease or an exonuclease, so long as it is active in specifically digesting single-stranded DNA to monomers or short oligodeoxyribonucleotides. In some preferred embodiments, oligodeoxyribonucleotides, including primers, are removed from the reaction mixture after step of the method in which they are used by digestion with a single-strand-specific DNase. Exonuclease I (ExoI), exonuclease III (ExoIII), exonuclease VII (ExoVII), and Rec J exonuclease are exemplary single-strand-specific DNases.

A "template" is a nucleic acid molecule that is being copied by a nucleic acid polymerase, such as a DNA polymerase. Whether the nucleic acid molecule comprises two strands (i.e., is "double-stranded") or only one strand (i.e., is "single-stranded"), the strand of said nucleic acid molecule that serves to specify the sequence of nucleotides exhibited by a nucleic acid that is synthesized is the "template" or "the template strand." The nucleic acid synthesized by the nucleic acid polymerase is complementary to the template. Both RNA and DNA are always synthesized in the 5'-to-3' direction, beginning at the 3'-end of the template strand, and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase, but a primer is not required to initiate synthesis by a DNA-dependent RNA polymerase, which is usually called simply an "RNA polymerase."

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," i.e., an increase in the amount of a desirable protein and/or nucleic acid sequence in the sample.

As used herein, the term "ligase" refers to a nucleic acid modifying enzyme that catalyzes intra- and intermolecular formation of phosphodiester bonds between 5'-phosphate and 3'-hydroxyl termini of nucleic acid strands. Ligases include, e.g., template-independent ligases, such as CIRCLIGASE™ ssDNA ligase, that can join ends of single-stranded RNA and DNA, and template-dependent or homologous ligases, that seal nicks in double-stranded DNA.

As used herein, a "homologous ligase" or "template-dependent ligase" means a DNA ligase that catalyzes intra- and intermolecular formation of phosphodiester bonds between 5'-phosphate and 3'-hydroxyl termini of DNA strands that are adjacent to each other when annealed to a complementary polynucleotide. Some embodiments of intramolecular ligation produce a circular molecule and are referred to as "circularization". The polynucleotide to which both ends of the DNA ends to be ligated anneal adjacently is referred to herein as a "ligation template" and the ligation is referred to as "homologous ligation" or "template-dependent ligation." The ligation template can be a complementary DNA sequence in genomic or other DNA in a biological sample (in which case, it is often referred to as a "target sequence"), or the ligation template can be a "bridging oligodeoxyribonucleotide" or "ligation splint oligodeoxyribonucleotide" (or "ligation splint") that is synthesized and/or provided specifically for use in a particular assay or method.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated in an in vitro or in vivo transposition reaction. A transposase of the invention also includes integrases from retrotransposons and retroviruses.

The term "transposon end" means a double-stranded DNA that exhibits only the nucleotide sequences (the "transposon end sequences") that are necessary to form the complex with the transposase or integrase enzyme that is functional in an in vitro or in vivo transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro or in vivo transposition reaction. A transposon end exhibits two complementary sequences consisting of a "transferred transposon end sequence" or "transferred strand" and a "non-transferred transposon end sequence," or "non-transferred strand"

A "transposon end composition" means a composition comprising a transposon end (i.e., the minimum double-stranded DNA segment that is capable of acting with a transposase to undergo a transposition reaction), optionally plus additional sequence or sequences 5'-of the transferred transposon end sequence and/or 3'-of the non-transferred transposon end sequence. For example, a transposon end attached to a tag is a "transposon end composition." In some embodiments, the transposon end composition comprises or consists of two transposon end oligonucleotides consisting of the "transferred transposon end oligonucleotide" or "transferred strand" and the "non-transferred strand end oligonucleotide," or "non-transferred strand" which, in combination, exhibit the sequences of the transposon end, and in which one or both strand comprise additional sequence.

The terms "transferred transposon end oligonucleotide" and "transferred strand" are used interchangeably and refer to the transferred portion of both "transposon ends" and "transposon end compositions," i.e., regardless of whether the transposon end is attached to a tag or other moiety. Similarly, the terms "non-transferred transposon end oligonucleotide" and "non-transferred strand" are used interchangeably and refer to the non-transferred portion of both "transposon ends" and "transposon end compositions." In some embodiments, a transposon end composition is a "hairpin transposon end composition." As used herein, a "hairpin transposon end composition." means a transposon end composition consisting of a single oligodeoxyribonucleotide that exhibits a non-transferred transposon end sequence at its 5'-end, a transferred transposon end sequence at its 3'-end, and an intervening arbitrary sequence between the non-transferred transposon end sequence and the transferred transposon end sequence that is sufficiently long to allow intramolecular stem-loop formation, such that the transposon end portion can function in a transposition reaction. In some embodiments, the 5'-end of the hairpin transposon end composition has a phosphate group in the 5'-position of the 5'-nucleotide. In some embodiments, the intervening arbitrary sequence between the non-transferred transposon end sequence and the transferred transposon end sequence of a hairpin transposon end composition provides a tag (e.g., including one or more tag domains) for a particular use or application.

A "transposition reaction" is a reaction wherein one or more transposon ends are inserted into a target DNA at random sites or almost random sites. Essential components in a transposition reaction are a transposase and DNA oligonucleotides that exhibit the nucleotide sequences of the transposon end, including the transferred transposon end sequence and its complement, the non-transferred transposon end sequence, as well as other components needed to form a functional transposition complex.

As used herein, a "tag" refers to a non-target nucleic acid component, generally DNA, which provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA")." The tag can have one or more tag portions or tag domains.

As used herein, a "tag portion" or a "tag domain" means a portion or domain of a tag that exhibits a sequence for a desired intended purpose or application. One tag portion or tag domain is the "transposon end domain," which tag portion or tag domain exhibits the transferred transposon end sequence. In some embodiments wherein the transferred strand also exhibits one or more other nucleotide sequences 5'-of the transferred transposon end sequence, the tag also has one or more other "tag domains" in said 5'-portion, each of which tag domains is provided for any desired purpose. For example, some embodiments of the invention comprise or consist of a transposon end composition that comprises or consists of: (i) a transferred strand that exhibits one or more sequences 5'-of the transferred transposon end sequence that comprises or consists of a tag domain selected from among one or more of a an index tag domain (such as a sample index tag domain, or an unique molecular identifier (UMI) tag domain), an amplification tag domain, a restriction site tag domain, an amplification facilitating tag domain; and (ii) a non-transferred strand that exhibits the non-transferred transposon end sequence. The invention comprises embodiments of the method that use any one or more of said transposon end compositions.

As used herein, a "restriction site domain" or "restriction site tag" means a tag domain that exhibits a sequence for the purpose of facilitating cleavage.

As used herein, an "amplification tag domain" or "amplification tag", or an "amplification facilitating tag domain" or "amplification facilitating tag" means a tag domain that exhibits a sequence for the purpose of facilitating amplification of a nucleic acid to which said tag is appended. For example, in some embodiments, the amplification tag domain or the amplification facilitating tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction). In some embodiments, the amplification tag comprises about 9-30 nt, such as about 12-22 nt, or about 15 nt. In some embodiments, the amplification facilitating tag is a small fragment that participates in template-primer base-pairing, but confers less specificity compared to the priming site sequence (e.g., the 5'-end of the primer is less critical for primer annealing than the 3'-end). In some embodiments, the amplification facilitating tag comprises about 3-30 nt, such as about 4-22 nt, about 4-9 nt, or about 5 nt.

As used herein, a "sample index tag domain" or a "sample index tag" means a tag domain that exhibits a sequence that permits identification of a specific sample.

The names and descriptions of different tag domains are for convenience, such as to make it easier to understand and discuss the intended purposes and applications of the different portions or domains of the tag in different embodiments. However, these names and descriptions are not intended to limit the use or applications of the tag or of any of its tag domains in any way. Thus, any particular tag or tag domain can be used for any purpose in addition to, or in place of the intended or primary purpose or application. Also, one tag domain can comprise two or more other tag domains or one tag domain can provide the functions or purposes or applications of two or more different tag domains. Still further, the tag need not be described in terms of one or more different domains in order to be used for any particular purpose or application or function.

As used herein, the terms "amplify" or "amplified" "amplifying" as used in reference to a nucleic acid or nucleic acid reactions, refer to in vitro methods of making copies of a particular nucleic acid, such as a target nucleic acid, or a tagged nucleic acid produced, for example, by an embodiment of the present invention. Numerous methods of amplifying nucleic acids are known in the art, and amplification reactions include polymerase chain reactions, ligase chain reactions, strand displacement amplification reactions, rolling circle amplification reactions, transcription-mediated amplification methods such as NASBA (e.g., U.S. Pat. No. 5,409,818), loop mediated amplification methods (e.g., "LAMP" amplification using loop-forming sequences, e.g., as described in U.S. Pat. No. 6,410,278). The nucleic acid that is amplified can be DNA comprising, consisting of, or derived from DNA or RNA or a mixture of DNA and RNA, including modified DNA and/or RNA. The products resulting from amplification of a nucleic acid molecule or molecules (i.e., "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification.

The terms "anneal" or "hybridize" and "annealing" or "hybridization" refer to the formation of complexes between nucleotide sequences that are sufficiently complementary to form complexes via Watson-Crick base pairing. With respect to the present invention, nucleic acid sequences that are "complementary to" or "complementary with" or that "hybridize" or "anneal" to or with each other should be capable of forming or form "hybrids" or "complexes" that are sufficiently stable to serve the intended purpose. It is not required that every nucleic acid base within a sequence exhibited by one nucleic acid molecule is capable of base-pairing or is paired with or is complexed with every nucleic acid base within a sequence exhibited by a second nucleic acid molecule in order for the two nucleic acid molecules or the respective sequences exhibited therein to be "complementary" or "annealed" or "hybridized" to or with each other.

As used herein, the terms "complementary" or "complementarity" are used in reference to a sequence of nucleotides related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon hybridization of nucleic acids.

The term "homology" refers to a degree of complementarity of one nucleic acid sequence with another nucleic acid sequence. There may be partial homology or complete homology (i.e., complementarity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks complementarity or that has only a low degree of complementarity (e.g., less than about 30% complementarity). In the case in which specific binding is low or non-existent, the probe will not hybridize to a nucleic acid target. When used in reference to a double-stranded nucleic acid sequence such as a cDNA or a genomic clone, the term "substantially homologous" refers to any oligonucleotide or probe which can hybridize to either or both strands of the double-stranded nucleic acid sequence under conditions of low stringency as described herein.

As used herein, the terms "annealing" or "hybridization" are used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol or betaine), the molarity of the hybridizing strands and the G:C content of the nucleic acid strands.

As used herein, a "DNA fragment" means a portion or piece or segment of a longer DNA molecule that is cleaved from or released or is broken from the longer DNA molecule such that it is no longer attached to the parent molecule, or a ssDNA molecule that is a complementary copy of only a portion of the longer DNA molecule, in which case, the complementary copy is synthesized by using a DNA polymerase to extend a primer that anneals to and uses the longer DNA molecule as a template. A DNA fragment can be double-stranded (a "dsDNA fragment") or single-stranded (a "ssDNA fragment"), and the process of generating DNA fragments from the target DNA is referred to as "fragmenting" the target DNA. In some embodiments, the method is used to generate a "DNA fragment library" comprising a collection or population of tagged DNA fragments.

As used herein, a "DNA fragment library," "DNA library," or a "library of DNA fragments" means a collection or population of tagged DNA fragments (e.g., di-tagged (both 5' and 3' tagged) DNA fragments or tagged circular ssDNA fragments) generated from target DNA, wherein the combination of the tagged DNA fragments in the collection or population exhibits sequences that are qualitatively and/or quantitatively representative of the sequence of the target DNA from which the tagged DNA fragments were generated, and wherein the tagged DNA fragments that are in the collection or population have not been selected for or selected against by intentionally using a method that either includes or excludes tagged DNA fragments based on the nucleotide or sequence composition of the target DNA. For a variety of reasons, it is possible that a DNA fragment library may not contain a tagged DNA fragment representing every sequence which is exhibited by the target DNA. For example, in some embodiments, the tagged DNA fragment library may not contain tagged DNA fragments that exhibit sequences of the ends of a target DNA comprising linear dsDNA (e.g., due to a low frequency of insertion of two transposon end compositions into the end portions of the target DNA). Generally, a lower frequency or lack of tagged DNA fragments that exhibit sequences of certain portions or regions of the target DNA is acceptable for the intended purpose or application. However, the invention also comprises embodiments for those situations when it is considered important or desirable for a particular purpose or application to generate a DNA fragment library wherein there is a higher probability that the tagged DNA fragments exhibit every sequence which is exhibited by the target DNA from which the fragments were generated. Still further, in some cases the probability that the DNA fragment library will contain a tagged DNA fragment that exhibits every sequence of the target DNA will be increased if more molecules of target DNA are present in the transposition reaction step of the method, thereby generating more molecules of 5'-tagged DNA fragments using the method. Thus, still another method for increasing the probability that a DNA fragment library will contain a tagged DNA fragment that exhibits every sequence which is exhibited by the target DNA is to amplify the target DNA and then use the amplified target DNA in place of the target DNA for generating the DNA fragment library. In still other embodiments wherein target DNA comprises dsDNA prepared from RNA using a reverse transcription reaction, the amount of target DNA is amplified by amplifying the RNA prior to converting it to dsDNA using the reverse transcription step. Some methods for amplification of RNA and DNA molecules that can be used for providing amplified target DNA are disclosed herein. However, the invention is not limited with respect to the method used for amplifying the target DNA. In some embodiments, the target DNA is amplified using one of the methods disclosed herein, whereas in some other embodiments, another method known in the art is used.

As used herein, a "DNA polymerase" refers to an enzyme that catalyzes the polymerization of deoxyribonucleotides into a DNA strand. DNA polymerases comprise "template-dependent DNA polymerases," which require a template nucleic acid to determine the order in which deoxyribonucleotides are added in the polymer, or they may be "template-independent" such that they catalyze polymerization without reference to a template sequence.

A "DNA-dependent DNA polymerase" is an enzyme that synthesizes a complementary DNA ("cDNA") copy by extension of a primer that is annealed to a DNA template. Some DNA-dependent DNA polymerases may also synthesize a complementary DNA copy from an RNA template, a process that is also referred to as "reverse transcription." DNA polymerases that can reverse-transcribe can also be referred to as a "reverse transcriptases."

In general, "cDNA" or a "cDNA molecule" refers to "complementary DNA" that is synthesized by RNA-dependent DNA polymerase- or reverse transcriptase-catalyzed extension of a primer that anneals to an RNA molecule of interest using at least a portion of the RNA molecule of interest as a template (which process is also called "reverse transcription"). The cDNA molecules synthesized are "homologous to" or "base pair with" or "form a complex with" at least a portion of the template.

In addition to synthesizing DNA polymers, DNA polymerases may comprise other features or activities. For example, a DNA polymerase may be characterizes as having or lacking 5' to 3' exonuclease activity (also referred to a 5' exonuclease or 5' nuclease activity), 3' to 5' exonuclease activity, strand displacement activity, and they may be characterized with respect to the degree they are processive or distributive, as discussed in more detail below.

Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." The template for strand displacement DNA synthesis can be a linear or circular single-stranded DNA (ssDNA) or double-stranded DNA (dsDNA). If the DNA template is a single-stranded circle, primed DNA synthesis proceeds around and around the circle, with continual displacement of the strand ahead of the replicating strand, a process called "rolling circle replication." Rolling circle replication results in synthesis of tandem copies of the circular template. In general, it is preferred that a DNA-template-specific DNA polymerase used for a method of the invention efficiently synthesizes DNA of a suitable length for the intended purpose without "falling off" of the template (or terminating synthesis of the DNA), which is referred to as the enzyme's processivity. The capability of a DNA polymerase to strand displace can be readily determined using the polymerase in a rolling circle replication assay as described by Fire and Xu (Proc. Natl. Acad. Sci. USA 92: 4641-4645, 1995). Strand displacement and DNA polymerase processivity can also be assayed using methods described in Kong et al. (J. Biol. Chem. 268: 1965-1975, 1993). Terminal transferase is also defined as a DNA polymerase herein, which DNA polymerase is used as a composition in some embodiments of the kits and methods of the present invention. Terminal transferase is preferred in some embodiments because it catalyzes template-independent addition of dNTPs to the 3'-hydroxyl termini of DNA.

Some embodiments comprise a method that uses a DNA polymerase composition that has 5'-to-3' exonuclease activity to release a nucleotide that is labeled with a detectable moiety (e.g., a moiety comprising a visible, fluorescent, chemiluminescent, or other detectable molecule) as a means for assaying DNA polymerization, and thereby, detecting and/or quantifying the presence in the sample of the nucleic acid molecule that serves as the template (e.g., in a manner similar to the TaqMan® assays of Applied Biosystems, Inc.). In some embodiments, the present invention comprises a DNA polymerase composition that lacks 5'-to-3' exonuclease activity.

Some embodiments comprise a method that uses a DNA polymerase composition that lacks 5'-to-3' exonuclease activity. For example, in some embodiments, a DNA polymerase composition that lacks 5'-to-3' exonuclease activity is used for DNA sequencing. For example, in some other embodiments, a DNA polymerase composition that lacks 5'-to-3' exonuclease activity is used for whole genome amplification.

In some embodiments, the present invention comprises a DNA polymerase composition that has 5'-to-3' exonuclease activity. In some embodiments (e.g., wherein a DNA polymerase is used, in addition to a template-dependent ligase), the method uses a DNA polymerase composition that lacks 5' nuclease activity (including both 5'-to-3' exonuclease and 5' structure-dependent nuclease activity). For example, in some other embodiments, a DNA polymerase composition that lacks 5'-to-3' exonuclease activity is used for to fill a gap. Thus, in some embodiments of methods or kits, the present invention comprises a DNA polymerase composition that lacks 5' nuclease activity. However, a DNA polymerase composition that has 5' nuclease activity to release a nucleotide or an oligonucleotide that is labeled with a detectable moiety (e.g., a moiety comprising a visible, fluorescent, chemiluminescent, or other detectable molecule) as a means for assaying DNA polymerization, and thereby, detecting and/or quantifying the presence in the sample of the nucleic acid molecule that serves as the template (e.g., in a manner similar to the TaqMan® assays of Applied Biosystems, Inc.) could be used for quantifying DNA molecules generated using a method of the invention.

Examples of strand-displacing DNA polymerases that can be used include, but are not limited to, RepliPHI™ phi29 DNA polymerase, DisplaceAce™ DNA polymerase, rGka DNA polymerase, SequiTherm™ DNA polymerase, Taq DNA polymerase, Tfl DNA polymerase, and MMLV reverse transcriptase (all available from EPICENTRE Biotechnologies, Madison, Wis., USA). In some embodiments, a blend of a DNA polymerase that lacks 3'-to-5' exonuclease proofreading activity with a DNA polymerase that has this activity, such as FAILSAFE™ DNA polymerase is used as the strand-displacing DNA polymerase. The enzyme blend is useful in some embodiments because it exhibits improved fidelity during DNA synthesis (i.e., it synthesizes DNA with fewer nucleotides that are not complementary to the template). Fidelity and/or error rates of many DNA polymerases under particular conditions are known, as are methods for measuring fidelity (e.g., by sequencing).

In general, it is desirable in a strand-displacement amplification method of the present invention that the amount of strand-displacing DNA polymerase used in the method is as high as possible without inhibiting or adversely affecting the reaction. For example, REPLIPHI™ phi29 DNA polymerase (EPICENTRE) can be used at about one microgram of protein in a 20-microliter reaction and DISPLACE™ DNA polymerase (EPICENTRE) can be used at about 50 units to about 300 units in a 50-microliter reaction. Since definitions for units vary for different DNA polymerases and even for similar DNA polymerases from different vendors or sources, and also because the activity for each enzyme varies at different temperatures and under different reaction conditions, it is desirable to optimize the amount of strand-displacing DNA polymerase and reaction conditions for each DNA template and primer used.

Strand displacement can be facilitated through the use of a strand displacement factor, such as helicase, but since a variety of DNA polymerases can be used for the present invention, such a strand displacement factor is not usually required. It is considered that any DNA polymerase that can perform rolling circle replication in the presence of a strand displacement factor is suitable for use in embodiments of the invention that comprise strand displacement even if the DNA polymerase does not perform rolling circle replication in the absence of such a factor. Strand displacement factors that permit rolling circle replication include, but are not limited to, BMRF1 polymerase accessory subunit (Tsurumi et al., J. Virology, 67: 7648-7653, 1993), adenovirus DNA-binding protein (Zijderveld and van der Vliet, J. Virology, 68: 1158-1164, 1994), herpes simplex viral protein ICP8 (Boehmer and Lehman, J. Virology, 67: 711-715, 1993); Skaliter and Lehman, Proc. Natl. Acad. Sci. USA, 91: 10,665-10,669, 1994), single-stranded DNA binding proteins (SSB; Rigler and Romano, J. Biol. Chem., 270: 8910-8919, 1995), and calf thymus helicase (Siegel et al., J. Biol. Chem., 267: 13,629-13,635, 1992), all of which are incorporated herein by reference.

As used herein, "target DNA" refers to any dsDNA of interest that is subjected to transposition, e.g., for generating a library of tagged DNA fragments (e.g., 5'- and 3'-tagged or di-tagged linear ssDNA or dsDNA fragments or tagged circular ssDNA fragments).

"Target DNA" can be derived from any in vivo or in vitro source, including from one or multiple cells, tissues, organs, or organisms, whether living or dead, or from any biological or environmental source (e.g., water, air, soil). For example, in some embodiments, the target DNA comprises or consists of eukaryotic and/or prokaryotic dsDNA that originates or that is derived from humans, animals, plants, fungi, (e.g., molds or yeasts), bacteria, viruses, viroids, *mycoplasma*, or other microorganisms. In some embodiments, the target DNA comprises or consists of genomic DNA, subgenomic DNA, chromosomal DNA (e.g., from an isolated chromosome or a portion of a chromosome, e.g., from one or more genes or loci from a chromosome), mitochondrial DNA, chloroplast DNA, plasmid or other episomal-derived DNA (or recombinant DNA contained therein), or double-stranded cDNA made by reverse transcription of RNA using an RNA-dependent DNA polymerase or reverse transcriptase to generate first-strand cDNA and then extending a primer annealed to the first-strand cDNA to generate dsDNA. In some embodiments, the target DNA comprises multiple dsDNA molecules in or prepared from nucleic acid molecules (e.g., multiple dsDNA molecules in or prepared from genomic DNA or cDNA prepared from RNA in or from a biological (e.g., cell, tissue, organ, organism) or environmental (e.g., water, air, soil, saliva, sputum, urine, feces) source. In some embodiments, the target DNA is from an in vitro source. For example, in some embodiments, the target DNA comprises or consists of dsDNA that is prepared in vitro from single-stranded DNA (ssDNA) or from single-stranded or double-stranded RNA (e.g., using methods that are well-known in the art, such as primer extension using a suitable DNA-dependent and/or RNA-dependent DNA polymerase (reverse transcriptase). In some embodiments, the target DNA comprises or consists of dsDNA that is prepared from all or a portion of one or more double-stranded or single-stranded DNA or RNA molecules using any methods known in the art, including methods for: DNA or RNA amplification (e.g., PCR or reverse-transcriptase-PCR (RT-PCR), transcription-mediated amplification methods, with amplification of all or a portion of one or more nucleic acid molecules); molecular cloning of all or a portion of one or more nucleic acid molecules in a plasmid, fosmid, BAC or other vector that subsequently is replicated in a suitable host cell; or capture of one or more nucleic acid molecules by hybridization, such as by hybridization to DNA probes on an array or microarray (e.g., by "sequence capture"; e.g., using kits and/or arrays from ROCHE NIMBLEGEN, AGILENT, or FEBIT).

In some embodiments, "target DNA" means dsDNA that is prepared or modified (e.g., using various biochemical or molecular biological techniques) prior to being used for generating a library of tagged DNA fragments (e.g., 5'- and 3'-tagged or di-tagged linear ssDNA or dsDNA fragments or tagged circular ssDNA fragments). For example, in some events the representation of next-generation sequence data from the ends of target DNA comprising dsDNA molecules with a size of less than 10 Kb is low compared to the representation of sequence data from the middle of that target DNA. Without being bound by theory, one possible explanation for this observation is that the probability of finding DNA fragments with two transposon end compositions inserted in opposite orientations at the ends of a linear dsDNA molecule is lower than the probability of finding DNA fragments with two transposon end compositions inserted in opposite orientations in the middle of the linear dsDNA molecule. Thus, in some embodiments, in order to generate libraries of di-tagged DNA fragments or tagged circular DNA fragments that better represent the end sequences, the method further comprises providing target DNA for use in the method comprising dsDNA (e.g., double-stranded genomic DNA or cDNA prepared from RNA, such as mRNA) that already has a tag on the 5' and/or 3' end. For example, in some embodiments, the target DNA comprises double-stranded cDNA that is prepared from RNA by: synthesizing first-strand cDNA by extending a first-strand cDNA synthesis primer that has a 3'-portion and a 5'-portion, wherein the 3'-portion is complementary to the 3'-end portion of the RNA and the 5'-portion comprises a first tag, then joining a second tag to the 3'-end of the first-strand cDNA using a terminal tagging oligonucleotide and a DNA polymerase as described elsewhere herein, and then using a DNA polymerase to synthesize double-stranded cDNA by extending a second-strand cDNA synthesis primer that anneals to the second tag. Alternatively, in some other embodiments, in order to generate libraries of di-tagged DNA fragments that better represent the end sequences, the target DNA used in the method for generating di-tagged DNA fragments or tagged circular DNA fragments comprises circular dsDNA that is prepared by intramolecular ligation of linear dsDNA (e.g., that is prepared by intramolecular ligation of double-stranded genomic DNA or of double-stranded cDNA prepared from RNA, such as mRNA). Thus, in some embodiments, the method further comprises: ligating the linear dsDNA using a ligase (e.g., T4 DNA ligase) to generate circular dsDNA for use as target DNA in the method. In some embodiments of the method comprising generating circular dsDNA for use as target DNA by ligating linear dsDNA, the linear dsDNA is treated with T4 DNA polymerase and T4 polynucleotide kinase (e.g., using the END-It™ DNA End Repair Kit (EPICENTRE Biotechnologies, Madison, Wis., USA) prior to the ligation step in order to make the ends blunt and phosphorylate the 5'-ends.

The term "sample" as used herein relates to a material or mixture of materials, typically containing one or more analytes of interest. In one embodiment, the term as used in its broadest sense, refers to any plant, animal, bacterial, or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "specifically binds" refers to, with respect to an antigen, the preferential association of an antibody or other ligand, in whole or part, with a specific polypeptide, such as a specific protein bound to chromatin DNA, for example a transcription factor. A specific binding agent binds substantially only to a defined target. It is recognized that a minor degree of non-specific interaction may occur between a molecule, such as a specific binding agent, and a non-target polypeptide. Nevertheless, specific binding can be distinguished as mediated through specific recognition of the antigen. Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a target polypeptide, such as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

The term "antibody" or "antibody moiety" is used in the broadest sense and encompasses various antibody structures, including but not limited to monoclonal antibodies, multispecific antibodies (e.g., bispecific antibodies), full-length antibodies and antigen-binding fragments thereof, so long as they exhibit the desired antigen-binding activity.

A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\epsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

An "effective amount" of a composition as disclosed herein, is an amount sufficient to carry out a specifically stated purpose. An "effective amount" can be determined empirically and by known methods relating to the stated purpose.

The term "duplex," or "duplexed," as used herein, describes two complementary polynucleotide region that are base-paired, i.e., hybridized together.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

A "plurality" contains at least 2 members. In certain cases, a plurality may have at least about 2, at least about 5, at least about 10, at least about 100, at least about 100, at least about 10,000, at least about 100,000, at least about $10^6$, at least about $10^7$, at least about $10^8$, or at least about $10^9$ or more members.

The term "epitope" or "antigenic determinant" as used herein refers to that portion of a molecule that is recognized by a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "genomic" as used herein refers to source any nuclear material related to a set of chromosomes derived from a biological cell (i.e., as opposed to a set of mitochondrial chromosomes). For example, such nuclear material may include, but is not limited to, DNA, RNA, or proteins (i.e., for example, histones).

The term "cross-linking agent" as used herein refers to a chemical agent or even light, that facilitates the attachment of one molecule to another molecule. Cross-linking agents can be protein-nucleic acid cross-linking agents, nucleic acid-nucleic acid cross-linking agents, and/or protein-protein cross-linking agents. Examples of such agents are known in the art. In some embodiments, a cross-linking agent is a reversible cross-linking agent. In some embodiments, a cross-linking agent is a non-reversible cross-linking agent.

The term "DNA sequencing" means the process of determining the nucleotide order of a given DNA molecule. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array-based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences. Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour.

The term "barcode sequence," "experimental index," or "molecular barcode," as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

The term "isolated chromatin," as used herein, refers to a source of chromatin that is caused to be made available. Isolated nuclei (which can be lysed to produce chromatin) as well as isolated chromatin (i.e., the product of lysed nuclei) are both considered types of chromatin isolated from a population of cells.

The term "transcription factor", as used herein, refers to any polypeptide that may act by itself or in combination with at least one other polypeptide to regulate gene expression levels. The term includes, but is not limited to, polypeptides that directly bind DNA sequences. Transcription factors can either increases or suppress expression levels. Examples of transcription factors include, but are not limited to Myc/Max, AP-1 (Jun, Fos, ATF), CREB, SMAD, HIF, ETS, ERG, ELK, STAT, estrogen receptor (ER), androgen receptor (AR), glucocorticoid receptor (GR), progesterone receptor (PR), NFκB, p53, OCT, SOX and PAX. The transcription factor may be a transcription factor identified by sequence analysis or a naturally-occurring reading frame sequence that has not been previously characterized as a transcription factor. The polypeptide may also be an artificially generated or chemically or enzymatically modified polypeptide.

The term "region," as used herein, refers to a contiguous length of nucleotides in a genome of an organism. A chromosomal region may be in the range of 1 bp to the length of an entire chromosome. In some instances, a region may have a length of at least 200 bp, at least 500 bp, at least 1 kb, at least 10 kb or at least 100 kb or more (e.g., up to 1 Mb or 10 Mb or more). The genome may be from any eukaryotic organism, e.g., an animal or plant genome such as the genome of a human, monkey, rat, fish or insect.

The term "epigenetic map," as used herein, refers to any representation of epigenetic features, e.g., sites of nucleosomes, nucleosome-free regions, histone modification patterns, binding sites for transcription factors, etc. A map can be physically displayed, e.g., on a computer monitor.

The term "chromatin accessibility," as used herein, refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins).

The term "nucleosome-depleted fragments," or "nucleosome-depleted region," as used herein, refers to fragments of genomic DNA or a genomic region that are relatively depleted or devoid of nucleosomes, i.e., between nucleosomes, actively transcribed promoter.

The term "sequence read abundance," as used herein, refers to the number of times a particular sequence or nucleotide is observed in a collection of sequence reads.

The term "DNA binding protein occupancy," as used herein, refers to whether a binding site for a sequence specific DNA binding protein (e.g., a binding site for a transcription factor) is occupied by the DNA binding protein. DNA binding protein occupancy can be measured quantitatively or qualitatively.

The term "nucleosome occupancy," as used herein, refers to whether a fragment of genomic DNA or a genomic region is occupied by nucleosomes. Nucleosome occupancy can be measured quantitatively or qualitatively.

The term "histone modification pattern" as used herein refers to any recognizable changes on a chromatin map that signifies histone modifications associated with gene expression. For example, both acetylation and methylation of histones are believed associated with transcriptional activity, but the former occurs predominantly at the beginning of genes whereas the latter can occur throughout transcribed regions. Most notably, specific methylation events are associated with the beginning, middle and end of actively transcribed genes.

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, enhancers, etc.

The term "sequence identity" or "sequence similarity" refers to the identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

The term "mapping information," as used herein, refers to assembling experimentally-obtained information about an area to a physical map of the area.

The term "chromatin immunoprecipitation (ChIP) assay" is well known to a skilled person, and preferably comprises at least the following steps: (i) preparation of a liquid sample comprising chromatin to be analyzed from cells; (ii) immunoprecipitation of the chromatin in the liquid sample onto the matrix using an antibody; and (iii) DNA recovery from the precipitated chromatin; and (iv) DNA analysis.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Transposase-Assisted Chromatin and Nucleic Acids Indexing

The ChIP method allows studying genome-wide DNA-protein interactions. It contributed substantially to our understanding of chromatin organization, histone modification as well as transcription factor binding patterns and their influence on gene regulation in health and disease; see e.g. Nature (2012) 489, pp. 57-74, or Ernst et al. (2011) Nature 473, pp. 43-49. However, ChIP remains a relatively tedious protocol especially when applied to low-input sample (see e.g. Greenleaf, W. J. (2014) Methods). The standard ChIP-seq protocol comprises the steps of fixation of cells, cell lysis, sonication of chromatin and immunoprecipitation with a specific antibody bound to beads. Reverse-crosslinking is followed by purification of ChIP DNA, which is then subjected to library preparation (for next generation sequencing) in a multi-step and laborious procedure comprising: (i) end-repair of the purified DNA sequences to generate blunt-end double-stranded DNA fragments with a phosphorylated 3' end; (ii) addition of an A-overhang; (iii) ligation of adaptors that have a complementary T-overhang to the double-stranded and end-repaired ChIP-DNA fragments with A-overhang. The adapters allow amplification of the DNA fragments, which ensures sufficient amount of fragments for quality control and subsequent sequencing, and it also prepares the fragments for the sequencing procedure by introduction of flow-cell ends for cluster generation and barcode sequences to multiplex sequencing experiments; and (iv) size selection; wherein each step of the library preparation is followed by a purification step. The classical method comes with several limitations: (i) 5-10 ng of input material is typically needed to generate libraries which cannot be recovered from ChIPs on low amounts of cells. Hence, the recommended amount of cells for a ChIP-seq experiment is in the range of $10^6$ cells; (ii) the library procedure relies on several enzymatic reactions and DNA purifications, which make library generation a relatively laborious procedure. Imperfect enzymatic reactions as well as DNA purifications also lower the amount of recovered library fragments, which explains the high input requirements; (iii) adapters can self-ligate and need to be excluded from amplification and sequencing. Hence, a size-selection is necessary to select against excess adapters and adapter-dimers; (iv) it is difficult to normalize and quantitatively compare across multiple samples/ChIP experiments, because different samples are individually handled among every steps of the traditional ChIP-seq protocol, resulting in variances starting from cell homogenization, chromatin fragmentation, immunoprecipitation, to each individual steps of library preparation; (v) high risk of over-fragmentation leading to small fragments; (vi) tedious, complex, and time-consuming.

All of the embodiments of the methods of the present invention disclosed herein use an in vitro or in vivo transposition reaction to simultaneously break a chromatin (or target DNA) into fragments and join a tag to the 5'-end of each fragment. Since all of the methods are related, unless otherwise specifically stated with respect to a particular embodiment, a method that is present herein with respect to one embodiment can also be used with another embodiment described herein. All of the embodiments of the methods disclosed herein that use an in vitro or in vivo transposition reaction can be performed by assembling the reaction using either separate transposase and transposon end compositions or a single transposome complex formed between the transposase and the transposon end composition. Therefore, it will be understood that any method that describes the use of a transposase and a transposon end composition could also use a transposome complex made from the transposase and the transposon end composition (e.g., pre-incubation), and any method that describes the use of a transposome complex could also use the separate transposase and a transposon end compositions of which the transposome complex is composed. This is illustrated by following descriptions of general methods of the invention.

In some embodiments, there is provided a method of analyzing the binding sequences on a chromosome to which a protein of interest binds, comprising: (a) randomly inserting a plurality of transposon end compositions comprising transposon end described herein into the chromatin or double-stranded nucleic acid fragments thereof (e.g., chromatin DNA) in the presence of a transposase (e.g., Tn5); (b) subjecting the double-stranded nucleic acid fragments inserted with transposon end compositions comprising transposon end to immunoprecipitation using a binding agent (e.g., an antibody or fragments thereof) specifically recognizing the protein of interest (e.g., for use in next-generation sequencing); and (c) analyzing the nucleic acid fragment sequences to which the protein of interest binds. In some embodiments, the chromatin sample is cross-linked. In some embodiments, the chromatin sample is not cross-linked (native chromatin). In some embodiments, the method comprises: incubating the chromatin (native or cross-linked) in an in vitro or in vivo transposition reaction with at least one transposase and a transposon end composition with which the transposase forms a transposome complex, the transposon end composition comprising (i) a transferred strand that exhibits a transferred transposon end sequence and, optionally, an additional sequence (e.g., sample index tag, restriction site tag, amplification tag) 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a transposon end composition tag comprising or consisting of the transferred strand to the 5' end of a nucleotide in the target DNA (e.g., chromatin DNA), thereby fragmenting the chromatin (or chromatin DNA) and generating a population of annealed 5'-tagged chromatin (or chromatin DNA) fragments, each of which has the transposon end composition tag on the 5'-end. In some embodiments, when tagmenting the chromatin with the transposon end composition and transposase, the double-stranded chromatin DNA is tagged on one strand with 5'-tagged transferred strand, and on the other strand also with a 5'-tagged transferred strand. However, during denaturing step, these 5' dual-tagged chromatin dsDNA fragments are denatured into two 5'-tagged ssDNA, similar to the embodiments where chromatin is only tagmented with a 5'-tag. The 5'-tagged chromatin (or chromatin DNA) is immunoprecipitated with a binding agent (e.g., an antibody or fragments thereof) specifically recognizing the protein of interest, then reverse-crosslinked and denatured at high temperature, resulting in 5'-tagged ssDNA fragments; then the 3'-ends of the 5'-tagged DNA fragments are joined to the 5' tag (e.g., self-circularization by CircLigase), thereby generating a library of tagged circular ssDNA fragments. These tagged circular ssDNA fragments can be subjected to further manipulation (e.g., amplification, generating sequencing library for sequencing). In some embodiments, the tagged circular ssDNA fragments are linearized by cleaving at a restriction site (e.g., using USER enzyme to cleave deoxyuridine (U)) within the 5'-transposon end composition tag, resulting in 5'- and 3'-tagged ssDNA fragments (or "di-tagged ssDNA fragments", with a portion of the transposon end composition tag on the 5' end, and the other portion of the transposon end composition tag on the 3' end). These di-tagged ssDNA fragments can be subjected to further manipulation (e.g., amplification, generating sequencing library for sequencing). In some embodiments, after isolating the 5'-transposon end composition tagged chromatin (or chromatin DNA) captured by immunoprecipitating binding agent, and before reverse-crosslinking and denaturing, the captured 5'-tagged chromatin (or chromatin DNA) is subjected to an additional exonuclease (e.g., Exo III) digestion step to digest the tagged chromatin DNA up to the binding boundary of the protein of interest (e.g. transcription factor). In some embodiments, the transposon end compositions comprise sample index tag on the 5' portion of the transferred strand. Thus, different biological samples can be tagmented with different transposon end compositions carrying different sample index, then pooled together for later immunoprecipitation. In some embodiments, before randomly inserting the transposon end compositions (tagmenting), the sample chromatin is pre-fragmented, e.g. mildly sheared by sonication.

In some embodiments, there is provided a method of analyzing the binding sequences on a chromosome to which a protein of interest binds, comprising: (a) immunoprecipitating the chromatin using a binding agent (e.g., an antibody or fragments thereof) specifically recognizing the protein of interest; (b) randomly inserting a plurality of transposon end compositions comprising transposon end described herein into the chromatin or double-stranded nucleic acid fragments thereof (e.g., chromatin DNA) in the presence of a transposase (e.g., Tn5); (c) analyzing the nucleic acid fragment sequences to which the protein of interest binds. In some embodiments, the chromatin sample is cross-linked. In some embodiments, the chromatin sample is not cross-linked (native chromatin). In some embodiments, before ChIP, the sample chromatin is pre-fragmented, e.g. mildly sheared by sonication. In some embodiments, the binding agent bound chromatin is mildly fragmented (e.g., mildly sonication to avoid disrupting the interaction between the binding agent and chromatin) before inserting transposon end compositions. Since different samples are ChIPed first then tagmented with the transposon end compositions in these embodiments, different sample (if without other distinguishing labeling) may not be pooled together during ChIP, but can be differentially tagmented with transposon end compositions comprising different sample index tags, then pooled together for later DNA recovery and library preparation. In some embodiments, the method comprises: incubating the chromatin (native or cross-linked) bound by immunoprecipitating binding agent (e.g., an antibody or fragments thereof) in an in vitro transposition reaction with at least one transposase and a transposon end composition with which the transposase forms a transposome complex, the transposon end composition comprising (i) a transferred strand that exhibits a transferred transposon end sequence and, optionally, an additional sequence (e.g., sample index tag, restriction site tag, amplification tag) 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a transposon end composition tag comprising or consisting of the transferred strand to the 5' end of a nucleotide in the target DNA (e.g., chromatin DNA), thereby fragmenting the binding agent-bound chromatin (or chromatin DNA) and generating a population of annealed 5'-tagged binding agent-bound chromatin (or chromatin DNA) fragments, each of which has the transposon end composition tag on the 5'-end. In some embodiments, when tagmenting the binding agent-bound chromatin with the transposon end composition and transposase, the double-stranded chromatin DNA is tagged on one strand with 5'-tagged transferred strand, and on the other strand also with a 5'-tagged transferred strand. However, during denaturing step, these 5' dual-tagged binding agent-bound chromatin dsDNA fragments are denatured into two 5'-tagged ssDNA, similar to the embodiments where chromatin is only tagmented with a 5'-tag. The 5'-tagged binding agent-bound chromatin (or chromatin DNA) is isolated, e.g. recovering chromatin-antibody-bead complex, then reverse-crosslinked and denatured at high temperature, resulting in 5'-tagged ssDNA fragments; then the 3'-ends of the 5'-tagged DNA fragments are joined to the 5' tag (e.g., self-circularization by CircLigase), thereby generating a library of tagged circular ssDNA fragments. These tagged circular ssDNA fragments can be subjected to further manipulation (e.g., amplification, generating sequencing library for sequencing). In some embodiments, the tagged circular ssDNA fragments are linearized by cleaving at a restriction site (e.g., using USER enzyme to cleave deoxyuridine (U)) within the 5'-transposon end composition tag, resulting in 5'- and 3'-tagged ssDNA fragments (or "di-tagged ssDNA fragments", with a portion of the transposon end composition tag on the 5' end, and the other portion of the transposon end composition tag on the 3' end). These di-tagged ssDNA fragments can be subjected to further manipulation (e.g., amplification, generating sequencing library for sequencing). In some embodiments, after isolating the 5'-tagged chromatin (or chromatin DNA) captured by immunoprecipitating binding agent, and before reverse-crosslinking and denaturing, the captured 5'-transposon end composition tagged chromatin (or chromatin DNA) is subjected to an additional exonuclease (e.g., Exo III) digestion step to digest the tagged chromatin DNA up to the binding boundary of the protein of interest (e.g. transcription factor).

In some embodiments, there is provided a method of fragmenting (e.g., tagmenting) chromatin or naked dsDNA, comprising randomly inserting a plurality of transposon end compositions comprising transposon end described herein into the chromatin or naked dsDNA in the presence of a transposase (e.g., Tn5). In some embodiments, the chromatin is cross-linked. In some embodiments, the chromatin sample is not cross-linked (native chromatin). In some embodiments, the method comprises: incubating the chromatin (native or cross-linked) or naked dsDNA in an in vitro or in vivo transposition reaction with at least one transposase and a transposon end composition with which the transposase forms a transposome complex, the transposon end composition comprising (i) a transferred strand that exhibits a transferred transposon end sequence and, optionally, an additional sequence (e.g., sample index tag, restriction site tag, amplification tag) 5'-of the transferred transposon end sequence, and (ii) a non-transferred strand that exhibits a sequence that is complementary to the transferred transposon end sequence, under conditions and for sufficient time wherein multiple insertions into the chromatin or naked dsDNA occur, each of which results in joining of a transposon end composition tag comprising or consisting of the transferred strand to the 5' end of a nucleotide in the chromatin or naked dsDNA, thereby fragmenting the chromatin (or dsDNA) and generating a population of annealed 5'-tagged chromatin (or 5'-tagged dsDNA) fragments, each of which has the transposon end composition tag on the 5'-end. In some embodiments, when tagmenting the chromatin or naked dsDNA with the transposon end composition and transposase, the double-stranded DNA (chromatin DNA or naked DNA) is tagged on one strand with 5'-tagged transferred strand, and on the other strand also with a 5'-tagged transferred strand. However, during a denaturing step, these 5' dual-tagged chromatin dsDNA fragments (or 5' dual-tagged dsDNA) are denatured into two 5'-tagged ssDNA, similar to the embodiments where chromatin (or naked dsDNA) is only tagmented with a 5'-tag. These 5'-tagged chromatin (or chromatin DNA) fragments can be subjected to any desired purposes or proper methods described herein. Similarly, the 5'-tagged naked dsDNA fragments can also be subjected to any desired purposes or proper methods described herein.

For example, in one embodiments, there is provided a method of preparing sequencing library starting from ChIPed DNA, input DNA, dsDNA, or any nucleic acid (e.g., RNA can be reverse transcribed and made into dsDNA), comprising contacting the dsDNA sample with transposon end compositions comprising transposon end described herein in the presence of a transposase (e.g., Tn5), thus inserting the transposon end compositions into the dsDNA sample, generating nucleic acid fragments. The transposon end composition comprises (i) a transferred strand that exhibits a transferred transposon end sequence and, optionally, an additional sequence (e.g., sample index tag, restriction site tag, amplification tag) 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a transposon end composition tag comprising or consisting of the transferred strand to the 5' end of a nucleotide in the target DNA, thereby fragmenting the target DNA and generating a population of annealed 5'-tagged dsDNA fragments, each of which has the transposon end composition tag on the 5'-end. In some embodiments, when tagmenting the dsDNA with the transposon end composition and transposase, the double-stranded DNA is tagged on one strand with 5'-transposon end composition tagged transferred strand, and on the other strand also with a 5'-tagged transferred strand. However, during a later denaturing step, these 5' dual-tagged dsDNA fragments are denatured into two 5'-tagged ssDNA, similar to the embodiments where target DNA is only tagmented with a 5'-transposon end composition tag. The 5'-tagged dsDNA fragments are denatured at high temperature, resulting in 5'-tagged ssDNA fragments; then the 3'-ends of the 5'-tagged DNA fragments are joined to the 5' tag (e.g., self-circularization by CircLigase), thereby generating a library of tagged circular ssDNA fragments. These tagged circular ssDNA fragments can be subjected to further manipulation (e.g., amplification, generating sequencing library for sequencing). In some embodiments, the tagged circular ssDNA fragments is linearized by cleaving at a restriction site (e.g., using USER enzyme to cleave deoxyuridine (U)) within the 5'-transposon end composition tag, resulting in 5'- and 3'-tagged ssDNA fragments (or "di-tagged ssDNA fragments", with a portion of the transposon end composition tag on the 5' end, and the other portion of the transposon end composition tag on the 3' end). These di-tagged ssDNA fragments can be subjected to further manipulation (e.g., amplification, generating sequencing library for sequencing). In some embodiments, the transposon end composition comprises a sample index tag on the 5' portion of the transferred strand, thus different DNA samples can be first tagmented with different transposon end composition carrying different sample index tags, then pooled together for later denaturing, self-circularization steps, etc.

In some embodiments, there is provided a method of sequencing a nucleic acid sequence on a chromosome, comprising: (a) randomly inserting a plurality of transposon end compositions comprising transposon end described herein into the chromatin or double-stranded nucleic acid fragments thereof (e.g., chromatin DNA) in the presence of a transposase (e.g., Tn5), wherein the transposon end composition comprises, from 5' to 3': a sample index tag, an amplification tag, a restriction site tag, and a transposon end; and (b) determining the nucleic acid fragment sequences. In some embodiments, the chromatin sample is cross-linked. In some embodiments, the chromatin sample is not cross-linked (native chromatin). In some embodiments, the method comprises: incubating the chromatin (native or cross-linked) in an in vitro or in vivo transposition reaction with at least one transposase and a transposon end composition with which the transposase forms a transposome complex, the transposon end composition comprising (i) a transferred strand that exhibits a transferred transposon end sequence, and sample index tag, restriction site tag, amplification tag 5'-of the transferred transposon end sequence, optionally, other additional sequence 5'-of the transferred transposon end sequence; and (ii) a non-transferred strand that exhibits a sequence that is complementary to the transferred transposon end sequence, under conditions and for sufficient time wherein multiple insertions into the target DNA occur, each of which results in joining of a transposon end composition tag comprising or consisting of the transferred strand to the 5' end of a nucleotide in the target DNA (e.g., chromatin DNA), thereby fragmenting the chromatin (or chromatin DNA) and generating a population of annealed 5'-tagged chromatin (or chromatin DNA) fragments, each of which has the transposon end composition tag on the 5'-end. In some embodiments, when tagmenting the chromatin with the transposon end composition and transposase, the double-stranded chromatin DNA is tagged on one strand with 5'-transposon end composition tagged transferred strand, and on the other strand also with a 5'-tagged transferred strand. However, during denaturing step, these 5' dual-tagged chromatin dsDNA fragments are denatured into two 5'-transposon end composition tagged ssDNA, similar to the embodiments where chromatin is only tagmented with a 5'-tag. In some embodiments, the 5'-tagged chromatin (or chromatin DNA) is immunoprecipitated with a binding agent (e.g., an antibody or fragments thereof) specifically recognizing the protein of interest, then reverse-crosslinked and denatured at high temperature, resulting in 5'-tagged ssDNA fragments; then the 3'-ends of the 5'-tagged DNA fragments are joined to the 5' tag (e.g., self-circularization by CircLigase), thereby generating a library of tagged circular ssDNA fragments. These tagged circular ssDNA fragments can be subjected to further manipulation (e.g., amplification, generating sequencing library for sequencing). In some embodiments, the 5'-tagged chromatin (or chromatin DNA) fragments are directly reverse-crosslinked and denatured at high temperature, resulting in 5'-tagged ssDNA fragments; then the 3'-ends of the 5'-tagged DNA fragments are joined to the 5' tag (e.g., self-circularization by CircLigase), thereby generating a library of tagged circular ssDNA fragments. These tagged circular ssDNA fragments can be subjected to further manipulation (e.g., amplification, generating sequencing library for sequencing). For example, this can be done after chromatin has been mildly pre-digested with MNase, and the transposome complexes are merely used to tagging the digested chromatin, rather than further fragmenting harshly. These tagged chromatin fragments can be studied for, e.g., nucleosome occupancy or positioning. In some embodiments, the tagged circular ssDNA fragments are linearized by cleaving at a restriction site (e.g., using USER enzyme to cleave deoxyuridine (U)) within the 5'-transposon end composition tag, resulting in 5'- and 3'-tagged ssDNA fragments (or "di-tagged ssDNA fragments", with a portion of the transposon end composition tag on the 5' end, and the other portion of the transposon end composition tag on the 3' end). These di-tagged ssDNA fragments can be subjected to further manipulation (e.g., amplification, generating sequencing library for sequencing). In some embodiments, after obtaining 5'-transposon end composition tagged chromatin (or chromatin DNA) fragments, and before reverse-crosslinking and denaturing, the 5'-tagged chromatin (or chromatin DNA) is subjected to an additional exonuclease (e.g., Exo III) digestion step to digest the tagged chromatin DNA up to the binding boundary of the protein of interest (e.g. transcription factor or nucleosomes). In some embodiments, the transposon end compositions comprise sample index tag on the 5' portion of the transferred strand. Thus, different biological samples can be tagmented with different transposon end compositions carrying different sample indexes, then pooled together for later experiments (e.g. ChIP). In some embodiments, before randomly inserting the transposon end compositions (tagmenting), the sample chromatin is pre-fragmented, e.g. mildly sheared by sonication or MNase.

In some embodiments of any of the methods of the invention, the reaction time for the in vitro or in vivo transposition reaction is two hours or less, one hour or less, 30 minutes or less, or 15 minutes or less. In some embodiments of any of the methods of the invention, the reaction time for the in vitro or in vivo transposition reaction is 5 minutes or less. In some embodiments of any of the methods of the invention wherein the transposome composition comprises the hyperactive Tn5 transposase and a transposon end composition that comprises the transposon end, the reaction time for the in vitro or in vivo transposition reaction is 5 minutes or less.

In some embodiments, the method further comprises the step of non-selectively amplifying the tagged DNA fragments comprising di-tagged ssDNA fragments or tagged circular ssDNA fragments using a thermostable DNA polymerase and at least one primer that is complementary to the 5' tag portion or the 3' tag portion. In some embodiments of the method where only one transposome complex is used in the in vitro or in vivo transposition reaction, the step of amplifying the tagged DNA fragments comprises amplifying the di-tagged ssDNA fragments or the tagged circular ssDNA fragments using a single primer that exhibits the sequence of at least a portion of the transferred strand. In some embodiments, the step of amplifying the tagged DNA fragments using a single primer comprises a PCR or rolling circle replication reaction. In some embodiments, the 5' portion of a primer used for amplifying comprises or consists of a sequencing tag domain.

In some preferred embodiment of any of the methods of the invention, the library of DNA fragments is used to provide templates for DNA sequencing or nucleic acid amplification.

The method provided herein can be integrated with microfluidic, droplet and flow-cell platforms, or used in assembly applications, e.g., coupled with robotics, in order to achieve large-scale genomic analysis in both research and clinical settings. For example, cell samples (directly from cell culture (native chromatin), fixed cells, or cells detached from an embryo/tissue) can be flowed through a microfluidic chip, then Tn5 transposome complexes are added into each individual channel, the sample is ChIPed, library preparation is performed within each individual department via automation.

Protein of Interest

Eukaryotic genomes are hierarchically packaged into chromatin, and the nature of this packaging plays a central role in gene regulation. Gene transcription occurs in the context of the nucleosomal structure of chromatin. A nucleosome consists of an octamer of histone proteins (two molecules of each core histone H2A, H2B, H3, and H4) around which is wrapped 147 base pairs (bp) of DNA. Histones are small basic proteins with an unstructured amino-terminal "tail" that are the target of numerous post-translational modifications.

The present invention can be used to study every aspect of epigenetics and epigenomics, such as chromatin accessibility (or nucleosome occupancy), nucleosome positioning, transcription factor (TF) occupancy, histone modification pattern, etc. In some embodiments, the protein of interest directly binds to the chromatin. Thus, any protein that directly interacts with nucleic acid within the genome, e.g., TF that binds to TF binding site, histone modification associated with certain nucleic acid sequence, nucleosome wrapped around nucleic acid, can be of interest of the present invention. In some embodiments, the protein of interest indirectly binds to the chromatin. For example, the genomic location or occupancy of a protein X that interacts with a DNA-bound protein Y can be analyzed (e.g., during fixation, DNA-protein Y-protein X is fixed together as a complex), even if protein X does not directly bind to the underlying DNA. The protein of interest can be selected from, e.g., transcription factor, histone, histone modification, chromatin remodeler, chromatin modifier (e.g. histone modifier), transcription machinery elements, insulator binding protein such as CTCF.

Many polypeptides and protein complexes interact with the nucleosome and the histones to regulate chromatin function. A "polypeptide complex" or "protein complex" as used herein, is intended to describe proteins and polypeptides that assemble together to form a unitary association of factors. The members of a polypeptide complex may interact with each other via non-covalent or covalent bonds. Typically members of a polypeptide complex will cooperate to enable binding either to a nucleic acid sequence or to polypeptides and proteins already associated with or bound to a nucleic acid sequence in chromatin. Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, particular polypeptide complexes may vary in their constituent members at different stages of development, in response to varying physiological conditions or as a factor of the cell cycle. By way of example, in animals, polypeptide complexes with known chromatin remodeling activities include Polycomb group gene silencing complexes as well as Trithorax group gene activating complexes.

A protein associated with a chromatin of the invention may be a protein normally expressed in a cell, or may be an exogenous heterologous protein expressed in a cell. In some embodiments, a protein associated with a chromatin of the invention is a protein normally expressed in a cell. In other embodiments, a protein associated with a chromatin of the invention is a protein not normally expressed in a cell.

In some embodiments, the protein of interest is a low abundance chromatin-associated factor—factor that can be found at one or more sites on the chromatin and/or that may associate with chromatin in a transient manner. Examples of low abundance chromatin-associated factors include, but are not limited to, transcription factors (e.g., tumor suppressors, oncogenes, cell cycle regulators, development and/or differentiation factors, general transcription factors), activator (e.g., histone acetyl transferase (HAT)) complexes, repressor (e.g., histone deacetylase (HDAC)) complexes, co-activators, co-repressors, other chromatin-remodelers, e.g., histone (de-) methylases, DNA methylases, replication factors and the like. Such factors may interact with the chromatin (DNA, histones) at particular phases of the cell cycle (e.g., G1, S, G2, M-phase), upon certain environmental cues (e.g., growth and other stimulating signals, DNA damage signals, cell death signals) upon transfection and transient or stable expression (e.g., recombinant factors) or upon infection (e.g., viral factors). Abundant factors are constituents of the chromatin, e.g., histones. Histones may be modified at histone tails through posttranslational modifications which alter their interaction with DNA and nuclear proteins and influence for example gene regulation, DNA repair and chromosome condensation. The H3 and H4 histones have long tails protruding from the nucleosome which can be covalently modified, for example by methylation, acetylation, phosphorylation, ubiquitination, sumoylation, citrullination and ADP-ribosylation. The core of the histones H2A and H2B can also be modified. Combinations of modifications are thought to constitute the so-called "histone code" (Strahl and Allis (2000) Nature 403 (6765): 41-5; Jenuwein and Allis (2001) Science 293 (5532): 1074-80).

Thus, for example, in some embodiments, the protein of interest can be a transcription factor (TF; sometimes called a sequence-specific DNA-binding factor). A transcription factor (sometimes called a sequence-specific DNA-binding factor) is a protein that binds to specific DNA sequences, thereby controlling the rate of transcription of genetic information from DNA to messenger RNA. Exemplary transcription factors include, but are not limited to, AAF, ab1, ADA2, ADA-NF1, AF-1, AFP1, AhR, AIIN3, ALL-1, alpha-CBF, alpha-CP1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1 L, A-Myb, ANF, AP-1, AP-2alphaA, AP-2alphaB, AP-2beta, AP-2gamma, AP-3 (1), AP-3 (2), AP-4, AP-5, APC, AR, AREB6, Arnt, Arnt (774 M form), ARP-1, ATBF1-A, ATBF1-B, ATF, ATF-1, ATF-2, ATF-3, ATF-3deltaZIP, ATF-a, ATF-adelta, ATPF1, Barhl1, Barhl2, Barx1, Barx2, Bcl-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACC-binding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, Chx10, CLIM1, CLIM2, CNBP, CoS, COUP, CP1, CP1A, CP1C, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, deltaCREB, deltaMax, DF-1, DF-2, DF-3, Dlx-1, Dlx-2, Dlx-3, Dlx4 (long isoform), Dlx-4 (short isoform, Dlx-5, Dlx-6, DP-1, DP-2, DSIF, DSIF-p14, DSIF-p160, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, EIf-1, EIk-1, Emx-1, Emx-2, Emx-2, En-1, En-2, ENH-bind. prot., ENKTF-1, EPAS1, epsilonF1, ER, Erg-1, Erg-2, ERR1, ERR2, ETF, Ets-1, Ets-1 delta Vil, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOX01a, FOX01b, FOXO2, FOXO3a, FOXO3b, FOXO4, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GR beta, GRF-1, Gsc, Gsc1, GT-IC, GT-IIA, GT-IIBalpha, GT-IIBbeta, H1TF1, H1TF2, H2RIIBP, H4TF-1, H4TF-2, HAND1, HAND2, HB9, HDAC1, HDAC2, HDAC3, hDaxx, heat-induced factor, HEB, HEB1-p67, HEB1-p94, HEF-1 B, HEF-1T, HEF-4C, HEN1, HEN2, Hesx1, Hex, HIF-1, HIF-1alpha, HIF-1beta, HiNF-A, HiNF-B, HINF-C, HINF-D, HiNF-D3, HiNF-E, HiNF-P, HIP1, HIV-EP2, Hlf, HLTF, HLTF (Met123), HLX, HMBP, HMG I, HMG I(Y), HMG Y, HMGI-C, HNF-1A, HNF-1B, HNF-1C, HNF-3, HNF-3alpha, HNF-3beta, HNF-3gamma, HNF4, HNF-4alpha, HNF4alpha1, HNF-4alpha2, HNF-4alpha3, HNF-4alpha4, HNF4gamma, HNF-6alpha, hnRNP K, HOX11, HOXA1, HOXA10, HOXA10 PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, irlB, IRX2a, Irx-3, Irx-4, ISGF-1, ISGF-3, ISGF3alpha, ISGF-3gamma, 1st-1, ITF, ITF-1, ITF-2, JRF, Jun, JunB, JunD, kappay factor, KBP-1, KER1, KER-1, Kox1, KRF-1, Ku autoantigen, KUP, LBP-1, LBP-1a, LBX1, LCR-F1, LEF-1, LEF-1B, LF-A1, LHX1, LHX2, LHX3a, LHX3b, LHXS, LHX6.1a, LHX6.1b, LIT-1, Lmo1, Lmo2, LMX1A, LMX1B, L-My1 (long form), L-My1 (short form), L-My2, LSF, LXRalpha, LyF-1, LyI-1, M factor, Mad1, MASH-1, Max1, Max2, MAZ, MAZ1, MB67, MBF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2D0B, MEF-2DA0, MEF-2DA'0, MEF-2DAB, MEF-2DA'B, Meis-1, Meis-2a, Meis-2b, Meis-2c, Meis-2d, Meis-2e, Meis3, Meox1, Meox1a, Meox2, MHox (K-2), Mi, MIF-1, Miz-1, MM-1, MOP3, MR, Msx-1, Msx-2, MTB-Zf, MTF-1, mtTF1, Mxi1, Myb, Myc, Myc 1, Myf-3, Myf-4, Myf-5, Myf-6, MyoD, MZF-1, NC1, NC2, NCX, NELF, NER1, Net, NF III-a, NF NF NF-1, NF-1A, NF-1B, NF-1X, NF-4FA, NF-4FB, NF-4FC, NF-A, NF-AB, NFAT-1, NF-AT3, NF-Atc, NF-Atp, NF-Atx, NfbetaA, NF-CLE0a, NF-CLE0b, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A v1, NKX3A v2, NKX3A v3, NKX3A v4, NKX3B, NKX6A, Nmi, N-Myc, N-Oct-2alpha, N-Oct-2beta, N-Oct-3, N-Oct-4, N-Oct-5a, N-Oct-5b, NP-TCII, NR2E3, NR4A2, Nrf1, Nrf-1, Nrf2, NRF-2beta1, NRF-2gamma1, NRL, NRSF form 1, NRSF form 2, NTF, O2, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-1a, Pbx-1b, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARα, PPARβ, PPARgamma1, PPARγ2, PPUR, PR, PR A, pRb, PRD1-BF1, PRDI-BFc, Prop-1, PSE1, P-TEFb, PTF, PTFα, PTFβ, PTFdelta, PTFγ, Pu box binding factor, Pu box binding factor (BJA-B), PU.1, PuF, Pur factor, R1, R2, RAR-alpha1, RAR-β, RAR-β2, RAR-γ, RAR-γ1, RBP60, RBP-Jκ, Rel, RelA, RelB, RFX, RFX1, RFX2, RFX3, RFXS, RF-Y, RORα1, RORα2, RORα3, RORbeta, RORgamma, Rox, RPF1, RPGα, RREB-1, RSRFC4, RSRFC9, RVF, RXR-α, RXR-β, SAP-1a, SAP1b, SF-1, SHOX2a, SHOX2b, SHOXa, SHOXb, SHP, Sill-p110, SIII-p15, SIII-p18, SIM', Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STATE, T3R, T3R-α1, T3R-α2, T3R-beta, TAF(I)110, TAF(I)48, TAF(I)63, TAF(II)100, TAF(II)125, TAF(II)135, TAF(II) 170, TAF(II)18, TAF(II)20, TAF(II)250, TAF(II)250Delta, TAF(II)28, TAF(II)30, TAF(II)31, TAF(II)55, TAF(II)70-α, TAF(II)70-β, TAF(II)70-γ, TAF-I, TAF-II, TAF-L, Tal-1, Tal-1beta, Tal-2, TAR factor, TBP, TBX1A, TBX1B, TBX2, TBX4, TBXS (long isoform), TBXS (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, tel, TFE3, TFEB, TFIIA, TFIIA-α/β precursor, TFIIA-alpha/beta precursor, TFIIA-gamma, TFIIB, TFIID, TFIIE, TFIIE-α, TFIIE-β, TFIIF, TFIIF-α, TFIIF-β, TFIIH, TFIIH*, TFIIH-CAK, TFIIH-cyclin H, TFIIH-ERCC2/CAK, TFIIH-MAT1, TFIIH-MO15, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-del2, WT1-KTS, WT1-del2, X2BP, XBP-1, XW-V, XX, YAF2, YB-1, YEBP, YY1, ZEB, ZF1, ZF2, ZFX, ZHX1, ZIC2, ZID, ZNF174, amongst others.

Transcription factors perform this function alone or with other proteins in a complex, by promoting (as an activator), or blocking (as a repressor) the recruitment of RNA polymerase (the enzyme that performs the transcription of genetic information from DNA to RNA) to specific genes. Accordingly, the immunoprecipitation binding agent may interact directly with a transcription factor, the complex comprising one or more TFs and/or proteins associated with transcription factors. A defining feature of TFs is that they contain one or more DNA-binding domains (DBDs), which attach to specific sequences of DNA adjacent to the genes that they regulate. Additional proteins such as coactivators, chromatin remodelers, histone acetylases, deacetylases, kinases, and methylases, while also playing crucial roles in gene regulation, lack DNA-binding domains, and, therefore, are not classified as transcription factors. However, the immunoprecipitation binding agent used in the methods of the invention may also interact with such proteins (e.g., an antibody that recognizes a chromatin remodeler). Transcription factors bind to either enhancer or promoter regions of DNA adjacent to the genes that they regulate. Depending on the TF, the transcription of the adjacent gene is either up- or down-regulated. Transcription factors use a variety of mechanisms for the regulation of gene expression. These mechanisms include: stabilize or block the binding of RNA polymerase to DNA; catalyze the acetylation or deacetylation of histone proteins. The TF can either do this directly or recruit other proteins with this catalytic activity. Many transcription factors use one or the other of two opposing mechanisms to regulate transcription: histone acetyltransferase (HAT) activity—acetylates histone proteins, which weakens the association of DNA with histones, which make the DNA more accessible to transcription, thereby up-regulating transcription; and/or histone deacetylase (HDAC) activity—deacetylates histone proteins, which strengthens the association of DNA with histones, which make the DNA less accessible to transcription, thereby down-regulating transcription. The mechanisms for the regulation of gene expression also include recruiting coactivator or corepressor proteins to the transcription factor DNA complex.

In some embodiments, the protein of interest is a histone. Histones can be of any species including human, mouse, dog, rat, pig, monkey, rabbit, chicken, fish, fruit fly, *C. elegans*, plant, etc. Known human histones include five classes H1/H5, H2A, H2B, H3 and H4. The class H1 includes H1 F0, H1 FNT, H1 FOO, H1 FX, HIST1 H1A, HIST1 H1 B, HIST1 H1 C, HIST1 H1 D, HIST1 H1 E and HIST1 H1 T. Class H2A includes H2AFB1, H2AFB2, H2AFB3, H2AFJ, H2AFV, H2AFX, H2AFY, H2AFY2, H2AFZ, HIST1 H2AA, HIST1 H2AB, HIST1 H2AC, HIST1 H2AD, HIST1 H2AE, HIST1 H2AG, HIST1 H2AI, HIST1 H2AJ, HIST1 H2AK, HIST1 H2AL, HIST1 H2AM, HIST2H2AA3 and HIST2H2AC. Class H2B includes H2BFM, H2BFS, H2BFWT, HIST1 H2BA, HIST1 H2BB, HIST1 H2BC, HIST1 H2BD, HIST1 H2BE, HIST1 H2BF, HIST1 H2BG, HIST1 H2BH, HIST1 H2BI, HIST1 H2BJ, HIST1 H2BK, HIST1 H2BL, HIST1 H2BM, HIST1 H2BN, HIST1 H2BO and HIST2H2BE. Class H3 includes HISTH3A, HISTH3B, HISTH3C, HISTH3D, HISTH3E, HISTH3F, HISTH3G, HISTH3H, HISTH3I, HISTH3J, HIST2H3C and HIST3H3. Class H4 includes HIST1 H4A, HIST1 H4B, HIST1 H4C, HIST1 H4D, HIST1 H4E, HIST1 H4F, HIST1 H4G, HIST1 H4H, HIST1 H4I, HIST1 H4J, HIST1 H4K, HIST1 H4 L and HIST4H4. In some embodiments, the binding agent used for immunoprecipitation, in particular the antibody (or fragment thereof) or chemical substance, binds to histones of class H3, in particular H3.3, H3.2, H3.3A, H3.3B or H3.1. In some embodiments, the binding agent, in particular the antibody (or fragment thereof) or chemical substance, binds to H4, H2A.Z or CENP-A (the latter two containing a histone H3 related histone fold).

In some embodiments, the protein of interest is modified histone or histone modification. The amino termini of histones (histone tails) are accessible, unstructured domains that protrude out of the nucleosomes. Histones, especially residues of the amino termini of histones H3 and H4 and the amino and carboxyl termini of histones H2A, H2B and H1, are susceptible to a variety of post-translational modifications including acetylation, methylation, phosphorylation, ribosylation and biotinylation. One type of modification, lysine methylation, is catalyzed by histone lysine methyltransferases (HKMTs). Six lysine residues of histones H3 and H4 have been identified to be the main target sites of methylation: lysines 4, 9, 27, 36, 79 of histone H3 and lysine 20 of histone H4 (Martin & Zhang (2005) *Nat. Rev. Mol. Cell Biol.* 6:838-849). Besides, lysine 26 on histone H1b was also shown to be methylated in vitro and in vivo (Kuzmichev, et al. (2004) *Mol. Cell* 14:183-193). Histone modifications have specific meanings and consequences for genomic translation and accessibility of DNA for further binding proteins and/or other chemical substances. Consequently, it is envisaged that the methods of the invention be used for identifying regions bound by modified histones that may undergo alterations in gene expression, e.g. in diseased tissues/cells such as cancer cells.

Known histone modifications include methylation, acetylation, propionylation, butyrylation, crotonylation, 2-hydroxyisobutyrylation, malonylation, succinylation and ribosylation. In particular, lysine methylation, arginine methylation, lysine acetylation, serine/threonine/tyrosine phosphorylation. In this regard, the addition of one, two or three methyl groups to lysine has little effect on the chemistry of the histone; methylation leaves the charge of the lysine intact and adds a minimal number of atoms so steric interactions are mostly unaffected. However, proteins containing Tudor, chromo or PHD domains, amongst others, can recognize lysine methylation with exquisite sensitivity and differentiate mono, di and tri-methyl lysine, to the extent that, for some lysines (e.g. H4K20) mono, di and tri-methylation have different meanings. Because of this, lysine methylation is a very informative mark and dominates the known histone modification functions. Accordingly, it is envisaged that the binding agents used for immunoprecipitation are specific for lysine methylated histones and/or proteins recognizing such modified histones, e.g. proteins containing Tudor, chromo or PHD domains. With regard to arginine methylated histones, similar reasoning as above applies, i.e. some protein domains—e.g., Tudor domains—can be specific for methyl arginine instead of methyl lysine. Arginine is known to be mono- or di-methylated, and methylation can be symmetric or asymmetric, potentially with different meanings. With regard to lysine acetylation, addition of an acetyl group has a major chemical effect on lysine as it neutralizes the positive charge. This reduces electrostatic attraction between the histone and the negatively charged DNA backbone, loosening the chromatin structure; highly acetylated histones form more accessible chromatin and tend to be associated with active transcription. Lysine acetylation appears to be less precise in meaning than methylation, in that histone acetyltransferases tend to act on more than one lysine; presumably this reflects the need to alter multiple lysines to have a significant effect on chromatin structure. Accordingly, it is also envisaged that the binding agent used for immunoprecipitation is specific for acetylated lysine and/or proteins interacting with acetylated lysine. In addition to the above, serine/threonine and/or tyrosine comprised in histones can be modified by phosphorylation. Addition of a negatively charged phosphate group can lead to major changes in protein structure, leading to the well-characterized role of phosphorylation in controlling protein function. Histone phosphorylation has clear functions as a post-translational modification, and binding domains such as BRCT (BRCA1 C Terminus domain) have been characterized. Therefore, it is also envisaged that such modified histones, i.e. modified by phosphorylation, be recognized by the immunoprecipitation binding agents.

The modifications of histones described above and further modifications described in the art have implications for the control of transcription. In this regard, two known histone modifications are particularly associated with active transcription: trimethylation of H3 lysine 4 (H3K4me3) and trimethylation of H3 lysine 36 (H3K36me3). H3K4me3 occurs at the promoter of active genes and is performed by the COMPASS complex. The modification is an excellent mark of active promoters and the level of this histone modification at a gene's promoter is broadly correlated with transcriptional activity of the gene. The formation of this mark is tied to transcription in a rather convoluted manner: early in transcription of a gene, RNA polymerase II (Pol II) undergoes a switch from initiating to elongating, marked by a change in the phosphorylation states of the RNA polymerase II C terminal domain (Pol II CTD). The same enzyme that phosphorylates the CTD also phosphorylates the Rad6 complex, which in turn adds a ubiquitin mark to H2B K123 (K120 in mammals). H2BK123ub occurs throughout transcribed regions, but this mark is required for COMPASS to trimethylate H3K4 at promoters. Thus, in some embodiments, the immunoprecipitation binding agent, in particular the antibody (or fragments thereof) or chemical substance, is specific for H3K4me3. In some embodiments, the immunoprecipitation binding agent, in particular the antibody (or fragments thereof) or chemical substance is specific for H3K36me3. This trimethylation occurs in the body of active genes and is deposited by the methyltransferase Set2. This protein associates with elongating RNA polymerase II, and H3K36me3 is indicative of actively transcribed genes. H3K36me3 is recognized by the Rpd3 histone deacetylase complex, which removes acetyl modifications from surrounding histones, increasing chromatin compaction and repressing spurious transcription. Increased chromatin compaction prevents transcription factors from accessing DNA, and reduces the likelihood of new transcription events being initiated within the body of the gene. This process therefore helps ensure that transcription is not interrupted. In addition acetylation of lysine 27 of histone H3 (H3K27ac) is present at active regulatory elements as promoters and enhancers. In genetics, an enhancer is a short (50-1500 bp) region of DNA that can be bound with proteins (activators) to activate transcription of a gene. These proteins are usually referred to as transcription factors. Enhancers are generally cis-acting, located up to 1 Mbp (1,000,000 bp) away from the gene and can be upstream or downstream from the start site, and either in the forward or backward direction. There are hundreds of thousands of enhancers in the human genome. In particular, H3K27ac has been described to distinguish active from poised regulatory elements. Enrichment of H3K27ac at these elements is a good indicator for expression of the associated genetic element. Accordingly, the immunoprecipitation binding agent, in particular the antibody (or fragments thereof) or chemical substance, used in the methods of the present invention may be specific for H3K27ac. It is also contemplated that the immunoprecipitation binding agent used in the methods of the invention specifically binds to such modified histones associated with active genes and/or proteins associated therewith (e.g., proteins recognizing these active histone marks). Histone modifications may also be associated with repression of gene expression. For example, H3K27me3, H3K9me2/3 and H4K20me3 are known to be associated with repressed genes. H3K27me3 is deposited by the polycomb complex PRC2. It is a clear marker of gene repression, and is likely bound by other proteins to exert a repressive function. Another polycomb complex, PRC1, can bind H3K27me3 and adds the histone modification H2AK1 19Ub which aids chromatin compaction. The di and tri-methylation of H3 lysine 9 (H3K9me2/3) is a well-characterized marker for heterochromatin, and is therefore strongly associated with gene repression. The same applies to H4K20me3, which is tightly associated with heterochromatin. This mark is placed by the Suv4-20 h methyltransferase, which is at least in part recruited by heterochromatin protein 1. Accordingly, it is also contemplated that the immunoprecipitation binding agent used in the methods of the invention specifically binds to such modified histones associated with repressed genes and/or proteins associated therewith.

Histone modifications also play a role in DNA repair and chromosome condensation. For example, marking sites of DNA damage is an important function for histone modifications. It also protects DNA from getting destroyed by ultraviolet radiation of sun. For example, phosphorylated H2AX (also known as gamma H2AX) is a marker for DNA double strand breaks, and forms part of the response to DNA damage. H2AX is phosphorylated early after detection of DNA double strand break, and forms a domain extending many kilobases either side of the damage. Gamma H2AX acts as a binding site for the protein MDC1, which in turn recruits key DNA repair proteins and as such, gamma H2AX forms a vital part of the machinery that ensures genome stability. Also, H3K56Acx is required for genome stability. H3K56 is acetylated by the p300/Rtt109 complex, but is rapidly deacetylated around sites of DNA damage. H3K56 acetylation is also required to stabilize stalled replication forks, preventing dangerous replication fork collapses. Phosphorylation of H3 at serine 10 (phospho-H3S10) is associated with condensed chromatin, but H3S10 phosphorylation is also present at certain chromosome sites outside mitosis, for example in pericentric heterochromatin of cells during G2. H3S10 phosphorylation has also been linked to DNA damage caused by R loop formation at highly transcribed sites. Phosphorylation of H2B at serine 10 (yeast) or serine 14 (mammals) is also linked to chromatin condensation, but for the very different purpose of mediating chromosome condensation during apoptosis. This mark is not simply a late acting bystander in apoptosis as yeast carrying mutations of this residue are resistant to hydrogen peroxide-induced apoptotic cell death.

Accordingly, the binding agents used for immunoprecipitation, in particular the antibody (or fragments thereof) or chemical substance, may specifically bind to histones, modified histones and/or other factors, in particular polypeptides such as enzymes, interacting with such histones and/or modified histones (e.g., some chromatin remodelers that recognize histone modifications), e.g., H3K4me1/2/3, H2BK5me1, H3K27me1/2/3, H3K9me1/2/3, H4K20me1, H3K79me1, H3K36me3, H2AK5ac, H2AK9ac, H2BK5ac, H2BK12ac, H2BK20ac, H2BK120ac, H3K4ac, H3K9ac, H3K14ac, H3K18ac, H3K23ac, H3K27ac, H3K36ac, H4K5ac, H4K8ac, H4K12ac, H4K16ac, H4K91 ac, H2Aub, or H2Bub.

In some embodiments, the protein of interest is histone modifiers or histone modifying enzymes. Histone modifying enzymes include enzymes that add or remove the following post-translational protein modifications: acetylation (see, e.g., Sterner & Berger (2000) *Microbiol. Mol. Biol. Rev.* 64: 435-459), methylation (see, e.g., Zhang & Reinberg (2001) *Genes Dev.* 15:2343-2360), phosphorylation (see, e.g., Nowak & Corces (2004) *Trends Genet.* 20:14-220), ubiquitination (see, e.g., Shilatifard (2006) *Annu. Rev. Biochem.* 75:243-269), sumoylation (Nathan, et al. (2006) *Genes Dev.* 20:966-976), ADP-ribosylation (see, e.g., Hassa, et al. (2006)*Microbiol. Mol. Biol. Rev.* 70:789-829), deimination (see, e.g., Cuthbert, et al. (2004) *Cell* 118:545-553; Wang, et al. (2004) *Science* 306:279-283), proline isomerization (see, e.g., Nelson, et al. (2006) *Cell* 126:905-916) or biotinylation (e.g. Kobza, et al. (2005) *FEBS J.* 272(16):4249-59).

In some embodiments, the protein of interest is a transcription machinery element, such as RNA polymerase II, general transcription factors TBP, TFIIB, TFIIE, TFIIF, or TFIIH.

In some embodiments, the immunoprecipitation binding agents, in particular the antibody (or fragments thereof) or chemical substance, used in the methods of the present invention may interact with transcription factors known to be associated with diseases, e.g. cancer. In this regard, the methods of the invention may be used to study the interaction between DNA and transcription factors in a diseased cell and/or cells derived from diseased tissue. Also, the methods of the present invention can be used to study interactions between drugs and DNA TFs. In this regard, approximately 10% of currently prescribed drugs directly target the nuclear receptor class of transcription factors. Examples include tamoxifen and bicalutamide for the treatment of breast and prostate cancer, respectively, and various types of anti-inflammatory and anabolic steroids. In addition, transcription factors are often indirectly modulated by drugs through signaling cascades. In some embodiments, the protein of interest is a mutated TF (e.g., in a disease state).

In accordance with the above, the present invention in some embodiments relates to methods for mapping of molecular interactions involving nucleic acid, in particular DNA, wherein the method provides valuable information with regard to the interaction of polypeptides with a nucleic acid, in particular DNA. The nucleic acid may be derived from any source, e.g. cells. In particular, cells comprising nucleic acid-protein complexes. In some embodiments, the cells are human cells, animal cells, bacterial cells, yeast cells, archaeal cells, plant cells or viruses. In some embodiments, the cells are human cells. However, cells may also be from non-native sources, e.g. engineered cells or artificially modified cells, in particular genetically modified cells. In addition, the human or animal cells may be diseased cells or non-diseased cells or cells derived from diseased or non-diseased tissue. In this regard, the human or animal cells may be cancer cells, immune cells, blood cells or stem cells. In some embodiments, the cells are cancer cells. The cancer may be a solid cancer or blood cancer, in particular leukemia or a tumor. Known cancers associated with altered transcription, i.e. altered accessibility of DNA, modified histones, modified transcription factors and the like, are summarized by Yeh et al. (2013) Curr. Opin. Oncol. 25(6). The cells may also be embryonic cells.

Cells and Samples

Chromatin or a target nucleic acid sequence may be isolated from any cell comprising the target nucleic acid sequence of the invention. A cell may be an archaebacterium, a *eubacterium*, or a eukaryotic cell. For instance, a cell of the invention may be a methanogen, a *halophile* or a thermoacidophile archaeabacterium, a gram positive, a gram negative, a cyanobacterium, a spirochaete, or a firmicute bacterium, a fungal cell, a moss cell, a plant cell, an animal cell, an insect cell, an Arachnid cell, or a protist cell. In some embodiments, the cell is from an invertebrate.

In some embodiments, a cell of the invention is a cell from an animal. A cell from an animal cell may be a cell from an embryo, a juvenile, or an adult. Suitable animals include vertebrates such as mammals (e.g., human, or non-human mammals), birds, reptiles, amphibians, and fish. Examples of suitable mammals include without limit rodents, companion animals, livestock, and primates. Non-limiting examples of rodents include mice, rats, hamsters, gerbils, and guinea pigs. Suitable companion animals include but are not limited to cats, dogs, rabbits, hedgehogs, and ferrets. Non-limiting examples of livestock include horses, goats, sheep, swine, cattle, llamas, and alpacas. Suitable primates include but are not limited to humans, capuchin monkeys, chimpanzees, lemurs, macaques, marmosets, tamarins, spider monkeys, squirrel monkeys, and vervet monkeys. Non-limiting examples of birds include chickens, turkeys, ducks, and geese. In some embodiments, a cell is a cell from a human.

In some embodiments, a cell may be from a model organism commonly used in laboratory research. For instance, a cell of the invention may be an *E. coli*, a *Bacillus subtilis*, a *Caulobacter crescentus*, a *Mycoplasma genitalium*, an *Aliivibrio fischeri*, a *Synechocystis*, or a *Pseudomonas fluorescens* bacterial cell; a *Chlamydomonas reinhardtii*, a *Dictyostelium discoideum*, a *Tetrahymena thermophila*, an *Emiliania huxleyi*, or a *Thalassiosira pseudonana* protist cell; an *Ashbya gossypii*, an *Aspergillus nidulans*, a *Coprinus cinereus*, a *Cunninghamella elegans*, a *Neurospora crassa*, a *Saccharomyces cerevisiae*, a *Schizophyllum commune*, a *Schizosaccharomyces pombe*, or an *Ustilago maydis* fungal cell; an *Arabidopsis thaliana*, a *Selaginella moellendorffii*, a *Brachypodium distachyon*, a *Lotus japonicus*, a *Lemna gibba*, a *Zea mays*, a *Medicago truncatula*, a Mimulus, a tobacco, a rice, a *Populus*, or a *Nicotiana benthamiana* plant cell, a *Physcomitrella patens* moss; an *Amphimedon queenslandica* sponge, an Arbacia *punctulata* sea urchin, an Aplysia sea slug, a Branchiostoma *floridae* deuterostome, a *Caenorhabditis elegans* nematode, a Ciona intestinalis sea squirt, a *Daphnia* spp. crustacean, a *Drosophila* fruit fly, a Euprymna scolopes squid, a Hydra Cnidarian, a Loligo pealei squid, a Macrostomum lignano flatworm, a Mnemiopsis leidyicomb jelly, a Nematostella vectensis sea anemone, an Oikopleura *dioica* free-swimming tunicate, an Oscarella carmela sponge, a *Parhyale hawaiensis* crustacean, a Platynereis *dumerilii* marine polychaetous annelid, a *Pristionchus* pacificus roundworm, a Schmidtea *mediterranea* freshwater planarian, a Stomatogastric ganglion of various arthropod species, a Strongylocentrotus purpuratus sea urchin, a Symsagittifera roscoffensis flatworm, a *Tribolium castaneum* beetle, a Trichoplax *adhaerens* Placozoa, a Tubifex tubifex oligochaeta, a laboratory mouse, a Guinea pig, an avian (e.g., a Chicken), a Cat, a Dog, a Hamster, a Lamprey, a Medaka fish, a Rat, a Rhesus macaque, a Cotton rat, a Zebra finch, a Takifugu pufferfish, an African clawed frog, or a Zebrafish. In exemplary embodiments, a cell is a *Saccharomyces cerevisiae* yeast cell. In particularly exemplary embodiments, a cell is a *Saccharomyces cerevisiae* W303a yeast cell.

A cell of the invention may be derived from a tissue or from a cell line grown in tissue culture. A cell line may be adherent or non-adherent, or a cell line may be grown under conditions that encourage adherent, non-adherent or organotypic growth using standard techniques known to individuals skilled in the art. Cell lines and methods of culturing cell lines are known in the art. Non-limiting examples of cell lines commonly cultured in a laboratory may include HeLa, a cell line from the National Cancer Institute's 60 cancer cell lines, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSYSY Human neuroblastoma cells, Saos-2 cells (bone cancer), Vero, GH3 (pituitary tumor), PC12 (pheochromocytoma), MC3T3 (embryonic calvarium), Tobacco BY-2 cells, Zebrafish ZF4 and AB9 cells, Madin-Darby canine kidney (MDCK), or *Xenopus* A6 kidney epithelial cells.

A cell of the invention may be derived from a biological sample. As used herein, the term "biological sample" refers to a sample obtained from a subject. Any biological sample containing a cell is suitable. Numerous types of biological samples are known in the art. Suitable biological sample may include, but are not limited to, tissue samples or bodily fluids. In some embodiments, the chromatin may be isolated from a soft tissue such as brain, adrenal gland, skin, lung, spleen, kidney, liver, spleen, lymph node, bone marrow, bladder stomach, small intestine, large intestine or muscle, etc. In some embodiments, the biological sample is a tissue sample such as a tissue biopsy. The tissue biopsy may be a biopsy of a known or suspected tumor. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may also be primary and/or transformed cell cultures derived from tissue from the subject. In other embodiments, the sample may be a bodily fluid. Non-limiting examples of suitable bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, semen, etc. The fluid may be used "as is", the cellular components may be isolated from the fluid, or a protein fraction may be isolated from the fluid using standard techniques. In some embodiments, the polynucleotide (e.g. genomic DNA, chromosomal DNA) used in the method may be from blood cells, wherein blood cells refers to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). In certain embodiments, the cell sample can be isolated directly from a primary source. For example, the cell sample can be isolated directly from fresh tissues. In other cases, the cell sample can be isolated directly from frozen tissues. In yet other cases, the cell sample can be isolated directly from fixed tissues. Further examples of primary sources of cell samples include, but are not limited to, cells dissociated from tissues, blood cells, FFPE tissues, bacterial, viral, mitochondria, chloroplast, in vitro assembled protein DNA complexes, neutrophil extracellular traps, etc.

Suitable subjects or sample source of the chromatin include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In some embodiments, the subject is human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that chromatin can be accurately detected, isolated, and measured according to the invention.

Using the methods provided in the present disclosure, the disease state in a subject can be analyzed based on the accessibility of a polynucleotide site in a cell (or chromatin) sample obtained from the subject. For example, transcription factor occupancy at any given site can result in the lack of accessibility at the site. Based on the transcription factor occupancy, the subject can then be treated with a suitable agent (e.g. a transcription factor inhibitor).

In the methods of the invention, prior to preparing a sequencing library or mapping molecular interactions involving a nucleic acid, the sample comprising a nucleic acid is preferably prepared by cultivating and harvesting cells; optionally fixing cells; lysing cells and thereby obtaining a first sample comprising a nucleic acid; and optionally sonicating the sample and thereby obtaining a second sample comprising a nucleic acid. It is preferred that said second sample is used in the methods of the invention for preparing a sequencing library or mapping of molecular interactions involving a nucleic acid. Where the sample comprising a nucleic acid is a primary cell sample, e.g. a sample derived from a donor, the step of cultivating and harvesting may be omitted. Accordingly, where the sample comprising a nucleic acid is a primary cell sample, the methods of the invention preferably further comprise optionally fixing cells; lysing cells and thereby obtaining a first sample comprising a nucleic acid; and optionally sonicating the first sample and thereby obtaining a second sample comprising a nucleic acid.

Accordingly, the sample comprising a nucleic acid is in some embodiments prepared by a method comprising cultivating and harvesting of cells. This may be done using methods well-known in the art. In particular, cultivation methods must be suitable for the cell type used in analysis. Such methods are described in, e.g. Helgason et al. (2005) Basic Cell Culture Protocols, Methods in Molecular Biology or Freshney (2010) Culture of Animal Cells, Wiley-Blackwell. Harvesting of cells is also done by well-known methods described in the art. For example, cells may be harvested by centrifugation, whereby cells are found in the resulting cell pellet while the supernatant contains the used culture medium.

Subsequent to harvesting cultivated cells, the cells may be optionally fixed. Fixation is used to preserve a sample from decay. Accordingly, in this process, structures are preserved in a state (both chemically and structurally) as close to the native state, e.g. in living tissue, as possible. This requires a chemical or physical fixative that can stabilize proteins and/or nucleic acids of the tissue by making them insoluble. In addition to preserving such a state, fixatives are used to crosslink macromolecules, in particular proteins and/or nucleic acids, contained in the sample.

Because the methods of the invention are particularly useful for analysis of low cell numbers, it is evident that sources having a limited number of cells available as source of the nucleic acid to be analyzed, are particularly envisaged. Such sources include early embryonic stages of humans or animals. In cases of diseases, in particular human diseases, the cell numbers may be restricted by the nature of the disease, e.g. cancer metastasis, small primary tumors or small diseased organs, rare tissues and rare cell types. The cell numbers of human clinical samples can further be restricted by the approach to obtain the sample, e.g. needle biopsies or blood draws. Accordingly, samples derived from such sources are also contemplated for use in the methods of the present invention. In addition, cell numbers may be limited due to other restrictions, e.g. protected animals, rare animals, endangered animals or the like. Furthermore, the methods of the invention are particularly useful in single-animal studies, in particular of small animals, such as *C. elegans*, zebrafish, fruit fly, or Ascidiacea.

The population of cells used in the assay may be composed of any number of cells, e.g., about 500 to about $10^9$ or more cells, about 500 to about $10^8$ cells, about 500 to about $10^7$ cells, about 500 to about $10^6$ cells, about 500 to about 100,000 cells, about 500 to about 50,000 cells, about 500 to about 10,000 cells, about 500 to about 1000 cells, about 1 to about 500 cells, about 1 to about 100 cells, about 1 to about 50 cells, or a single cell. In some embodiments, the cell sample can comprise about 1000 to about 2000, about 2000 to about 3000, about 3000 to about 4000, about 4000 to about 5000, about 5000 to about 6000, about 6000 to about 7000, about 7000 to about 8000, about 8000 to about 9000, about 9000 to about 10,000, about 10,000 to about 15,000, about 15,000 to about 20,000, about 20,000 to about 25,000, about 25,000 to about 30,000, about 30,000 to about 40,000, about 40,000 to about 50,000, about 50,000 to about 60,000, about 60,000 to about 70,000, about 70,000 to about 80,000, about 80,000 to about 90,000, about 90,000 to about 100,000, about 100,000 to about 150,000, about 150,000 to about 200,000, about 200,000 to about 250,000, about 250,000 to about 300,000, about 300,000 to about 350,000, about 350,000 to about 400,000, about 400,000 to about 450,000, about 450,000 to about 500,000, about 500,000 to about 600,000, about 600,000 to about 700,000, about 700,000 to about 800,000, about 800,000 to about 900,000, about 900,000 to about 1,000,000, about 10 to about 100, about 100 to about 1000, about $10^3$ to about $10^4$, about $10^4$ to about $10^5$, about $10^5$ to about $10^6$, about $10^6$ to about $10^7$, about $10^7$ to about $10^8$, or about $10^8$ to about $10^9$ cells. In some embodiments, the sample comprises about 500 to about 1000 cells.

As described above, one advantage of the present invention over other ChIP-seq techniques is its enablement of combining multiple samples into one experimental reaction, so that variances among different samples during different experiments are significantly minimized, samples can start with smaller amount of cells or nuclei, samples can be quantitatively and qualitatively compared with each other, while different samples can be told apart. In some embodiments, different cell samples, or lysates (comprising chromatin) derived from different cell samples, are individually tagged on their chromatin (e.g., by different transposon end compositions, such as transposon end compositions comprising different sample index tags), then combined together. Thus, in some embodiments, the sample only comprises one cell sample, or lysate derived from one cell sample. In some embodiments, at least two cell samples (or lysates derived from two cell samples) are combined before starting immunoprecipitation using the binding agent (such as antibody). In some embodiments, at least two cell samples, or lysates derived from at least two cell samples are combined, then tagged (e.g., by transposon end compositions), and the tagged target chromatin is isolated from the combined cells or combined cell lysates. In some embodiments, cells from different cell samples of the invention are from the same type of cells or they may be derived from the same type of cells. For instance, cells may comprise a heterologous nucleic acid in a target chromatin, and may also comprise a heterologous protein expressed in a cell. The heterologous nucleic acid in a target chromatin, or the heterologous protein expressed in a cell (e.g., a particular TF only existing in one cell type), may be used for identifying the chromatin sample from other mixed chromatin sample. Cell samples of the invention may be from the same genus, species, variety or strain of cells. In some embodiments, cells in different cell samples of the invention are from the same type of cells. In some embodiments, cells in different cell samples of the invention are from the same type of cells, but treated or grown under different conditions. In some embodiments, cells in different cell samples of the invention are derived from the same organism but under different developmental stages (e.g., embryo vs. adult). In some embodiments, cells in the first cell sample are derived from the same cell type as cells in the second cell sample. In some embodiments, the sample cam comprise at least any of 1, 2, 3, 4, 5, 6, 7, 8, 9, 10, 11, 12, 13, 14, 15, 16, 17, 18, 19, 20, 25, 30, 40, 50, 60, 70, 80, 90, 100, or more chromatin samples (or cell samples, lysate samples derived from the cell samples). In some embodiments in the combined sample, one cell sample or chromatin sample is labeled (or tagged), while the other cell sample or chromatin sample is not labeled (or tagged). The number of cells in a cell sample can and will vary depending on the type of cells, the abundance of a target chromatin in a cell, and the method of protein identification used, among other variables.

Cell samples (or chromatin samples) may be combined (or pooled) under different ratios, or under the same ratio. For example, when the sample comprises 2 cell samples (or chromatin samples), they may be combined in a weight to weight (w/w) ratio of about 1:100 to about 100:1, about 1:50 to about 50:1, about 1:25 to about 25:1, about 1:10 to about 10:1, about 1:5 to about 5:1, about 1:2 to about 2:1, about 1:1.5 to about 1.5:1, or about 1:1. In some embodiments, cell samples (or chromatin samples) are combined in a w/w ratio of about 1:1. In some embodiments, the cell samples (or chromatin samples, cell lysates) are combined under the same ratio, or with different ratios, using volume to volume (v/v) ratio. If cell lysates derived from two cell samples of the invention are combined, lysates derived from cell ratios described herein are combined. Individuals of ordinary skill in the art will recognize that ratios of cell samples or lysates derived from cell samples described herein may be subject to statistical confidence limits of actual cell weight. For instance, the ratio may be based on 85, 90, 95% or more confidence limits on cell weight.

Proteins (e.g., TFs, chromatin remodelers of interest) in a cell sample can be metabolically labeled. Methods of metabolically labeling proteins in a cell are known in the art and may comprise culturing a cell in the presence of at least one labeled analogue of a biomolecule that is metabolized by a cell. When the labeled analog of a biomolecule is supplied to cells in culture instead of the unlabeled biomolecule, the labeled biomolecule is incorporated into all newly synthesized proteins. After a number of cell divisions, each instance of this particular labeled biomolecule will be replaced by its labeled analog. Since there is hardly any chemical difference between the labeled biomolecule and the unlabeled biomolecule, the cells behave exactly like the control cell population grown in the presence of unlabeled biomolecule. As such, up to 100% of the particular biomolecule in a cell may be labeled. In some embodiments, up to 10, 20, 30, 40, 50, 60, 70, 80, 90 or up to 100% of the particular biomolecule in a cell is labeled. In some embodiments, up to 50, 60, 70, 80, 90 or up to 100%, and more preferably up to 90 or up to 100% of the particular biomolecule in a cell is labeled. In preferred embodiments, up to 100% of the particular biomolecule in a cell is labeled. Non-limiting examples of a biomolecule that may be labeled and is metabolized by a cell may include an amino acid, a nucleic acid, a carbohydrate or a labeled molecule that may be incorporated into an amino acid, a nucleic acid, or a carbohydrate. Non-limiting examples of a labeled molecule that may be incorporated into an amino acid, a nucleic acid, a carbohydrate may include labeled ammonium sulfate, and labeled ammonium chloride. A labeled biomolecule may be a component of a cell culture medium such as a food source, e.g., glucose, sera or cell extracts. In some embodiments, a labeled biomolecule that is metabolized by a cell of the invention is a labeled nucleic acid. In some embodiments, a labeled biomolecule that is metabolized by a cell of the invention is a labeled carbohydrate such as [$^{13}$C]glucose. In some embodiments, a biomolecule that is metabolized by a cell of the invention is a labeled amino acid. A labeled biomolecule may be labeled using a heavy isotope of one or more atoms of the biomolecule. Such labeling can be used to tell one chromatin sample from the other chromatin sample.

Lysing refers to the breaking down of cellular membranes. A skilled practitioner of the art will appreciate that protocols for lysing a cell can and will vary depending on the type of cell, the target chromatin of the invention, and the specific application of a method of the invention.

Non-limiting examples of methods that may be used to lyse a cell of the invention may include cell lysis using a detergent, an enzyme such as lysozyme, incubation in a hypotonic buffer which causes a cell to swell and burst, mechanical disruption such as liquid homogenization by forcing a cell through a narrow space, sonication, freeze/thaw, mortar and pestle, glass beads, and combinations thereof. Certain methods of cell lysis are described in Thermo Scientific Pierce Cell Lysis Technical Handbook or Lottspeich, Engels (2012) Bioanalytik, Springer Spektrum.

Buffer conditions used during lysing and isolation of a chromatin of the invention can and will be altered to control stringent conditions during cell lysis and isolation to preserve association of proteins and nucleic acid sequences of a chromatin. "Stringent conditions" in the context of chromatin isolation are conditions capable of preserving specific association of proteins and nucleic acids of a chromatin, but minimizing non-specific association of proteins and nucleic acids. Stringent condition can and will vary depending on the application of a method of the invention, the target chromatin of the invention, the nucleic acid sequence in a target chromatin, the proteins or protein complexes associated with a target chromatin of the invention, whether or not proteins, protein complexes and nucleic acid sequences are crosslinked, and the conditions used for crosslinking proteins, protein complexes and nucleic acid sequences of a target chromatin. For instance, more stringent buffer conditions may be used in a method of the invention wherein proteins, protein-protein complexes, and protein-nucleic acid complexes are crosslinked compared to a method of the invention wherein proteins, protein-protein complexes, and protein-nucleic acid complexes are not crosslinked. As such, stringent buffer conditions used during cell lysis and isolation of a nucleic acid sequence of the invention may be experimentally determined for each application wherein a method of the invention is used. Buffer conditions that may alter stringent conditions during cell lysis and isolation may include pH and salt concentration. In some embodiments, proteins, protein-protein complexes, and protein-nucleic acid complexes of a target chromatin of the invention are crosslinked, and stringent buffer conditions are used during lysis and isolation of a chromatin of the invention.

Chromatin

Generally, chromatin refers to the combination of nucleic acids and proteins in the nucleus of a eukaryotic cell. However, it is contemplated that the term "chromatin" may also refer to the combination of any nucleic acid sequence and proteins associated with the nucleic acid sequence in any cell.

A chromatin of the invention may comprise single stranded nucleic acid, double stranded nucleic acid, or a combination thereof. In some embodiments, a chromatin comprises single stranded nucleic acid. In other embodiments, a chromatin comprises a combination of single stranded and double stranded nucleic acids. In yet other embodiments, a chromatin comprises double stranded nucleic acid.

A chromatin of the invention may comprise a ribonucleic acid (RNA), a deoxyribonucleic acid (DNA), or a combination of RNA and DNA. In some embodiments, a chromatin of the invention comprises a combination of a RNA sequence and proteins associated with the RNA sequence in a cell. Non-limiting examples of RNA sequences may include mRNA, and non-coding RNA such as tRNA, rRNA, snoRNAs, microRNAs, siRNAs, piRNAs and the long non-coding RNA (lncRNA). In some embodiments, a chromatin of the invention comprises a combination of a DNA sequence and proteins associated with the DNA sequence in a cell. In some embodiments, a chromatin of the invention comprises a combination of RNA and DNA sequences, and proteins associated with the RNA and DNA sequence in a cell. Non limiting examples of chromatin that may comprise a combination of RNA and DNA may include genomic DNA undergoing transcription, or genomic DNA comprising non-coding RNA such as lncRNA.

A chromatin of the invention may be genomic chromatin such as, chromatin from a chromosome of a cell, or chromatin from an organelle in the cell. Alternatively, a chromatin may be chromatin from an extrachromosomal nucleic acid sequence. In some embodiments, a chromatin of the invention is chromatin from an organelle in the cell. Non-limiting examples of a chromatin from an organelle may include mitochondrial nucleic acid sequence in plant and animal cells, and a chloroplast nucleic acid sequence in plant cells. In some embodiments, a nucleic acid sequence of the invention is a mitochondrial nucleic acid sequence. In other embodiments, a nucleic acid sequence of the invention is a chloroplast nucleic acid sequence.

In some embodiments, a chromatin of the invention is chromatin from an extrachromosomal nucleic acid sequence. The term "extrachromosomal," as used herein, refers to any nucleic acid sequence not contained within the cell's genomic nucleic acid sequence. An extrachromosomal nucleic acid sequence may comprise some sequences that are identical or similar to genomic sequences in the cell, however, an extrachromosomal nucleic acid sequence as used herein does not integrate with genomic sequences of the cell. Non-limiting examples of an extrachromosomal nucleic acid sequence may include a plasmid, a virus, a cosmid, a phasmid, and a plasmid.

In some preferred embodiments, a chromatin of the invention is genomic chromatin. In exemplary embodiments, a chromatin of the invention is genomic chromatin of a eukaryotic cell, e.g., any of the eukaryotic cells described herein.

A chromatin of the invention may be an intact and complete chromatin from the cell, or may be a fragment of a chromatin in a cell. In some embodiments, a chromatin of the invention is an intact chromatin isolated from a cell. For instance, a chromatin of the invention may be a plasmid, a cosmid, or a phage chromatin or a complete organellar chromatin. In some embodiments, a chromatin of the invention is a fragment of a chromatin from a cell. In exemplary embodiments, a chromatin of the invention is a fragment of a genomic chromatin from a cell.

A target chromatin fragment of the invention may comprise a structural or a functional feature of chromatin as described herein, a fragment of a physical or functional feature, or no physical or functional features or known physical or functional features. In some embodiments, a target chromatin fragment of the invention comprises a structural feature of chromatin. In other embodiments, a target chromatin fragment of the invention comprises no physical or functional features or known physical or functional features. In yet other embodiments, a target chromatin fragment of the invention comprises a functional feature of chromatin, such as promoter, enhancer, gene body, insulator sequences, etc.

Chromatin can be isolated or extracted from a cell lysate, or a combined cell lysate. A combined cell lysate comprises a lysate of two or more combined cell samples, or a combination of two or more cell lysates derived from two or more cell samples. In some embodiments, a target chromatin is tagged or labeled in one of the cell samples. Irrespective of whether one cell sample or a combined cell sample is lysed, a skilled practitioner of the art will appreciate that structural and functional features of a target chromatin must be preserved during cell lysis and isolation of the target chromatin. The association of proteins with a target chromatin may be preserved during cell lysis and isolation of the target chromatin using methods known in the art for preserving a complex of proteins with a nucleic acid sequence. For instance, lysing of a cell and isolation of a target chromatin may be performed under refrigeration or using cryogenic methods and buffer conditions capable of preserving association of proteins and nucleic acid sequences. In addition, a complex of proteins with a nucleic acid may be preserved by crosslinking protein and nucleic acid complexes in a cell prior to lysing and isolating a chromatin. Crosslinking protein and nucleic acid complexes in a cell may also capture, or preserve, transient protein-protein and protein-nucleic acid interactions.

Cross-Linking

In some embodiments, the chromatin is not cross-linked (native chromatin). In some embodiments, the chromatin is cross-linked before isolation and/or tagmentation.

In some embodiments, the interaction between a protein or a complex of proteins and a nucleic acid may be preserved by crosslinking protein and nucleic acid complexes in a chromatin prior to lysing a cell and isolating the chromatin. Crosslinking is the process of joining two or more molecules such as two proteins or a protein and a nucleic acid molecule, by a covalent bond. Molecules may be crosslinked by irradiation (such as with ultraviolet light), or by using chemical crosslinking reagents. Chemical crosslinking reagents capable of crosslinking proteins and nucleic acids are known in the art and may include crosslinking reagents that target amines, sulfhydryls, carboxyls, carbonyls or hydroxyls; omobifunctional or heterobifunctional crosslinking reagent, variable spacer arm length or zero-length crosslinking reagents, cleavable or non-cleavable crosslinking reagents, reversible or irreversible crosslinking reagents, and photoreactive crosslinking reagents. Non-limiting examples of crosslinking reagents that may be used to crosslink protein complexes and/or protein complexes and nucleic acids may include formaldehyde, glutaraldehyde, UV-254, disuccinimidyl glutarate, psoralens and their derivatives such as aminomethyltrioxsalen, disuccinimidyl suberate, ethylene glycol bis[succinimidylsuccinate], a photoreactive amino acid such as photo-leucine or photo-methionine, and succinimidyl-diazirine, and other compounds known to those skilled in the art, including those described in the Thermo Scientific Pierce Cross-linking Technical Handbook, Thermo Scientific (2009) as available on the world wide web at piercenet.com/files/1601673_Cross-link_HB_Intl.pdf. The degree of crosslinking can and will vary depending on the application of a method of the invention, and may be experimentally determined.

In some embodiments, the sample to be analyzed is contacted with a protein-nucleic acid cross-linking agent, a nucleic acid-nucleic acid cross-linking agent, a protein-protein cross-linking agent or any combination thereof. By this method, proteins and/or nucleic acids that interact with chromatin DNA become cross-linked to the chromatin DNA, such that isolation of the cross-linked proteins and/or nucleic acids also isolated as a complex with fragmented (or tagmented as described herein) chromatin DNA to which they are bound. By this method, primary, secondary and tertiary interactions between chromatin associated factors and chromatin DNA can be discerned. In some embodiments, a chromatin-associated factor (e.g., TF) is cross-linked with chromatin DNA. In some embodiments, the chromatin-associated factor cross-linked to the chromatin DNA is contacted with a specific binding agent example after fragmentation (e.g., tagmentation using transposon end composition and transposase), for example an antibody, which may be attached to a solid support, that specifically binds to the chromatin-associated factor, for example to isolate the chromatic DNA by virtue of its interaction with the chromatin associated factor. In some embodiments, the chromatin DNA is released from the chromatin-associated factor (e.g. TF bound DNA), for example after fragmentation (e.g., tagmentation using transposon end composition and transposase), and the DNA fragments produced are analyzed. In some examples, size is used to isolate the DNA fragments. Isolation of the nucleic acid fragments can be accomplished by means of an affinity molecule after the release of the fragments.

In some embodiments, the chromatin sample is cross-linked with a reversible cross-linking agent. In some embodiments, the reversible cross-linking agent is formaldehyde. In some embodiments, the final formaldehyde concentration during cross-linking is about 0.05% to about 1%, such as about 0.05% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 0.05% to about 0.2%, about 0.05% to about 0.3%, about 0.05% to about 0.4%, about 0.05% to about 0.5%, about 0.05% to about 0.6%, about 0.1% to about 0.5%, about 0.1% to about 1%, or about 0.5%. In some embodiment, the cross-linking time is no more than about 10 min, such as no more than about any of 10, 9, 8, 7, 6, 5, 4, 3, 2, or 1 min. In some embodiment, the cross-linking time is about 1 to about 10 min, about 2 to about 10 min, about 3 to about 10 min, about 4 to about 10 min, about 5 to about 10 min, about 6 to about 10 min, about 7 to about 10 min, about 8 to about 10 min, or about 9 to about 10 min. In some embodiments, the cross-linking time is about 5 to about 10 min.

Fragmentation

When a chromatin of the invention is a fragment of a chromatin in a cell, any method of fragmenting a chromatin known in the art may be used. Such methods may include physical methods of fragmenting a chromatin, or enzymatic digestion of a nucleic acid sequence of a chromatin. In some embodiments, a fragment of a chromatin may be generated using enzymatic digestion of a nucleic acid sequence in chromatin. Non-limiting examples of enzymatic digestion may include random or sequence specific enzymatic digestion using restriction enzymes, nucleases (e.g., micrococcal nuclease (MNase)), combinations of restriction enzymes and nucleases, or combinations of nicking and other nucleases such as NEBNext™ fragmentase, which comprises a nicking enzyme that randomly generates nicks in double stranded DNA and another enzyme that cuts the strand opposite to the generated nicks. In some cases, the restriction enzyme has a restriction recognition site of 1, 2, 3, 4, 5, 6, 7, 8, or more than 8 bases long. The resulting sequence segments can vary in size. The resulting sequence segments may also comprise a single-stranded overhand at the 5' or 3' end.

In other embodiments, a fragment of a chromatin may be generated using a physical method of fragmenting a chromatin. Non-limiting examples of physical fragmenting methods that may be used to fragment a chromatin of the invention may include nebulization, sonication, and hydrodynamic shearing. In some embodiments, a fragment of a chromatin may be generated using nebulization. In other embodiments, a fragment of a chromatin may be generated using hydrodynamic shearing. In preferred embodiments, a fragment of a chromatin may be generated using sonication. During sonication, a sample comprising chromatin is subjected to ultrasonic waves, whose vibrations produce gaseous cavitations in the liquid that shear or break high molecular weight molecules such as chromatin through resonance vibration. Sonication methods that may be used to generate a chromatin of the invention are known in the art.

A fragment of a chromatin of the invention may comprise a nucleic acid sequence fragment and may be about 10 to about 10000, about 10 to about 50, about 50 to about 100, about 100 to about 150, about 100 to about 200, about 100 to about 300, about 100 to about 400, about 100 to about 500, about 100 to about 600, about 100 to about 700, about 100 to about 800, about 100 to about 900, about 100 to about 1000, about 100 to about 1500, about 100 to about 2000, about 100 to about 2500, about 100 to about 3000, about 100 to about 3500, about 100 to about 4000, about 100 to about 4500, about 100 to about 5000, about 100 to about 6000, about 100 to about 7000, about 100 to about 8000, about 100 to about 9000, about 100 to about 10000, about 500 to about 600, about 500 to about 700, about 500 to about 800, about 500 to about 900, about 500 to about 1000, about 500 to about 1500, about 500 to about 2000, about 200 to about 300, about 200 to about 400, about 200 to about 500, about 200 to about 600, about 200 to about 700, about 200 to about 800, about 200 to about 900, about 200 to about 1000, about 200 to about 1500, or about 200 to about 2000 bases long. In some embodiments, a chromatin of the invention may comprise a nucleic acid sequence fragment of about any of 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, 7000, 8000, 9000, or 10000 bases long or more.

Chromatin of the invention may comprise one or more nucleosomes. As such, a chromatin fragment of the invention may comprise about any one of 1, 2, 3, 4, 5, 6, 7, 8, 9, 10, 11, 12, 13, 14, 15, 16, 17, 18, 19, or 20 nucleosomes. In some embodiments, a chromatin fragment of the invention may comprise about 1, 2, 3, 4, 5, or about 6 nucleosomes.

Chromatin fragments of the present invention can be obtained from singe step, or multiple steps of fragmentation. In some embodiments, multiple steps (e.g. two steps) of fragmentation comprise the same fragmentation method described herein. In some embodiments, multiple steps of fragmentation comprise the same fragmentation method described herein but under different conditions (e.g., strength, duration, buffer). In some embodiments, multiple steps of fragmentation comprise different fragmentation methods described herein. In some embodiments, the chromatin sample (or cell sample) is pre-fragmented, for example, using sonication or enzymatic digestion, then "tagmented" using transposon end compositions comprising transposon end in the presence of a transposase described herein. In some embodiments, the chromatin sample (or cell sample) is directly "tagmented" using transposon end compositions comprising transposon end in the presence of a transposase described herein. "Tagmentation" makes use of the development of a hyperactive Tn5 transposase for simultaneous fragmentation and tagging (e.g. tagging with sample index tag, adaptor used for making sequencing library) of DNA (see e.g., Adey et al. (2010) *Genome Biol* 11, R119, WO2014/190214, WO2013078470). In some embodiments, after pre-fragmentation and before incubating with transposon end compositions in the presence of a transposase described herein (i.e. tagmentation), at least about 50% (such as at least about any of 50%, 55%, 60%, 65%, 70%, 75%, 80%, 85%, 90%, 95%, 97%, or 99%) of the pre-fragmented chromatin fragments are about 200 to about 5000 bp in length, such as about 200 to about 300 bp, about 200 to about 400 bp, about 200 to about 500 bp, about 200 to about 600 bp, about 200 to about 700 bp, about 200 to about 800 bp, about 200 to about 900 bp, about 200 to about 1000 bp, about 200 to about 1200 bp, about 200 to about 1400 bp, about 200 to about 1600 bp, about 200 to about 1800 bp, about 200 to about 2000 bp, about 200 to about 2500 bp, about 200 to about 3000 bp, about 200 to about 3500 bp, about 200 to about 4000 bp, about 200 to about 4500 bp, about 200 to about 5000 bp, about 500 to about 600 bp, about 500 to about 700 bp, about 500 to about 800 bp, about 500 to about 900 bp, about 500 to about 1000 bp, about 500 to about 1200 bp, about 500 to about 1400 bp, about 500 to about 1600 bp, about 500 to about 1800 bp, about 500 to about 2000 bp, about 500 to about 2500 bp, about 500 to about 3000 bp, about 500 to about 3500 bp, about 500 to about 4000 bp, about 500 to about 4500 bp, or about 500 to about 5000 bp. In some embodiments, after pre-fragmentation and before incubating with transposon end compositions in the presence of a transposase described herein, at least about 50% to about 95% of the pre-fragmented chromatin fragments are about 500 to about 2000 bp. In some embodiments, after inserting transposon end compositions comprising transposon end in the presence of a transposase described herein, at least about 50% (such as at least about any of 50%, 55%, 60%, 65%, 70%, 75%, 80%, 85%, 90%, 95%, 97%, or 99%) of the chromatin fragments (can be pre-fragmented or not pre-fragmented) are about 100 to about 5000 bp in length, such as about 100 to about 200 bp, about 100 to about 300 bp, about 100 to about 400 bp, about 100 to about 500 bp, about 100 to about 600 bp, about 100 to about 700 bp, about 100 to about 800 bp, about 100 to about 900 bp, about 100 to about 1000 bp, about 100 to about 1200 bp, about 100 to about 1400 bp, about 100 to about 1600 bp, about 100 to about 1800 bp, about 100 to about 2000 bp, about 100 to about 2500 bp, about 100 to about 3000 bp, about 100 to about 3500 bp, about 100 to about 4000 bp, about 100 to about 4500 bp, or about 100 to about 5000 bp. In some embodiments, after inserting transposon end compositions comprising transposon end in the presence of a transposase described herein, at least about 50% to about 95% of the chromatin fragments (can be pre-fragmented or not pre-fragmented) are about 100 to about 500 bp.

Fragmentation results may be verified by methods well-known in the art. For example, in order to verify whether most of the nucleic acid, in particular DNA, fragments are about 200 to about 700 base pairs long, or about 100 to about 500 bp long, fragment length may be tested using agarose gel electrophoresis.

Transposome Complex and Tagmentation

Transposable elements are discrete DNA segments that can repeatedly insert into a few or many sites in a host genome. Transposition occurs without need for extensive DNA sequence homology or host gene functions required in classical homologous recombination. An important step in embodiments of the method of the present invention is the use of an in vivo or in vitro transposition reaction to fragment and tag the target DNA to generate tagged DNA fragments, in a process called "tagmentation." The transposition reaction requires a transposase, a transposon end composition, and suitable reaction conditions.

In some embodiments, the method of this invention is exemplified by employing a transposome complex formed by a transposase (e.g., hyperactive Tn5 transposase) and transposon end composition(s) comprising transposon end (e.g., Tn5-type transposon end) (Goryshin, I. and Reznikoff, W. S., J. Biol. Chem., 273: 7367, 1998). In some embodiments, the invention is exemplified by employing a transposome complex formed by a MuA transposase and a Mu transposon end comprising R1 and R2 end sequences (Mizuuchi, K., Cell, 35: 785, 1983; Savilahti, H, et al., EMBO J., 14: 4893, 1995). However, any transposition system that is capable of inserting a transposon end in a random or in an almost random manner with sufficient efficiency to 5'-tag and fragment a target DNA for its intended purpose can be used in the present invention. Examples of transposition systems known in the art which could be evaluated for the present methods include but are not limited to Staphylococcus aureus Tn552 (Colegio O R et al., J. Bacteriol., 183: 2384-8, 2001; Kirby C et al., Mol. Microbiol., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbiol Immunol., 204: 27-48, 1996), Tn/O and IS10 (Kleckner N, et al., Curr Top Microbiol Immunol., 204: 49-82, 1996), Mariner transposase (Lampe D J, et al., EMBO J., 15: 5470-9, 1996), Tc1 (Plasterk R H, Curr Top Microbiol Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbiol. Immunol. 204: 1-26, 1996), retroviruses (Brown P O, et al., Proc Natl Acad Sci USA, 86: 2525-9, 1989), and retrotransposon of yeast (Boeke J D and Corces V G, Annu Rev Microbiol. 43: 403-34, 1989).

In some embodiments, a target chromatin is contacted with a transposon end composition comprising a tag after cell culture but before cell lysis. As such, a tag may be introduced into a cell before cell lysis. Methods of introducing a tag into a cell of the invention can and will vary depending on the type of cell, the tag, and the application of a method of the invention. For instance, a nucleic acid tag may be electroporated into a cell after culture. In other embodiments, a target chromatin is contacted with a transposon end composition comprising a tag after cell lysis. In some embodiments, a target chromatin is contacted with a transposon end composition comprising a tag after cell lysis and chromatin fragmentation. In some embodiments, a target chromatin is contacted with a transposon end composition comprising a tag during cell culture by incubating the transposon end composition comprising a tag in a cell of the invention during cell culture. In some embodiments, the cell is engineered to express a transposase.

In some embodiments, there is provided a transposon end composition comprising transposon end, further comprising an amplification tag and a restriction site tag, wherein the transposon end composition comprises, from 5' to 3': an amplification tag, a restriction site tag, and a transposon end. In some embodiments, there is provided a transposome complex comprising a transposase (e.g., Tn5) and any of the transposon end compositions described herein. In some embodiments, the transposase (e.g., Tn5) and any of the transposon end compositions described herein are pre-incubated to form the transposome complex. In some embodiments, the transposome complex comprises (or consists of) a transposase (e.g., Tn5) and two transposon end compositions described herein. In some embodiments, the transposon end is double-stranded. In some embodiments, the transposon end comprises separate transferred strand and non-transferred strand. In some embodiments, the transferred strand comprises (or consists of) transferred transposon end sequence comprising SEQ ID NO: 1. In some embodiments, the non-transferred strand comprises (or consists of) non-transferred transposon end sequence comprising SEQ ID NO: 2. In some embodiments, the one or more tags are at 5' of the transferred transposon end sequence and/or 3' of the non-transferred transposon end sequence. In some embodiments, the one or more tags are only at 5' of the transferred transposon end sequence. In some embodiments, the amplification tag is a single-strand nucleic acid. In some embodiments, the amplification tag is only at 5' of the transferred transposon end sequence. In some embodiments, the amplification tag comprises (or consists of) SEQ ID NO: 3. In some embodiments, the restriction site tag is a double-stranded nucleic acid. In some embodiments, the restriction site tag is a single-strand nucleic acid. In some embodiments, the restriction site tag is only at 5' of the transferred transposon end sequence. In some embodiments, the restriction site tag is deoxyUridine (U). In some embodiments, the transposon end composition comprising transposon end further comprises one or more of a sample index tag, an UMI tag, or an amplification facilitating tag. In some embodiments, the sample index tag, UMI tag, and/or amplification facilitating tag are only at 5' end of the transferred transposon end sequence. In some embodiments, the transposon end composition comprising transposon end comprises (or consists of) from 5' to 3': a sample index tag, an amplification tag, a restriction site tag, and a transposon end. In some embodiments, the transposon end composition comprising transposon end comprises (or consists of) from 5' to 3': a sample index tag, an UMI tag, an amplification tag, a restriction site tag, and a transposon end. In some embodiments, the transposon end composition comprising transposon end comprises (or consists of) from 5' to 3': an UMI tag, a sample index tag, an amplification tag, a restriction site tag, and a transposon end. In some embodiments, the transposon end composition comprising transposon end comprises (or consists of) from 5' to 3': an UMI tag, an amplification tag, a restriction site tag, and a transposon end. In some embodiments, the transposon end composition comprising transposon end comprises (or consists of) from 5' to 3': a sample index tag, an UMI tag, an amplification tag, a restriction site tag, an amplification facilitating tag, and a transposon end. In some embodiments, the transposon end composition comprising transposon end comprises (or consists of) from 5' to 3': an UMI tag, a sample index tag, an amplification tag, a restriction site tag, an amplification facilitating tag, and a transposon end. In some embodiments, the sample index tag is only at 5' of the transferred transposon end sequence. In some embodiments, the sample index tag comprises SEQ ID NO: 24. In some embodiments, the sample index tag comprises the nucleic acid sequence of any one of SEQ ID NO: 25-32. In some embodiments, the amplification facilitating tag is only at 5' of the transferred transposon end sequence. In some embodiments, the amplification facilitating tag comprises (or consists of) SEQ ID NO: 4. In some embodiments, the UMI tag is only at 5' of the transferred transposon end sequence. In some embodiments, the UMI tag comprises about 3 to about 20 nt (such as about 3 to about 20 nt, about 3 to about 18 nt, about 3 to about 15 nt, about 3 to about 12 nt, about 3 to about 10 nt, about 3 to about 8 nt, about 3 to about 6 nt, about 4 to about 9 nt, about 4 to about 7 nt, or about 5 nt random dNTP) random dNTP. In some embodiments, the UMI tag comprises (or consists of) SEQ ID NO: 38. In some embodiments, the transposon end composition comprising transposon end further comprises other additional tags, such as capture tag, detection tag, affinity tag, sequencing tag, transcription promoter domain, etc. In some embodiments, the transposase is wild-type Tn5. In some embodiments, the transposase, the transposase is a mutant form of Tn5. In some embodiments, the transposase is EZ-Tn5™.

The bidirectional design of the transposon end composition (comprising from 5' to 3': an amplification tag, a restriction site tag, and a transposon end) of the present invention allows almost 100% of the target DNA to be made into sequencing library (see FIG. 3). The target DNA can be, e.g., ChIPed DNA, input DNA, any double-stranded DNA (e.g. fragments), long PCR products, or chromatin DNA. Unlike current dual-transposon design (e.g., by Illumina, see FIG. 3), for which only when both ends of a double-stranded DNA are tagmented with different Tn5 transposome complex (or different dual-transposon end compositions) can the tagmented DNA be made into library for further analysis, the bidirectional transposon design of the present invention essentially avoids material loss, thus the starting material of ChIP-SMITH or tagmentation-seq experiment can be significantly reduced.

The methods provided herein are also compatible with other Tn5 transposome complexes, such as those from Nextera® DNA Library Preparation Kits, Epicentre® DNA Sample Prep Kit, or the ones described in Amini et al. (Nat Genet., 2014 December; 46(12):1343-9) (herein collectively referred to as "commercial Tn5 transposome complexes"). For example, the Tn5 transposome complexes (or "Tagment DNA Enzyme", "TDE1") from Nextera® DNA Library Preparation Kits comprise pre-assembled Tn5 with two different sets of transposon end compositions, each set comprises two transposon ends and different adaptor sequences. Only when a target DNA is tagmented with different Tn5 transposome complexes can the target DNA be amplified with the dual-indexed PCR primers, resulting in a DNA library with indexes on both 5' and 3' ends. Similarly, Epicentre® DNA Sample Prep Kit comprises pre-assembled Tn5 with two different transposon end composition, each comprising a transposon end and a different adaptor annealing sequence. Only when a target DNA is tagmented with two different transposon end compositions on both 5' and 3' ends can the target DNA be amplified by PCR primers, while an index tag can be present on one of the adaptors. The Tn5 transposome complexes described in Amini et al. comprise differentially indexed Tn5 transposome complexes (both transposon end compositions within a single transposome complex are differentially indexed on the adaptors), the tagmented DNA fragments (when tagmented with different indexed adaptors) can then be made into DNA libraries with PCR primers carrying two additional indexes.

When the above commercial Tn5 transposome complexes are employed, the methods provided herein are still applicable with certain modifications.

For example, in some embodiments, there is provided a method of analyzing the binding sequences on a chromosome to which a protein of interest binds, comprising: (a) randomly inserting a plurality of transposon end compositions comprising transposon end into the chromatin or double-stranded nucleic acid fragments thereof (e.g., chromatin DNA) in the presence of a Tn5 transposase, wherein the transposon end compositions and the Tn5 transposase form a commercial Tn5 transposome complex (e.g., Tn5 transposome complexes similar to those from Nextera® DNA Library Preparation Kits, Epicentre® DNA Sample Prep Kit, or Amini et al.); (b) subjecting the double-stranded nucleic acid fragments inserted with transposon end compositions comprising transposon end to immunoprecipitation using a binding agent (e.g., an antibody or fragments thereof) specifically recognizing the protein of interest (e.g., for use in next-generation sequencing); and (c) analyzing the nucleic acid fragment sequences to which the protein of interest binds. In some embodiments, the chromatin sample is cross-linked. In some embodiments, the chromatin sample is not cross-linked (native chromatin). In some embodiments, the method comprises: incubating the chromatin (native or cross-linked) in an in vitro or in vivo transposition reaction with commercial Tn5 transposome complex, under conditions and for sufficient time wherein multiple insertions into the target DNA occur, each of which results in joining of a transposon end composition to at least one end of the target DNA, thereby fragmenting the chromatin (or chromatin DNA) and generating a population of tagged chromatin (or chromatin DNA) fragments. In some embodiments, when tagmenting the chromatin with the transposon end composition and transposase, the double-stranded chromatin DNA is tagged on one end with transposon end composition X, and on the other end with transposon end composition Y. The 5'-tagged and/or 3'-tagged chromatin (or chromatin DNA) is immunoprecipitated with a binding agent (e.g., an antibody or fragments thereof) specifically recognizing the protein of interest, then reverse-crosslinked at regular reverse-crosslinking temperature without denaturation (e.g., ~65° C.). These recovered 5'-tagged and/or 3'-tagged target DNA fragments can be subjected to further manipulation (e.g., cleanup, amplification, generating sequencing library for sequencing). In some embodiments, the commercial Tn5 transposome complex comprises transposon end composition(s) comprising index tag (e.g., Indexed Tn5 transposome complex as in Amini et al.). Thus, different biological samples can be tagmented with different transposon end compositions carrying different sample index, then pooled together for later immunoprecipitation. In some embodiments, before randomly inserting the transposon end compositions (tagmenting), the sample chromatin is pre-fragmented, e.g. mildly sheared by sonication. In some embodiments, the index tag is added after recovering the reverse-crosslinked target DNA, e.g., when adding an indexed adaptor (e.g. as in Epicentre® DNA Sample Prep Kit), or when PCR amplifying the reverse-crosslinked target DNA (e.g. as in Nextera® DNA Library Preparation Kits and Amini et al.).

In some embodiments, there is provided a method of analyzing the binding sequences on a chromosome to which a protein of interest binds, comprising: (a) immunoprecipitating the chromatin using a binding agent (e.g., an antibody or fragments thereof) specifically recognizing the protein of interest; (b) randomly inserting a plurality of transposon end compositions comprising transposon end into the chromatin or double-stranded nucleic acid fragments thereof (e.g., chromatin DNA) in the presence of a Tn5 transposase, wherein the transposon end compositions and the Tn5 transposase form a commercial Tn5 transposome complex (e.g., Tn5 transposome complexes similar to those from Nextera® DNA Library Preparation Kits, Epicentre® DNA Sample Prep Kit, or Amini et al.); (c) analyzing the nucleic acid fragment sequences to which the protein of interest binds. In some embodiments, the chromatin sample is cross-linked. In some embodiments, the chromatin sample is not cross-linked (native chromatin). In some embodiments, before ChIP, the sample chromatin is pre-fragmented, e.g. mildly sheared by sonication. In some embodiments, the binding agent bound chromatin is mildly fragmented (e.g., mildly sonication to avoid disrupting the interaction between the binding agent and chromatin) before inserting transposon end compositions. Since different samples are ChIPed first then tagmented with the transposon end compositions in these embodiments, different sample (if without other distinguishing labeling) may not be pooled together during ChIP, but can be differentially tagmented with transposon end compositions comprising different index tags (e.g., using the commercial Tn5 transposase complex from Amini et al.), then pooled together for later DNA recovery and library preparation. In some embodiments, the method comprises: incubating the chromatin (native or cross-linked) bound by immunoprecipitating binding agent (e.g., an antibody or fragments thereof) in an in vitro transposition reaction with commercial Tn5 transposome complex, under conditions and for sufficient time wherein multiple insertions into the target DNA occur, each of which results in joining of a transposon end composition to at least one end of the target DNA (e.g., chromatin DNA), thereby fragmenting the binding agent-bound chromatin (or chromatin DNA) and generating a population of one end or both ends tagged binding agent-bound chromatin (or chromatin DNA) fragments. In some embodiments, when tagmenting the binding agent-bound chromatin with the commercial Tn5 transposome complex, the double-stranded chromatin DNA is tagged on one end with a transposon end composition X, and on the other end with a transposon end composition Y. The tagged binding agent-bound chromatin (or chromatin DNA) is isolated, e.g. recovering chromatin-antibody-bead complex, then reverse-crosslinked without denaturation at normal reverse-crosslinking temperature (e.g., ~65° C.), resulting in 5'-tagged and/or 3'-tagged DNA fragments. These tagged DNA fragments can be subjected to further manipulation (e.g., cleanup, amplification, generating sequencing library for sequencing). In some embodiments, the index tag is added after recovering the reverse-crosslinked target DNA, e.g., when adding an indexed adaptor (e.g. as in Epicentre® DNA Sample Prep Kit), or when PCR amplifying the reverse-crosslinked target DNA (e.g. as in Nextera® DNA Library Preparation Kits and Amini et al.).

In some embodiments, there is provided a method of fragmenting (e.g., tagmenting) chromatin or naked dsDNA, comprising randomly inserting a plurality of transposon end compositions comprising transposon end into the chromatin or naked dsDNA in the presence of a Tn5 transposase, wherein the transposon end compositions and the Tn5 transposase form a commercial Tn5 transposome complex (e.g., Tn5 transposome complexes similar to those from Nextera® DNA Library Preparation Kits, Epicentre® DNA Sample Prep Kit, or Amini et al.). In some embodiments, the chromatin is cross-linked. In some embodiments, the chromatin sample is not cross-linked (native chromatin). In some embodiments, the method comprises: incubating the chromatin (native or cross-linked) or naked dsDNA in an in vitro or in vivo transposition reaction with the commercial Tn5 transposome complex, under conditions and for sufficient time wherein multiple insertions into the chromatin or naked dsDNA occur, each of which results in joining of a transposon end composition to at least one end of a nucleotide in the chromatin or naked dsDNA, thereby fragmenting the chromatin (or dsDNA) and generating a population of tagged chromatin (or 5'-tagged dsDNA) fragments, each of which has a transposon end composition on at least one end. In some embodiments, when tagmenting the chromatin or naked dsDNA with the commercial Tn5 transposome complex, the double-stranded DNA (chromatin DNA or naked DNA) is tagged on one end with a transposon end composition X, and on the other end with a transposon end composition Y. These 5'-tagged and/or 3'-tagged chromatin (or chromatin DNA) fragments can be subjected to any desired purposes or proper methods described herein. Similarly, the 5'-tagged and/or 3'-tagged naked dsDNA fragments can also be subjected to any desired purposes or proper methods described herein.

For example, in one embodiments, there is provided a method of preparing sequencing library starting from ChIPed DNA, input DNA, dsDNA, or any nucleic acid (e.g., RNA can be reverse transcribed and made into dsDNA), comprising contacting the dsDNA sample with transposon end compositions comprising transposon end in the presence of a Tn5 transposase, wherein the transposon end compositions and the Tn5 transposase form a commercial Tn5 transposome complex (e.g., Tn5 transposome complexes similar to those from Nextera® DNA Library Preparation Kits, Epicentre® DNA Sample Prep Kit, or Amini et al.), thus inserting the transposon end compositions into the dsDNA sample, generating tagged nucleic acid fragments. In some embodiments, the method comprises: incubating the dsDNA of interest in an in vitro or in vivo transposition reaction with the commercial Tn5 transposome complex under conditions and for sufficient time wherein multiple insertions into the target DNA occur, each of which results in joining of a transposon end composition to at least one end of the target DNA, thereby fragmenting the target DNA and generating a population of 5'-tagged and/or 3'-tagged dsDNA fragments, each of which has a transposon end composition on at least one end. In some embodiments, when tagmenting the dsDNA with the commercial transposome complex, the double-stranded DNA is tagged on one end with a transposon end composition X, and on the other end with a transposon end composition Y. These tagged DNA fragments can be subjected to further manipulation (e.g., cleanup, amplification, generating sequencing library for sequencing). In some embodiments, the commercial Tn5 transposome complex comprises a transposon end composition comprising an index tag (e.g., using similar indexed Tn5 from Amini et al.), thus different DNA samples can be first tagmented with different transposon end compositions carrying different index tags, then pooled together for later amplification. In some embodiments, the index tag is added using an indexed adaptor (e.g. as in Epicentre® DNA Sample Prep Kit), or when PCR amplifying the target DNA using indexed PCR primers (e.g. as in Nextera® DNA Library Preparation Kits and Amini et al.).

In some embodiments, there is provided a method of sequencing a nucleic acid sequence on a chromosome, comprising: (a) randomly inserting a plurality of transposon end compositions comprising transposon end into the chromatin or double-stranded nucleic acid fragments thereof (e.g., chromatin DNA) in the presence of a Tn5 transposase wherein the transposon end compositions and the Tn5 transposase form a commercial Tn5 transposome complex (e.g., Tn5 transposome complexes similar to those from Nextera® DNA Library Preparation Kits, Epicentre® DNA Sample Prep Kit, or Amini et al.); and (b) determining the nucleic acid fragment sequences. In some embodiments, the chromatin sample is cross-linked. In some embodiments, the chromatin sample is not cross-linked (native chromatin). In some embodiments, the method comprises: incubating the chromatin (native or cross-linked) in an in vitro or in vivo transposition reaction with the commercial Tn5 transposome complex under conditions and for sufficient time wherein multiple insertions into the target DNA (e.g., chromatin DNA) occur, each of which results in joining of a transposon end composition to at least one end of the target DNA, thereby fragmenting the chromatin (or chromatin DNA) and generating a population of 5'-tagged and/or 3'-tagged chromatin (or chromatin DNA) fragments. In some embodiments, when tagmenting the chromatin with the commercial Tn5 transposome complex, the double-stranded chromatin DNA is tagged on one end with a transposon end composition X, and on the other end with a transposon end composition Y. In some embodiments, the 5'-tagged and/or 3'-tagged chromatin (or chromatin DNA) is immunoprecipitated with a binding agent (e.g., an antibody or fragments thereof) specifically recognizing the protein of interest, then reverse-crosslinked at regular reverse-crosslinking temperature without denaturation (e.g., e.g. 65° C.), resulting in tagged DNA fragments. These tagged DNA fragments can be subjected to further manipulation (e.g., cleanup, amplification, generating sequencing library for sequencing). For example, this can be done after chromatin has been mildly pre-digested with MNase, and the transposome complexes are merely used to tagging the digested chromatin, rather than further fragmenting harshly. These tagged chromatin fragments can be studied for, e.g., nucleosome occupancy or positioning. In some embodiments, the transposon end compositions comprise an index tag. Thus, different biological samples can be tagmented with different transposon end compositions carrying different index tags, then pooled together for later experiments (e.g. ChIP). In some embodiments, before randomly inserting the transposon end compositions (tagmenting), the sample chromatin is pre-fragmented, e.g. mildly sheared by sonication or MNase. In some embodiments, the index tag is added after recovering the reverse-crosslinked target DNA, e.g., when adding an indexed adaptor (e.g. as in Epicentre® DNA Sample Prep Kit), or when PCR amplifying the reverse-crosslinked target DNA using indexed PCR primers (e.g. as in Nextera® DNA Library Preparation Kits and Amini et al.).

In some embodiments, the method further comprises the step of non-selectively amplifying the di-tagged (both 5'- and 3'-tagged) DNA fragments using a thermostable DNA polymerase and at least one primer that is complementary to the 5' and/or 3' transposon end composition (or its portion/complement). In some embodiments, the adaptors, PCR primers compatible with the commercial Tn5 transposome complex (e.g., adaptors, or PCR primers from Nextera® DNA Library Preparation Kits, Epicentre® DNA Sample Prep Kit, or Amini et al.) are employed.

In some preferred embodiment of any of the methods of the invention, the library of DNA fragments is used to provide templates for DNA sequencing or nucleic acid amplification.

Transposase

The method for inserting a transposon end into a target sequence can be carried out in vitro using any suitable transposon system for which a suitable in vitro transposition system is available or that can be developed based on knowledge in the art. In general, a suitable in vitro transposition system for use in the methods of the present invention requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase. Exemplary transposases include wild-type or mutant forms of Tn5 transposase and MuA transposase, but any other transposase for which compositions and conditions for efficient in vitro transposition of defined transposon ends are known or subsequently developed can be used in the present methods. Transposon end sequences recognized by wild-type or mutant forms of Tn5 transposase or MuA transposase are preferred, and those transposon end sequences that result in the highest transposition efficiencies when complexed with the transposase, together with the corresponding optimally active transposase enzymes that complex with them, are most preferred for embodiments of the present invention. In some embodiments, a transposon is chosen wherein the transposase end sequence required by the transposase for transposition is not too large and the transposon end sequences are of the minimal size possible that function well for the intended purpose and that are of sufficient size so that the same sequence is present only rarely or preferably, is not present at all, in the target DNA or sample DNA. By way of example, the transposon end sequences of the Tn5-derived EZ-Tn5™ transposon end sequences comprise only 19 nucleotides, whereas some other transposases require much larger end sequences for transposition (e.g., MuA transposase required transposon end sequences of approximately 51 nucleotides).

Suitable in vitro transposition systems that can be used to insert a transposon end into a target nucleic acid include, but are not limited to, those that use the EZ-Tn5™ hyperactive Tn5 Transposase available from EPICENTRE Technologies, Madison, Wis., or the HyperMu™ Hyperactive MuA Transposase from EPICENTRE or another MuA Transposase, such as that available from Finnzymes Oy, Espoo, Finland. Transposon end oligonucleotides that exhibit the sequences of the respective transposon ends can be synthesized using an oligonucleotide synthesizer or purchased from a commercial source based on information available from the respective vendors or using information well known in the art. For example, information related to EZ-Tn5™ transposase is available in the published literature from EPICENTRE Biotechnologies, Madison, Wis., USA.

In some embodiments, the insertion of a transposon end into target DNA according to the present invention can also be carried out in vivo. If transposition is carried out in vivo, transposition into the target DNA is preferably achieved by electroporating a synaptic complex of a transposase and a suitable transposon end composition into the host cell as described in U.S. Pat. No. 6,159,736 (herein incorporated by reference). This transposition method is exemplified by employing a transposition complex formed by a hyperactive Tn5 transposase and a suitable Tn5-type transposon end composition using methods similar to those described by (Goryshin, I. and Reznikoff, W. S. (J. Biol. Chem., 273: 7367, 1998) or a transposition complex formed by HyperMu™ Hyperactive MuA Transposase (EPICENTRE, Madison, Wis.) and a suitable MuA transposon end composition that exhibits the R1 and R2 end sequences recognized by the transposase. Suitable synaptic complexes or "Transposome™ complexes (EPICENTRE) between a transposon end composition and a transposase can be made as described in U.S. Pat. No. 6,159,736 and related patents of Goryshin and Reznikoff, or as described in product literature for Tn5-type EZ-Tn5™ Transposome™ complexes or for HyperMu™ MuA Transposome™ complexes from EPICENTRE Technologies, Madison, Wis., except that oligonucleotides that exhibit only one transposon end are used instead of a polynucleotide or oligonucleotide that has two transposon ends, usually at or near each end of the respective polynucleotide or oligonucleotide.

In some cases, the cell sample can be permeabilized to allow access for the transposase. The permeabilization can be performed in a way to minimally perturb the nuclei in the cell sample. In some embodiments, the cell sample can be permeabilized using a permeabilization agent. Examples of permeabilization agents include, but are not limited to, NP40, digitonin, tween, streptolysin, and cationic lipids. In some embodiments, the cell sample can be permeabilized using hypotonic shock and/or ultrasonication. In some embodiments, the transposase can be highly charged, which may allow it to permeabilize through cell membranes.

In some cases, the transposase can insert the nucleic acid sequence into the polynucleotide in a substantially sequence-independent manner. The transposase can be prokaryotic or eukaryotic. Examples of transposase include, but are not limited to, a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnlO, Tyl, any prokaryotic transposase, or any transposase related to and/or derived from those listed above. In some embodiments, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is about 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$. In some embodiments, the transposase is from bacteria, e.g. *E. coli*. In some embodiments, the transposase is Tn5. In some embodiments, the transposase is a hyperactive Tn5 transposase (e.g., EZ-Tn5™ Transposase, EPICENTRE Biotechnologies, Madison, Wis., USA).

Tn5 is a class II "cut and paste" transposable element isolated from gram negative bacteria. Catalysis involves nicking of DNA to generate nucleophilic 3'OH groups on both strands at the ends of the Tn5 transposase DNA recognition sequence. The 5' ends are also cleaved within the synaptic complex, releasing the transposable element from the donor DNA. This mechanism allows for the formation of a stable complex between the enzyme and transposon in the absence of $Mg^{2+}$, and is the basis for the transposase technologies developed by Epicentre Biotechnology (Madison, Wis., USA).

Tn5-mediated transposition is random, causing a small 9 bp duplication of the target sequence immediately adjacent to the insertion site. The result is analogous to using a restriction endonuclease with random sequence specificity that also contains a ligase activity. Epicenter's EZ-Tn5 Transposome™ technology utilizes a transposase-transposon complex which exhibits 1,000 fold greater activity than wild-type Tn5, achieved by combining a mutated recombinant Tn5 transposase enzyme with two synthetic oligonucleotides containing optimized 19 bp transposase recognition sequence, and is the basis of Epicentre's Nextera™ product used to streamline NGS library preparation. Using such a recombinant enzyme (whether naturally occurring or engineered to have improved transposition activity), transposition occurs with at efficiencies of 0.5-5%, using as little as 50 ng of purified DNA, yielding>106 transpositions per reaction. The transposome is so stable that it can be introduced via electroporation into living organisms, both prokaryotic (Gram negative and Gram positive bacteria) and eukaryotic (yeast, trypanosome, and mice) where in the presence of endogenous $Mg^{2+}$, transposon insertion has shown to be random and stable. The ability of the Tn5 transposase to recognize eukaryotic chromatin as a substrate is extremely significant.

In some embodiments, the transposase can further comprise an affinity tag. In some cases, the affinity tag can be an antibody. In some embodiments, the antibody binds to, for example, a transcription factor, a modified nucleosome or a modified nucleic acid. Examples of modified nucleic acids include, but are not limited to, methylated or hydroxymethylated DNA. In some embodiments, the affinity tag can be a single-stranded nucleic acid (e.g., ssDNA, ssRNA). In some embodiments, the single-stranded nucleic acid can bind to a target nucleic acid. In some embodiments, the transposase can further comprise a nuclear localization signal.

Transposon End Composition

In some embodiments, the transposon end compositions comprise hairpin transposon ends. In some embodiments, the transposon ends (e.g. synthetic) or transposon end compositions comprise separate transferred strands and non-transferred strands. The transposon end composition in some embodiments comprises a transposon end, optionally plus additional sequence or sequences 5'-of the transferred transposon end sequence and/or 3'-of the non-transferred transposon end sequence. In some embodiments, the transposon end composition comprises or consists of two transposon end oligonucleotides consisting of the transferred transposon end oligonucleotide (or transferred strand) and the non-transferred strand end oligonucleotide (or non-transferred strand), which, in combination, exhibit the sequences of the transposon end, and in which one or both strand comprise additional sequence.

In some embodiments, the transposon ends (e.g. synthetic) or transposon end compositions comprise separate transferred strands and non-transferred strands. In some embodiments, the transferred strands comprise 5' tag domains, e.g., comprising or consisting of one or more of a restriction site domain, an amplification tag domain, an amplification facilitating tag domain, sample index tag domain, and a UMI tag domain. In some embodiments, the transferred strands further comprise 5' tag domains selected from one or more of a capture tag domain, a sequencing tag domain, a detection tag domain, an address tag domain, and a transcription promoter domain. For example, in some embodiments, the tag domain comprises sequencing tags comprising or consisting of a sequencing tag selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, and the Complete Genomics sequencing tags.

In some embodiments, the methods of the present invention produce tagged circular ssDNA fragments. In some embodiments, tagged circular ssDNA fragments exhibit only the sequence of the transferred strand of the transposon end composition, and the tagged circular ssDNA fragments do not exhibit the sequence of the non-transferred strand of the transposon end composition.

In some embodiments, the transposon end composition used in the method of the present invention comprises Mu transposon end oligonucleotides that exhibit only the transposon end sequences that form a complex with the transposase or integrase and that are needed for the transposition reaction; in these embodiments, the tag in the tagged circular ssDNA fragments generated using the method exhibits only the transferred transposon end sequence.

However, in some embodiments, the transposon end composition comprises or consists of at least one transposon end oligonucleotide that exhibits one or more other nucleotide sequences in addition to the transposon end sequences. Thus, in some embodiments, the transposon end composition comprises a transferred strand that exhibits one or more other nucleotide sequences 5'-of the transferred transposon end sequence, which one or more other nucleotide sequences are also exhibited by the tag. Thus, in addition to the transferred transposon end sequence, the tag can have one or more other tag portions or tag domains.

Thus, in some embodiments, the method or kit uses a transferred strand that has a 3' portion and a 5' portion, wherein the 3' portion exhibits the transferred transposon end sequence and the 5' portion exhibits one or more additional sequences that do not participate in forming a functional complex with the transposase. There is no limit to which additional sequences are used for the one or more additional sequences in the 5'-portion of the transferred strand, which sequences can be used to accomplish any desired purpose. For example, in some embodiments, the 5' portion of the transferred strand exhibits one or more additional tag sequences (e.g., a tag sequence that permits capture by annealing to a specific sequence on a surface, such as a bead or a probe on a microchip or array; e.g., for capture on a bead for next-generation sequencing; e.g., a 454A or 454B tag sequence for capture on the bead for sequencing using a Roche 454 Next-Gen sequencer) or one or more sequences for identification, detection (e.g., fluorescent detection), or sorting of the products of the method. In some other embodiments, the 5' portion of the transferred strand exhibits one or more additional nucleotides or sequences or a chemical group or moiety that comprises or consists of an affinity-binding that (e.g., a tag sequence that permits capture by annealing to a specific sequence on a surface, such as a bead or a probe on a microchip or array. In some preferred embodiments, the size of the one or more additional sequences in the 5'-portion of the transferred strand are minimized in order to minimize the probability or frequency of insertion of the transferred strand into itself during the in vitro or in vivo transposition reaction. For example, in some embodiments, the size of the 5'-portion of the transferred strand is less than about 150 nucleotides, less than about 100 nucleotides, less than about 75 nucleotides, less than about 50 nucleotides, less than about 40 nucleotides, less than about 30 nucleotides, less than about 25 nucleotides, less than about 20 nucleotides, or less than about 15 nucleotides. In some embodiments, the size of the 5'-portion of the transferred strand is about 32 nucleotides.

In some embodiments, the 5'-end of the transferred strand has a 5'-monophosphate group. In some embodiments, both the transferred strand and the non-transferred strand have a 5'-monophosphate group. In some preferred embodiments, only the 5'-end of the non-transferred strand has a 5'-monophosphate group. In some other embodiments, there is no 5'-monophosphate group on the 5'-end of the transferred strand.

1) Transposon End

In some embodiments the transposon ends comprise Mu transposon ends and the transposase is Mu transposase. In some preferred embodiments, the 3' portions of the transferred strands comprise a sequence from a Mu transposon end, and wherein the 5' portions of the transferred strands are not from a Mu transposon.

In some embodiments the transposon ends comprise Tn5 transposon ends and the transposase is Tn5 transposase (e.g., EZ-Tn5™ transposase). In some embodiments, the 3' portions of the transferred strands comprise a sequence from a Tn5 transposon end, and wherein the 5' portions of the transferred strands are not from a Tn5 transposon. In some embodiments, the 5' portions of the transferred strands comprise a sequence from a Tn5 transposon end, and wherein the 3' portions of the transferred strands are not from a Tn5 transposon. In some embodiments, both the 3' portions and the 5' portions of the transferred strands are from a Tn5 transposon. In some embodiments, neither the 3' portions nor the 5' portions of the transferred strands are from a Tn5 transposon.

In some embodiments, the transposon end forms a complex with a hyperactive Tn5 transposase (e.g., EZ-Tn5™ Transposase, EPICENTRE Biotechnologies, Madison, Wis., USA) in an in vitro or in vivo transposition reaction comprises a transferred strand that exhibits a "transferred transposon end sequence" comprising (and in some embodiments consisting of or consisting essentially of): 5' AGATGTGTATAAGAGACAG 3' (SEQ ID NO: 1), and a non-transferred strand that exhibits a "non-transferred transposon end sequence" comprising (and in some embodiments consisting of or consisting essentially of): 5' CTGTCTCTTATACACATCT 3' (SEQ ID NO: 2). The 3'-end of a transferred strand is joined or transferred to target DNA in an transposition reaction. The non-transferred strand, which exhibits a transposon end sequence that is complementary to the transferred transposon end sequence, is not joined or transferred to the target DNA in a transposition reaction. In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. In the embodiments where a hairpin structured transposon end is used, a cleavage is generated at the hairpin structure after tagmentation, in order to separate the hairpin structure as separate transferred strand and non-transferred strand, while still preserving desired tags on each desired strands, e.g., sample index tag and/or amplification tag will retain on the after-cut transferred strand.

In some embodiments, the transposon end comprises (and in some embodiments consists of or consists essentially of) separate transferred strand and non-transferred strand. In some embodiments, the transferred strand and non-transferred strand forms a double-stranded structure.

2) Amplification Tag and Amplification Facilitating Tag

In some embodiments, the transposon end composition comprises an amplification tag domain or amplification tag, which comprises (and in some embodiments consists of or consists essentially of) a sequence for the purpose of facilitating amplification of the nucleic acid to which said tag is appended. In some embodiments, the amplification tag is 5'-of the transferred transposon end sequence and/or 3'-of the non-transferred transposon end sequence. In some embodiments, the amplification tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction). In some embodiments, the amplification tag is only 5'-of the transferred transposon end sequence. In some embodiments, the amplification tag is at least about 80% (such as at least about any of 80%, 85%, 90%, 95%, 96%, 97%, 98%, or 99%) or 100% complementary to a library amplification primer described herein. In some embodiments, the amplification tag comprises about 9-30 nt, such as about 10-28 nt, about 10-26 nt, about 12-24 nt, about 14-20 nt, or about 15 nt. In some embodiments, the amplification tag comprises high GC content with a melting temperature Tm of about 60-70° C. (such as any of about 60-70° C., about 62-68° C., about 63-66° C., or about 65° C.) in NEB Q5® DNA polymerase buffer. In some embodiments, the amplification tag comprises (and in some embodiments consists of or consists essentially of) GACGCTGCCGACGA (SEQ ID NO: 3). In some embodiments, the amplification tag is 5' of the transferred transposon end sequence. In some embodiments, the amplification tag is 5' of the transferred transposon end sequence and 3' of an index tag domain described herein (such as a sample index tag domain, or an UMI tag domain, or 3' of both tag domains). In some embodiments, the transferred strand comprises from 5' to 3': amplification tag—restriction site tag—transferred transposon end sequence. In some embodiments, the transferred strand comprises from 5' to 3': index tag (e.g., sample index tag and/or UMI tag)—amplification tag—restriction site tag—transferred transposon end sequence. In some embodiments, the amplification tag is directly contiguous with the restriction site tag and/or UMI tag. In some embodiments, the amplification tag is separated from the restriction site tag and/or UMI tag by about any of 1, 2, 3, 4, 5, 6, 7, 8, 9, 10 or more than 10 nucleotides. In some embodiments, the amplification tag overlaps with the restriction site tag and/or UMI tag by about any of 1, 2, 3, 4, 5, 6, 7, 8, 9, 10 or more than 10 nucleotides.

In some embodiments, the transposon end composition further comprises an amplification facilitating tag domain or amplification facilitating tag, which comprises (and in some embodiments consists of or consists essentially of) a sequence for the purpose of facilitating amplification of the nucleic acid to which said tag is appended. In some embodiments, the amplification facilitating tag is 5'-of the transferred transposon end sequence and/or 3'-of the non-transferred transposon end sequence. In some embodiments, the amplification facilitating tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction). In some embodiments, the amplification facilitating tag is only 5'-of the transferred transposon end sequence. In some embodiments, the amplification facilitating tag is a small fragment that participates in template-primer base-pairing, but confers less specificity compared to the priming site sequence (e.g., the 5'-end of the primer is less critical for primer annealing than the 3'-end). In some embodiments, the amplification facilitating tag is at least about 20% (such as at least about any of 20%, 30%, 40%, 50%, 60%, 70%, 80%, 85%, 90%, 95%, 96%, 97%, 98%, or 99%) or 100% complementary to a library amplification primer described herein. In some embodiments, the amplification facilitating tag comprises about 1-30 nt, such as about 2-25 nt, about 2-20 nt, about 2-15 nt, about 2-10 nt, about 3-9 nt, about 3-6 nt, or about 5 nt. In some embodiments, the amplification facilitating tag comprises (and in some embodiments consists of or consists essentially of) CTCGG (SEQ ID NO: 4). In some embodiments, the amplification facilitating tag is 5' of the transferred transposon end sequence. In some embodiments, the amplification facilitating tag is 5' of the transferred transposon end sequence and 3' of an restriction site tag. In some embodiments, the transferred strand comprises from 5' to 3': amplification tag—restriction site tag—amplification facilitating tag—transferred transposon end sequence. In some embodiments, the transferred strand comprises from 5' to 3': index tag (e.g., sample index tag and/or UMI tag)—amplification tag—restriction site tag—amplification facilitating tag—transferred transposon end sequence. In some embodiments, the amplification facilitating tag is directly contiguous with the restriction site tag and/or transferred transposon end sequence. In some embodiments, the amplification facilitating tag is separated from the restriction site tag and/or transferred transposon end sequence by about any of 1, 2, 3, 4, 5, 6, 7, 8, 9, 10 or more than 10 nucleotides. In some embodiments, the amplification tag overlaps with the restriction site tag and/or transferred transposon end sequence by about any of 1, 2, 3, 4, 5, 6, 7, 8, 9, 10 or more than 10 nucleotides.

3) Restriction Site Tag

In some embodiments, the transposon end composition comprises a restriction site domain or restriction site tag, which exhibits a sequence for the purpose of facilitating cleavage. In some embodiments, the restriction site tag is 5'-of the transferred transposon end sequence and/or 3'-of the non-transferred transposon end sequence. In some embodiments, only the transferred strand comprises a restriction site tag on 5' end. In some embodiments, both the transferred and on-transferred strands comprise a restriction site tag, e.g., the restriction site tag domain is a double-stranded nucleic acid. Thus in some embodiments, the restriction site tag can be cleaved by restriction enzymes, e.g., HindIII.

For example, in some embodiments, the restriction site domain is used to generate di-tagged linear ssDNA molecules from tagged circular ssDNA molecules. In some embodiments, the restriction site tag comprises (and in some embodiments consists of or consists essentially of) deoxyUridine (U), and the methods of the invention comprise contacting the tagged circular ssDNA with an Uracil-Specific Excision Reagent (USER) Enzyme, to generate di-tagged linear ssDNA molecules. USER Enzyme is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. In some embodiments, the restriction site domain is used to generate a compatible double-stranded 5'-end in the tag domain so that this end can be ligated to another DNA molecule using a template-dependent DNA ligase. In some embodiments, the restriction site domain in the tag exhibits the sequence of a restriction site that is present only rarely, if at all, in the target DNA (e.g., a restriction site for a rare-cutting restriction endonuclease such as NotI or AscI). In some embodiments, the restriction site in the restriction site domain is for a type II restriction endonuclease, such as FokI restriction endonuclease.

In some embodiments, the restriction site tag is deoxyuridine (U), and the methods of the invention comprise contacting the tagged DNA with an USER Enzyme for cleavage. In some embodiments, the restriction site tag is deoxyuridine (U), and the methods of the invention comprise contacting the tagged DNA with a mixture of Uracil DNA glycosylase (UDG) and DNA glycosylase-lyase Endonuclease VIII.

In some embodiments wherein the transferred strand of the transposon end composition comprises one or more restriction site domains 5'-of the transferred transposon end sequence, the method further comprises: annealing an oligodeoxyribonucleotide that is complementary to the single-stranded restriction site of the tagged circular ssDNA fragments and then cleaving the tagged circular ssDNA fragments at the restriction site using the restriction endonuclease that recognizes the restriction site. Thus, in some embodiments, the method comprises linearizing the tagged circular ssDNA fragments to generate di-tagged linear ssDNA fragments.

In some other embodiments wherein the transferred strand of the transposon end composition comprises one or more restriction site domains 5'-of the transferred transposon end sequence, the transferred strand of the transposon end composition comprises a double-stranded hairpin comprising the restriction site, and the method further comprises the steps of cleaving the tagged linear ssDNA fragments at the restriction site using the restriction endonuclease that recognizes the restriction site.

In some embodiments comprising (i) generating a double-stranded restriction site, either by annealing of an oligodeoxyribonucleotide that is complementary to the single-stranded restriction site, or by using a transferred strand that comprises a double-stranded hairpin, and (ii) then cleaving the restriction site using the restriction endonuclease that recognizes the double-stranded restriction site, the method further comprises the step of ligating the restriction endonuclease-cleaved tagged linear ssDNA fragments to another DNA molecule that has a compatible 3'-end.

In some embodiments, the restriction site tag is 5'-of the transferred transposon end sequence and 3' of the amplification tag described herein. In some embodiments, the restriction site tag is directly contiguous with the (5') transferred transposon end sequence. In some embodiments, the restriction site tag is separated from the transferred strand by about any of 1, 2, 3, 4, 5, 6, 7, 8, 9, 10 or more than 10 nucleotides. In some embodiments, the restriction site tag overlaps with the transferred transposon end sequence by about any of 1, 2, 3, 4, 5, 6, 7, 8, 9, 10 or more than 10 nucleotides.

4) Sample Index Tag

In some embodiments, the transposon end composition comprises a sample index tag, which exhibits a sequence that permits identification of a specific sample (e.g., wherein the transferred strand has a different sample index tag domain that exhibits a different sequence for each sample). In some embodiments, the sample index tag is 5'-of the transferred transposon end sequence and/or 3'-of the non-transferred transposon end sequence. In some embodiments, only the transferred strand comprises a sample index tag. In some embodiments, the sample index tag comprises (and in some embodiments consists of or consists essentially of) about 3 to about 20 nt random dNTP, such as about 3 to about 18 nt, about 3 to about 15 nt, about 3 to about 12 nt, about 3 to about 10 nt, about 3 to about 8 nt, about 3 to about 6 nt, about 4 to about 9 nt, about 4 to about 7 nt, about 5 nt, or about 6 nt random dNTP. In some embodiments, the sample index tag comprises SEQ ID NO: 24. In some embodiments, the sample index tag comprises (and in some embodiments consists of or consists essentially of) any one of SEQ ID NOs: 25-32. It will be appreciated that the order of a sample index tag can be varied in the 5' tag domains of the transferred strand. For example, in some embodiments, the sample index tag is directly contiguous with and 5' of the amplification tag. In some embodiments, the sample index tag is separated from the amplification tag by about any of 1, 2, 3, 4, 5, 6, 7, 8, 9, 10 or more than 10 nucleotides. In some embodiments, the sample index tag overlaps with the amplification tag by about any of 1, 2, 3, 4, 5, 6, 7, 8, 9, 10 or more than 10 nucleotides. Any of the available barcode sequences used during sequencing (e.g. barcodes from NEB-Next® Multiplex Oligos for Illumina® Kit, Illumina® Multiplexing Sample Preparation Oligonucleotide Kit, or Nextera™ DNA Sample Prep Kits, KAPA DNA Library Preparation Kits, EpiNext DNA Library Preparation Kit, or PicoPLEX® DNA-seq Kit, etc.), or any combinations of A/T/G/C that can identify the samples while not affecting tagging/library preparation/sequencing, can be employed as sample index tag.

5) Unique Molecular Identifier (UMI) Tag

In some embodiments, the transposon end composition comprises a unique molecular identifier (UMI) that would allow for the detection of PCR duplicates. In some embodiments, the UMI tag is 5'-of the transferred transposon end sequence. In some embodiments, the 5' tag domains of a transferred strand comprises both an UMI tag and a sample index tag. It will be appreciated that the order of a sample index tag and an UMI tag can be varied in the 5' tag domains of the transferred strand. For example, in some embodiments, the sample index tag is positioned 3' to the UMI tag. In some embodiments, the sample index tag is positioned 5' to the UMI tag. In some embodiments, the sample index tag is directly contiguous with the UMI tag. In some embodiments, the sample index tag is separated from the UMI tag by about any of 1, 2, 3, 4, 5, 6, 7, 8, 9, 10 or more than 10 nucleotides. In some embodiments, the sample index tag overlaps with the UMI tag by about any of 1, 2, 3, 4, 5, 6, 7, 8, 9, 10 or more than 10 nucleotides. In some embodiments, the UMI comprises (and in some embodiments consists of or consists essentially of) about 3 to about 20 nt random dNTP, such as about 3 to about 20 nt, about 3 to about 18 nt, about 3 to about 15 nt, about 3 to about 12 nt, about 3 to about 10 nt, about 3 to about 8 nt, about 3 to about 6 nt, about 4 to about 9 nt, about 4 to about 7 nt, or about 5 nt random dNTP. In some embodiments, the UMI tag comprises about 5 nt random dNTP. In some embodiments, the 3'-of the non-transferred strand of the transposon end composition also comprises an UMI tag. In some embodiments, only the transferred strand comprises a 5' UMI tag. In some embodiments, the UMI comprises (and in some embodiments consists of or consists essentially of) SEQ ID NO: 38.

6) Additional Tags

In some embodiments, the transposon end composition described here further comprises an "affinity tag". Affinity tags can be useful for the bulk separation of target nucleic acids. As used herein, the term "affinity tag" and grammatical equivalents can refer to a component of a multi-component complex, wherein the components of the multi-component complex specifically interact with or bind to each other. For example, an affinity tag can include biotin or His that can bind streptavidin or nickel, respectively. Other examples of multiple-component affinity tag complexes include, ligands and their receptors, for example, avidin-biotin, streptavidin-biotin, and derivatives of biotin, streptavidin, or avidin, including, but not limited to, 2-iminobiotin, desthiobiotin, NeutrAvidin, CaptAvidin, and the like; binding proteins/peptides, including maltose-maltose binding protein (MBP), calcium-calcium binding protein/peptide (CBP); antigen-antibody, including epitope tags, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; and the like.

In some embodiments, the transposon end composition further comprises a "capture tag domain" or a "capture tag," which exhibits a sequence for the purpose of facilitating capture of the DNA fragment to which the tag domain is joined (e.g., to provide an annealing site or an affinity tag for a capture of the tagged DNA fragments or the di-tagged linear ssDNA fragments on a bead or other surface, e.g., wherein the annealing site of the tag domain sequence permits capture by annealing to a specific sequence which is on a surface, such as a probe on a bead or on a microchip or microarray or on a sequencing bead). In some embodiments of the method, after the tagged circular ssDNA fragments or the di-tagged linear ssDNA fragments are captured by annealing to a complementary probe on a surface, the capture tag domain provides a site for priming DNA synthesis using said tagged circular ssDNA fragments or said di-tagged linear ssDNA fragments (or the complements of said tagged circular ssDNA fragments or di-tagged linear ssDNA fragments) as templates. In some other embodiments, the capture tag domain comprises a 5'-portion of the transferred strand that is joined to a chemical group or moiety that comprises (and in some embodiments consists of or consists essentially of) an affinity binding molecule (e.g., wherein the 5'-portion of the transferred strand is joined to a first affinity binding molecule, such as biotin, streptavidin, an antigen, or an antibody that binds the antigen, that permits capture of the tagged DNA fragments or the di-tagged linear ssDNA fragments on a surface to which a second affinity binding molecule is attached that forms a specific binding pair with the first affinity binding molecule).

In some embodiments, the transposon end composition further comprises a "sequencing tag domain" or a "sequencing tag," which exhibits a sequence for the purposes of facilitating sequencing of the DNA fragment to which the tag is joined (e.g., to provide a priming site for sequencing by synthesis, or to provide annealing sites for sequencing by ligation, or to provide annealing sites for sequencing by hybridization). For example, in some embodiments, the sequencing tag domain provides a site for priming DNA synthesis of an ssDNA fragment or the complement of a ssDNA fragment. In some embodiments of the methods described herein, the sequencing tag domains comprise or consist of sequencing tags selected from Roche 454A and 454B sequencing tags, ILLUMINA™ SOLEXA™ sequencing tags, Applied Biosystems' SOLID™ sequencing tags, the Pacific Biosciences' SMRT™ sequencing tags, Pollonator Polony sequencing tags, the Complete Genomics sequencing tags, the INTELLIGENT BIOSYSTEMS' sequencing platform sequencing tags, or the HELICOS sequencing platform sequencing tags.

In some embodiments, the transposon end composition further comprises a "detection tag domain" or a "detection tag," which exhibits a sequence or a detectable chemical or biochemical moiety for the purpose of facilitating detection of the tagged DNA fragments or the di-tagged linear ssDNA fragments (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art).

In some embodiments, the transposon end composition further comprises a "transcription promoter domain" (or a promoter domain), which exhibits a sequence for a sense promoter sequence or for an anti-sense promoter sequence of an RNA polymerase promoter. As used herein, a "sense promoter sequence" means the sequence of an RNA polymerase promoter that is joined to the DNA strand that serves as the template for transcription by an RNA polymerase which binds the RNA polymerase promoter and initiates transcription therefrom under reaction conditions suitable for transcription. As used herein, an "anti-sense promoter sequence" means the sequence of an RNA polymerase promoter that is complementary to the sense promoter sequence. In some embodiments, the sense promoter sequence exhibited by the transcription promoter domain is for an RNA polymerase that binds a single-stranded RNA polymerase promoter and initiates transcription therefrom, in which embodiments the sense promoter sequence is sufficient to function as the RNA polymerase promoter (e.g., for bacteriophage N4 RNA polymerase). In some embodiments, the sense promoter sequence is for an RNA polymerase that binds a double-stranded RNA polymerase promoter and initiates transcription therefrom, in which embodiments the method comprises making the RNA polymerase promoter double-stranded (e.g., by annealing to the sense promoter sequence an oligodeoxyribonucleotide that exhibits an anti-sense promoter sequence that is complementary to the sense promoter sequence, or by using a tagged circular ssDNA fragments or the di-tagged linear ssDNA fragments as templates for synthesis of dsDNA comprising (or consisting) of the sense promoter sequence) prior to transcription using an RNA polymerase that binds to and initiates transcription from the double-stranded RNA polymerase promoter. In some embodiments, the sense promoter sequence is for a T7-type RNA polymerase (e.g., selected from among T7 RNA polymerase, T3 RNA polymerase, and SP6 RNA polymerase). A transcription promoter domain that exhibits a sense promoter sequence enables synthesis of RNA that is complementary to the single-stranded target DNA to which the transferred strand of the transposon end composition is ligated using the method. Tagged circular ssDNA fragments generated using a transposon end composition comprising a transferred strand that has a transcription promoter domain that exhibits an anti-sense promoter sequence cannot be transcribed by an RNA polymerase. However, in some embodiments, dsDNA synthesized by extending a primer that anneals to the tagged circular ssDNA fragments is used for transcription by an RNA polymerase that binds to and initiates transcription from a double-stranded RNA polymerase promoter; in these embodiments, the RNA synthesized exhibits the same sequence as the tagged circular ssDNA fragments.

Immunoprecipitating Binding Agents and Beads

In some embodiments, the binding agent used for immunoprecipitating protein of interest can be a polypeptide, such as a protein or fragments thereof, in particular an antibody, or antigen-binding fragment; a nucleic acid, e.g. an oligonucleotide, polynucleotide, and the like; or a small molecule, e.g. a chemical substance. For example, in some embodiments, the binding agent may have a methyl-CpG binding domain (MBD) recognizing chromatin. In some embodiments, the binding agent is a polypeptide, in particular an antibody or fragment thereof which specifically binds to chromatin, proteins, e.g. transcription factors, histones, modified histones, chromatin remodeler, chromatin modifier (e.g. histone modifier), transcription machinery elements (e.g. RNA Pol II), insulator binding protein such as CTCF, associated directly or indirectly with chromatin and/or DNA. In some embodiments, the binding agent is a molecule that can bind to the affinity tag described herein comprised within the transposon end composition. For example, in some embodiments, the affinity tag is a His tag, and the binding agent used for capturing tagmented chromatin (or DNA) is an anti-His antibody. In some embodiments, the affinity tag comprises biotin, and the binding agent used for capturing tagmented chromatin (or DNA) comprises streptavidin.

In some embodiments, the immunoprecipitating binding agent is an antibody. Such antibodies can specifically recognize any of the protein of interest described herein, e.g., an antibody specifically recognizing elongating format of RNA Pol II. In some embodiments, the antibody is a full-length antibody that comprises an Fc fragment, such as IgA, IgD, IgE, IgG, IgM, or immunoglobulin derivatives. In some embodiments, the antibody is an antigen-binding fragment, e.g., a Fab, a Fab', a F(ab')2, an Fv fragment, a disulfide stabilized Fv fragment (dsFv), or a single-chain Fv (scFv). Any antibody or antigen-binding fragment can be used in the present invention, as long as chromatin bound by the antibody or antigen-binding fragment can be recovered, e.g., captured by ChIP beads. In some embodiments, the antibody is monospecific. In some embodiments, the antibody is multispecific (such as bispecific). Multispecific antibodies have binding specificities for at least two different antigens or epitopes. In some embodiments, the antibody is monoclonal. In some embodiments, the antibody is polyclonal. In some embodiments, the antibody is ChIP-grade, or at least IP grade or western blot grade. The antibody can react with protein of interest from any organism, such as human, mouse, rabbit, rat, monkey, fruit fly, zebrafish, chicken, worms, bacteria, etc. In some embodiments, the antibody is chimeric, mouse, rabbit, rat, sheep, human, partially humanized, fully humanized, semi-synthetic, or fully-synthetic antibody.

In some embodiments, the methods of the invention comprise, subsequent to the above described chromatin fragmentation step (e.g., mild shearing by sonication) and tagmentation step using transposase and transposon end compositions described herein, an immunoprecipitating binding agent, such as an antibody or a chemical substance, is added to the sample comprising tagmented chromatin (e.g., chromatin DNA). In some other embodiments, the methods of the invention comprise, subsequent to the above described chromatin fragmentation step (e.g., shearing by sonication), an immunoprecipitating binding agent, such as an antibody or a chemical substance, is added to the sample comprising fragmented chromatin (e.g., chromatin DNA), then the chromatin fragments recognized by the binding agent are isolated, and further tagmented with transposase and transposon end compositions described herein. In the latter case, by isolating chromatin bound by said binding agent, in particular, by isolated binding agent-bound chromatin from unbound chromatin, the overall amount of chromatin subjected to tagmentation is significantly reduced, which reduces tagmentation events.

In some embodiments, one or more immunoprecipitating binding agents are used for precipitating chromatin comprising protein of interest. For example, one or more antibodies specifically recognizing different proteins of interest can be used together for chromatin pull-down, e.g., antibodies specifically recognizing histone H3 and H4 can be used together to pull-down nucleosome occupied nucleic acid, e.g., DNA wrapped around nucleosomes. In some embodiments, one or more antibodies specifically recognizing the same protein of interest can be used together for chromatin pull-down, e.g., different antibodies specifically recognizing the same protein (such as RNA Pol II) in order to increase the likelihood of capturing all nucleic acids associated with the protein of interest.

Isolation of chromatin may be achieved by various techniques described in the art. For example, the immunoprecipitating binding agent, in particular the antibody or chemical substance, can be immobilized on surfaces via affinity interactions. The surface can be, for example, particles (beads), chips, wells, flow cells, columns, etc. The beads can be magnetic, latex or agarose based material and the like. Where the immunoprecipitating binding agent is an antibody (or fragments thereof), the Fc-part of the antibody can bind to the surface of the beads via Protein A, Protein G, Protein L or the like. In this regard, Protein A is a 42 kDa surface protein originally found in the cell wall of the bacterium *Staphylococcus aureus*. It is encoded by the spa gene and its regulation is controlled by DNA topology, cellular osmolarity, and a two-component system called ArlS-ArlR. It is commonly used in biochemical research because of its ability to bind immunoglobulins. Alternatively, antibodies may bind to surfaces via Protein G, which is an immunoglobulin-binding protein expressed in group C and G Streptococcal bacteria much like Protein A but with differing binding specificities. It is a 65-kDa (G148 protein G) and a 58 kDa (C40 protein G) cell surface protein commonly used for purifying antibodies through its binding to the Fab and Fc region. Accordingly, the immunoprecipitating binding agent, wherein the agent is an antibody (or fragments thereof), can be bound to beads via Protein A, Protein G, Protein L or the like to isolate chromatin bound by said binding agent from unbound chromatin. This can be achieved by spin centrifugation using filter columns that retain the beads with the binding agent bound to chromatin on the filter while the non-bound chromatin fraction passes through the filter and can be discarded. In some embodiments, unbound chromatin can also be discarded by removing supernatant after spin centrifugation with regular tubes. In case of magnetic beads (usually based on polymethacrylate type polymers), magnetic force is applied to the beads to retain in a reaction vessel while the unbound chromatin fraction can be discarded by pipetting for example. The immunoprecipitating binding agent can also be pre-coupled to surfaces/beads before addition to chromatin. The immunoprecipitating binding agent can also be chemically cross-linked to surfaces when pre-coupled, and does not rely exclusively on affinity interactions to isolate chromatin. As an example Dimethyl pimelimidate (DMP) can be used to couple proteins to beads. Isolation of chromatin is often supported by wash steps to remove unspecific interactions of chromatin with the said binding agent or unspecific interactions of chromatin with the reaction vessel or surface of the isolating reagent. Washing of chromatin isolated by said immunoprecipitating binding agent or chemical substance isolated by above mentioned procedures is achieved by addition and subsequent removal of buffered aqueous solutions containing chemicals including salt and detergents. Accordingly, the methods of the invention may further comprise washing steps subsequent to isolation of chromatin bound by the immunoprecipitating binding agent.

Exonuclease

In some embodiments, the target chromatin isolated after immunoprecipitation or tagmentation described above is further treated by an enzyme with exonuclease activity. In some embodiments, the isolated chromatin is further treated to remove nucleotide(s) from 3'-hydroxyl termini of the double-stranded nucleic acid fragments associated with the protein of interest until the nicking is blocked by the protein of interest or associated protein thereof (see FIG. 2). This step is optional, but may increase the resolution of chromatin mapping, e.g. to the more precise boundary of where the protein of interest binds, such as transcription factor binding sites. Treating the isolated chromatin sample using an enzyme with exonuclease activity can also remove excess transposon end compositions that are not tagged onto target chromatin, thus decreasing the likelihood that these excess transposon end compositions will be over-amplified during later PCR steps. In some embodiments, the exonuclease has 3' to 5' exonuclease activity. In some embodiments, the exonuclease is only a 3' to 5' exonuclease. In some embodiments, the enzyme is a proofreading polymerase that supplies both the 3' to 5' exonuclease activity and the polymerase activity. In some embodiments, the 3' to 5' exonuclease activity is provided by a mutant error-correcting polymerase that does not have polymerase activity or has significantly reduced polymerase activity compared to a parent polymerase. In some embodiments, the mutant error-correcting polymerase (that lacks substantial polymerase activity) may have an increase in the ratio of double-stranded exonuclease activity to single-stranded exonuclease activity relative to the parent error-correcting polymerase. In some embodiments, the enzyme with 3' to 5' exonuclease activity is thermostable. In some embodiments, the enzyme with 3' to 5' exonuclease activity is not thermostable. In some embodiment, the 3' exonuclease is selected from the group consisting of exonuclease I, exonuclease III (Exo III), exonuclease VIII, and ribonuclease II. In some embodiments the exonuclease is Exo III. Exonucleases are well known to the ordinarily skilled artisan and are commercially available. In some embodiments, the 3' to 5' exonuclease digestion step is carried out in solution. In some embodiments, the 3' to 5' exonuclease digestion step is carried out when the target chromatin is still captured on the solid support (e.g., beads) through the immunoprecipitating binding agent (e.g., antibody).

Exonucleases are enzymes that catalyze the hydrolysis of the phosphodiester backbone of nucleic acids from the end of the polymer. Many exonucleases hydrolyze nucleotides either from only 3' or from only 5' ends. Involved in recombination, repair, replication, and the editing and processing of DNA and RNA, this class of enzymes encompasses a large number of different specificities and functions (Linn and Roberts, 1982, Linn et al, 1993). Single-stranded (ss) exonucleases hydrolyze nucleic acids that consist of a single nucleic acid polymer chain, e.g., *E. coli* Exonuclease I (Exo I). Double-stranded (ds) exonucleases hydrolyze nucleic acids that consist of two based-paired nucleic acid polymer strands, e.g., *E. coli* Exonuclease III (Exo III) is a non-processive 3' to 5' ds exonuclease. Many DNA polymerases, for example bacteriophage Phi 29 DNA polymerase, have an intrinsic 3' to 5' exonuclease activity that acts on the 3' end of double stranded DNA. This activity provides the "proofreading" ability of many DNA polymerases, removing mistakenly incorporated nucleotides and thereby increasing fidelity. It can also be employed to degrade DNA in a 3'-5' direction on a single strand of DNA that is either single- or double-stranded. Exemplary polymerases that can be used in the methods of the invention include a family A polymerase, e.g., in some embodiments, a family A polymerase that is deficient in 5' to 3' exonuclease activity, or that does not have 5' to 3' exonuclease activity; or a family B polymerase, such as *Pyrococcus furiosus* (Pfu); or a hybrid protein, e.g., a polymerase hybrid in which one of the parent polymerases is a family B polymerase such as Pfu polymerase.

Exonuclease III catalyzes the stepwise removal of mononucleotides from 3'-hydroxyl termini of duplex DNA. The preferred substrates are blunt or recessed 3'-termini, although the enzyme also acts at nicks and duplex DNA to produce single-strand gaps. The enzyme is not active on single-stranded DNA, and thus 3'-protruding termini are resistant to cleavage. The degree of resistance depends on the length of the extension, with extensions 4 bases or longer being essentially resistant to cleavage.

Denaturing

In some embodiments, the methods described herein comprise a denaturing step after target chromatin has been isolated after immunoprecipitation or target chromatin has been tagmented as described above. In some embodiments, the denaturing step is performed after digestion by exonuclease (e.g. Exo III) described above. In some embodiments, after denaturation, double-stranded nucleic acid fragments from the isolated target chromatin described above are turned into single-strand nucleic acid fragments. In some embodiments, the denaturation is carried out by heating, e.g. at 95° C. In some embodiments, the denaturation is carried out by heating at 95° C. for about 60 min. In some embodiments, the denaturation is carried out in the presence of detergent. In some embodiments, any protein present in the reaction, e.g., protein of interest (as well as any chromatin associated protein), the immunoprecipitating binding agent (e.g., antibody or fragments thereof), additional enzymes (e.g., Exo III), is denatured along with the denaturing of nucleic acids. In some embodiments, chromatin associated protein dissociates from the nucleic acid fragments after denaturation. In some embodiments, denaturation is carried out after reverse-crosslinking. In some embodiments, denaturation is carried out together with reverse-crosslinking.

Reverse-Crosslinking

In some embodiments, after target chromatin has been isolated after immunoprecipitation or target chromatin has been tagmented as described above, the protein of interest (as well as any chromatin associated protein) is removed from the target nucleic acid fragments, e.g., by reverse-crosslinking, and/or denaturing the protein. In some embodiments, formaldehyde crosslinks may be removed by heating the sample. In some embodiments, the sample is heated to about 65° C., preferably for several hours. In some embodiments, the sample may be heated to about 65° C. for 4 hours or more, for example overnight. In some embodiments, the sample may be heated to about 95° C. for about 10-15 minutes. In some embodiments, heating to lower temperatures, such as to about 65° C. is preferred to retain integrity of the sample comprising nucleic acid. In addition to heating, detergents and/or salt (for example 0.5-1% SDS and/or about 300 mM NaCl) may be added to remove crosslinks.

Moreover, RNase and/or Proteinase K may be added subsequent to reverse-crosslinking to remove RNA and/or protein, respectively, from the sample comprising nucleic acid, in particular DNA. As an example, samples can be treated for 30 min at 37° C. with about 0.5 µl 10 mg/ml RNase A DNase-free RNase, and subsequently with about 1 µl 20 mg/ml proteinase K for about 1-2 hour at 55° C.

In some embodiments of the methods of the present invention, the sample may be heated to high temperatures to reverse cross-linking. In some embodiments, the sample may be heated to about 95° C. to reverse cross-links. Such high temperatures significantly reduce the time required to reverse cross-links. Such high temperatures usually cannot be used in standard ChIP protocols, because heating to high temperatures (e.g. 95° C.) would denature ChIP DNA (or input DNA), and due to the complexity of the ChIP DNA (or input DNA), some fragments (especially AT-rich sequences) do not re-anneal properly. When preparing a library by ligation of double-stranded adapters, ChIP DNA (or input DNA) fragments that do not re-anneal properly are likely excluded from the final library and will introduce a sequencing bias. However, in the methods of the present invention, high temperatures, e.g. about 95° C., can be employed in order to reverse cross-links and denature the double-stranded DNA (ChIP or input DNA) at the same time, and the tagged ssDNA can be used for later self-circularization. This remarkably reduces the overall duration of the assay. In addition, using high temperatures to reverse cross-links, like about 95° C., avoids the step of elution from beads (used during immunoprecipitation), which further reduces the complexity and overall time required for practicing the methods of the invention, as well as reduces materials lost during each step. Elution from beads normally comprises the use of buffers (e.g., SDS and/or high concentrations of salt) incompatible with subsequent library preparation steps, e.g. PCR. Thus a DNA cleanup step is normally required. However, the method described herein makes DNA purification unnecessary after reverse-crosslinking/denaturing/bead elution. In some embodiments, the reverse-crosslinking and/or denaturing is carried out at about 95° C. for about 60 min.

Self-Circularization

In some embodiments, the methods of the present invention further comprises self-circularizing the single-strand nucleic acid fragments (e.g., 5' tagged ssDNA fragments) after denaturation and/or reverse cross-linking described above. In some embodiments, the self-circularization is carried out by a single-strand DNA (ssDNA) ligase, such as CircLigase™ enzyme or *Methanobacterium* thermoautotrophicum RNA ligase 1 (MthRn1). In some embodiments, the self-circularization is carried out by a template-independent ligase, e.g., CIRCLIGASE™ ssDNA ligase, or bacteriophage TS2126 RNA ligase. In some embodiments, the self-circularization is carried out by a template-dependent ligase.

Examples of homologous or template-dependent DNA ligases include NAD-type DNA ligases such as *E. coli* DNA ligase, Tth DNA ligase, Tfl DNA ligase, and AMPLIGASE® DNA ligase (EPICENTRE Biotechnologies, Madison, Wis., USA), which catalyze intramolecular ligation of ssDNA molecules only in the presence of a ligation template, and ATP-type DNA ligases, such as T4 DNA ligase or FASTLINKT™ DNA ligase (EPICENTRE Biotechnologies), which, while they do not require a ligation template for blunt-end ligation, they catalyze template-dependent ligation much more efficiently.

In some embodiments, the template-dependent ligase is from a psychrophilic bacterium or a psychrophilic bacteriophage so that the ligation can be performed at lower temperatures (e.g., when the sequences of the oligonucleotides or polynucleotides that form the ligation junction exhibit lower $T_m$'s). A DNA ligase is chosen for use in the method that is active at a temperature at which the DNA molecules used for joining (e.g., the 5'-tagged DNA fragment extension products or the 5'-tagged DNA fragments and the random-sequence oligonucleotides) anneal for sufficient time to be ligated by the ligase.

The single-stranded nucleic acid circles may be amplified under isothermal conditions by employing rolling circle amplification (RCA) methods. The amplification of single-stranded nucleic acid circles may be performed in the same reaction vessel in which the intra-molecular ligation is performed. Isolation or purification of single-stranded nucleic acid circles and/or removal of the ligase may not be necessary prior to the amplification reaction. In some embodiments, the entire process of single-stranded nucleic acid ligation and amplification may be performed in a single tube without any intermediate purification or isolation steps.

In some embodiments, the tagged circular ssDNA fragments are used as next-generation sequencing templates, or, following labeling, as target for annealing to probes on an array or microarray, or for other applications described elsewhere herein.

Linearization

In some other embodiments, the method of the present invention further comprises the step of linearizing the tagged circular ssDNA fragments described above, thereby generating di-tagged linear ssDNA fragments. In some embodiments comprising linearizing the tagged circular ssDNA fragments, the transposon end composition tag comprises multiple tag domains, wherein the step of linearizing the transposon end composition tag results in one portion of the transposon end composition tag on the 5' end and another portion of the transposon end composition tag on the 3'-end. For example, in some embodiments, the transferred strand of the transposon end composition exhibits the transposon end composition tag that comprises multiple tag domains (e.g., amplification tag and amplification facilitating tag), of which, at least one tag domain is joined to the 3' end of the di-tagged ssDNA fragments generated from the step of linearizing the tagged circular ssDNA fragments. For example, in some embodiments, the 5'-tagged DNA fragments are generated using a transposon end composition comprising a transferred strand that contains one or more nucleotides that permit cleavage at the sites of said nucleotides (i.e. restriction site tag), and the step of linearizing the tagged circular ssDNA fragments within the tag comprises cleaving the tagged circular ssDNA fragments at said restriction site tag. For example, in some embodiments, the transferred strand contains one or more deoxyuridine nucleotides or one or more 8-oxoguanine nucleotides (e.g., synthesized using an oligonucleotide synthesizer), and the step of linearizing the tagged circular ssDNA fragments within the tag comprises cleaving the tagged circular ssDNA fragments by incubating the tagged circular ssDNA fragments with uracil-DNA glycosylase (or USER enzyme) or formamidopyrimidine-DNA glycosylase, respectively, and an endonuclease that cleaves DNA at an abasic site (e.g., endonuclease IV). In some embodiments, linearizing the circularized ssDNA fragments by generating a breakage at the restriction site tag is carried out by USER™ enzyme, or a mixture of Uracil DNA glycosylase (UDG) and the DNA glycosylase-lyase Endonuclease VIII. For example, in some other embodiments, the tagged circular ssDNA fragments are linearized within the tag domain by annealing a complementary oligonucleotide to the tag and linearizing using a restriction endonuclease that recognizes a restriction site within the double-stranded tag. In some of any of the embodiments comprising linearizing the tagged circular ssDNA fragments, the method further comprises purifying the di-tagged ssDNA fragments (e.g., using a Qiagen PCR cleanup column); in some of these embodiments, the di-tagged ssDNA fragments are used as next-generation sequencing templates or, following labeling, as target for annealing to probes on an array or microarray, or for other applications described elsewhere herein.

In some embodiments, the method of the present invention further comprises the step of amplifying the library of tagged DNA fragments comprising the di-tagged linear ssDNA fragments described herein, thereby generating an amplified library of tagged DNA fragments. In some embodiments, the step of amplifying the library of tagged DNA fragments comprises performing a polymerase chain reaction (PCR), thereby generating an amplified library of tagged DNA fragments comprising amplified di-tagged DNA fragments. In some preferred embodiments, the PCR reaction is performed using a first PCR primer and a second PCR primer, each having a 3'-portion and a 5'-portion, wherein the 3'-portion of the first PCR primer is complementary to a sequence exhibited by one tag portion in the tagged DNA fragments and the 3'-portion of the second PCR primer is complementary to a sequence that is complementary to another tag portion, and wherein each 5' portion comprises a sequencing tag domain that comprises or consists of an appropriate sequencing tag that permits use of the amplified di-tagged DNA fragments generated as templates for next-generation sequencing using a particular next-generation sequencing platform (e.g., the Roche 454A and 454B sequencing tags, the ILLUMINA™ SOLEXA™ sequencing tags, the Applied Biosystems' SOLID™ sequencing tags, the Pacific Biosciences' SMRT™ sequencing tags, the Pollonator Polony sequencing tags, or the Complete Genomics sequencing tags). In some embodiments, the first PCR primer comprises a first sequencing tag and a first annealing tag, and the second PCR primer comprises a second sequencing tag, an experimental index tag and a second annealing tag. In some embodiments, the first and second sequencing tags can bind to complementary sequencing tags conjugated on a surface (e.g., a parallel sequencing flow cell surface). In some embodiments, the first annealing tag is at least about 80% (such as at least about any of 80%, 85%, 90%, 95%, 96%, 97%, 98%, 99%, or 100%) complementary to the amplification tag. In some embodiments, the second annealing tag is at least about 80% (such as at least about any of 80%, 85%, 90%, 95%, 96%, 97%, 98%, 99%, or 100%) complementary to a sequence that is complementary to the transferred transposon end sequence. In some embodiments, the first PCR primer comprises SEQ ID NO: 14. In some embodiments, the second PCR primer comprises a sequence selected from SEQ ID NOs: 15-20. Any of the available barcode sequences used during sequencing (e.g. barcodes from NEBNext® Multiplex Oligos for Illumina® Kit, Illumina® Multiplexing Sample Preparation Oligonucleotide Kit, or Nextera™ DNA Sample Prep Kits, KAPA DNA Library Preparation Kits, EpiNext DNA Library Preparation Kit, or PicoPLEX® DNA-seq Kit, etc.), or any combinations of A/T/G/C that can identify the samples/experiments while not affecting tagging/library preparation/sequencing, can be employed as experimental index tag. In some embodiments, the experimental index tag comprises a sequence selected from SEQ ID NOs: 24 and 33-37.

Real-Time PCR (qPCR)

In some embodiments of any of the methods of the invention for obtaining tagged DNA fragments to which protein of interest associated with, the method further comprises: quantify the tagged DNA fragments comprising di-tagged ssDNA fragments, or tagged circular ssDNA fragments using real-time PCR.

Real-time PCR refers to the detection of PCR products via a fluorescent signal generated by the coupling of a fluorogenic dye molecule and a quencher moiety to the same or different oligonucleotide substrates. Examples of commonly used probes are TAQMAN® probes, Molecular Beacon probes, SCORPION® probes, and SYBR® Green probes. Briefly, TAQMAN® probes, Molecular Beacons, and SCORPION® probes each have a fluorescent reporter dye (also called a "fluor") attached to the 5' end of the probes and a quencher moiety coupled to the 3' end of the probes. In the unhybridized state, the proximity of the fluor and the quencher molecules prevents the detection of fluorescent signal from the probe; during PCR, when the polymerase replicates a template on which a probe is bound, the 5'-nuclease activity of the polymerase cleaves the probe thus, increasing fluorescence with each replication cycle. SYBR Green® probes binds double-stranded DNA and upon excitation emit light; thus as PCR product accumulates, fluorescence increases. The methods of performing real-time PCR and analyzing results are well-known.

Real-Time PCR Amplification Primer

In some preferred embodiments, the real-time PCR reaction is performed using a first PCR primer and a second PCR primer, each having a 3'-portion and a 5'-portion, wherein the 3'-portion of the first PCR primer is complementary to a sequence exhibited by the tag in the tagged DNA fragments and the 3'-portion of the second PCR primer is complementary to a sequence that is complementary to the tag. In some embodiments, the first PCR primer comprises a first annealing tag, and the second PCR primer comprises a second annealing tag. In some embodiments, the first annealing tag is at least about 80% (such as at least about any of 80%, 85%, 90%, 95%, 96%, 97%, 98%, 99%, or 100%) complementary to the amplification tag. In some embodiments, the second annealing tag is at least about 80% (such as at least about any of 80%, 85%, 90%, 95%, 96%, 97%, 98%, 99%, or 100%) complementary to a sequence that is complementary to the transferred transposon end sequence. In some embodiments, the first PCR primer comprises SEQ ID NO: 14. In some embodiments, the second PCR primer comprises a sequence selected from SEQ ID NOs: 15-20. In some embodiments, the first and/or second PCR primers used in real-time PCR further comprise additional tags, e.g. sequencing tag.

Amplification, Generating Sequencing Library, and Other Embodiments

In some embodiments of any of the methods of the invention for generating the library of tagged DNA fragments, the method further comprises: amplifying the library of tagged DNA fragments comprising di-tagged ssDNA fragments, or tagged circular ssDNA fragments, as well as sequencing.

In some embodiments of any of the methods, the method further comprises step of: amplifying the library of di-tagged linear ssDNA, or the tagged circular DNA fragments using a polymerase chain reaction (PCR). Thus, in some embodiments, the method further comprises (a) providing (i) first and second PCR primers, wherein at least the 3'-end of the first PCR primer is complementary to at least a portion of the tag sequence of the tagged circular DNA fragments or to at least a portion of the tag sequence that is joined to the 3'-end of the linear ssDNA fragments (e.g., 3'-end of the first PCR primer is complementary to the amplification tag), and wherein at least the 3'-end of the second PCR primer is complementary to at least a portion of the complement of the tag sequence of the tagged circular DNA fragments (i.e., wherein at least the 3'-end of the second PCR primer exhibits a sequence that is identical to at least a portion of the tag sequence), or wherein at least the 3'-end of the second PCR primer is complementary to at least a portion of the complement of the tag sequence that is joined to the 5'-end of the di-tagged linear ssDNA fragments (i.e., wherein at least the 3'-end of the second PCR primer exhibits a sequence that is identical to at least a portion of the tag sequence that is joined to the 5'-end of the di-tagged linear ssDNA fragments, such as the transferred transposon end sequence), and (ii) a thermostable DNA polymerase that can be used for PCR; and (b) incubating the tagged circular DNA fragments or the di-tagged linear ssDNA fragments with the respective first and the second PCR primers and the thermostable DNA polymerase under PCR amplification conditions and for sufficient time wherein amplified di-tagged linear dsDNA fragments are generated.

In some embodiments, the 5' portion of the first PCR primer or the 5' portion of the second PCR primer, or the 5' portions of both the first and the second PCR primers comprise or consist of first or second sequencing tags, respectively, for generation of templates for next-generation sequencing for a particular sequencing platform (e.g., sequencing tags for: a ROCHE 454A or 454B sequencing platform; for an ILLUMINA SOLEXA/HiSeq/MiniSeq/MiSeq/NextSeq sequencing platform; for an APPLIED BIOSYSTEMS SOLID™ sequencing platform; for a PACIFIC BIOSCIENCES' SMRT™ sequencing platform; for a POLLONATOR POLONY sequencing platform; for a HELICOS sequencing platform; for a COMPLETE GENOMICS sequencing platform; for an INTELLIGENT BIOSYSTEMS sequencing platform; or for any other sequencing platform). In some embodiments, the 5' portion of the first PCR primer or the 5' portion of the second PCR primer additionally comprises or consists of an experimental index tag or another tag domain for a particular purpose. In other embodiments, the tag of the tagged circular DNA fragments comprises a sequencing tag for next-generation sequencing using a particular platform.

In some embodiments wherein a library of tagged DNA fragments comprising di-tagged DNA fragments is not generated using a DNA polymerase that has 5' nuclease or strand-displacement activity, the step of amplifying the library comprises performing a polymerase chain reaction (PCR), the method further comprising: (1) providing (a) first and second PCR primers, wherein at least the 3'-end of the first PCR primer is complementary to at least a portion of the transposon end composition tag at the 3' end of the di-tagged DNA fragments or to at least a portion of the tag in the tagged circular ssDNA fragments and at least the 3'-end of the second PCR primer is complementary to at least a portion of the complement of the portion of the transposon end composition tag at the 5' end of the di-tagged DNA fragments or the fantail DNA fragments or to at least a portion of the complement of the tag in the tagged circular ssDNA fragments, and (b) a thermostable DNA polymerase that is suitable for PCR; and (2) incubating the library of tagged DNA fragments with the PCR primers and the thermostable DNA polymerase under PCR amplification conditions and for sufficient time wherein the library of tagged DNA fragments is amplified to generate a library of amplified tagged DNA fragments. In some embodiments, the first or the second PCR primer comprises a 5' portion and a 3' portion, wherein the 5' portion is not complementary to the sequence in the respective tag or its complement in the tagged DNA fragments and the 3' portion is complementary to the sequence of the respective tag or its complement. In some embodiments, the 5' portion of the first and second PCR primers comprise or consist of the appropriate first and second sequencing tags that permit their use to generate templates for next-generation sequencing (e.g., the Roche 454A and 454B sequencing tags or the appropriate first and second sequencing tags for another sequencing platform; e.g., without limitation, the Illumina Solexa or the Applied Biosystems Solid platform).

A wide variety of enzymes and kits are available for performing the amplification reaction by PCR. For example, in some embodiments, the PCR amplification is performed using either the FAILSAFE™ PCR System or the MASTERAMP™ Extra-Long PCR System from EPICENTRE Biotechnologies, Madison, Wis., as described by the manufacturer. These systems permit rapid optimization of the PCR reaction conditions using a series of 2×PCR PreMixes provided with each system to identify the optimal PreMix for a particular template and primer pair. However, the invention is not limited to the use of those products or conditions for the amplification reaction and any suitable thermostable DNA polymerase and reaction mixture that permits amplification of the sequence between the primer that anneals to the target sequence and the primer that anneals to the transposon can be used. In some embodiments, NEBNext® Q5® Hot Start HiFi PCR Master Mix is used.

The invention is also not limited to the use of PCR to amplify the library of tagged DNA fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present invention. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523, 204; 5,536,649; 5,624,825; 5,631,147; 5,648,211; 5,733, 752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214, 587 of Gen-Probe, Inc.; U.S. Pat. No. 6,063,604 of Wick et al.; U.S. Pat. No. 6,251,639 of Kurn; U.S. Pat. No. 6,410, 278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi.

In some embodiments of the invention, it is not necessary to size select the library of 5'-tagged DNA fragments generated in the transposition reaction or the final library of tagged DNA fragments. In the event size selection or purification is necessary for certain applications, the 5'-tagged DNA fragments or the final library of tagged DNA fragments can be size selected by agarose gel electrophoresis (e.g., using a low-melting-temperature non-denaturing agarose gel of an appropriate percentage agarose for the desired size range of DNA fragments), and purified (e.g., to remove the un-inserted transposon end oligonucleotides, other reaction products, and agarose gel; e.g., by digestion of the portion of the agarose gel containing the desired size range of 5'-tagged DNA fragments or the final library of tagged DNA fragments with GELase™ agarose gel-digesting enzyme, EPICENTRE Biotechnologies, Madison, Wis., USA, followed by alcohol precipitation, and other clean-up steps according to directions with the GELase product, or using any other purification method known in the art). In some embodiments, a purification step comprising polyethylene glycol (PEG) precipitation is used to precipitate the library of tagged DNA fragments without precipitating contaminating substances (e.g., without limitation, unligated ligation tagging oligonucleotides or other reaction components). In some embodiments, a spin column or any other purification method known in the art is used. In some embodiments, the library of 5'-tagged DNA fragments or the final library of tagged DNA fragments are size-selected using Agencourt AMPure XP beads and manufacture protocols.

In some embodiments, the tagged circular DNA fragments are used as templates for DNA sequencing.

In some embodiments, the tagged DNA fragments (e.g., di-tagged ssDNA fragments) are used as templates for DNA sequencing.

In some embodiments, the library of tagged DNA fragments is used as template for an amplification reaction (e.g., a PCR amplification reaction using PCR primers that are complementary to the 5' and the 3' tags of tagged DNA fragments comprising di-tagged DNA fragments or that are complementary to the tag of tagged DNA fragments comprising tagged circular ssDNA fragments). In some preferred embodiments, the library of amplified tagged DNA fragments comprises most or approximately all of the sequences exhibited by the target DNA. In some embodiments wherein the target DNA comprises genomic DNA of an organism, the amplification reaction is a whole genome amplification reaction.

In some embodiments of the method comprising amplifying the tagged DNA fragments, the amplified tagged DNA fragments are labeled by incorporation of a labeled nucleotide during one or more steps of the amplification method (e.g., the PCR amplification reaction method). In some embodiments, the library of amplified tagged DNA fragments that contain the label is used to detect or capture or to detect and capture the amplified tagged DNA fragments that contain the label for a particular application.

Some embodiments of any of the methods of the invention for generating a library of tagged DNA fragments (e.g. di-tagged DNA fragments) comprise generating a library of "labeled" tagged DNA fragments that contain one or multiple moieties (e.g., one or multiple affinity-binding molecules) that permit capture of the labeled tagged DNA fragments on a surface, or one or multiple detectable moieties that permit detection of the labeled tagged DNA fragments (e.g., which anneal to a complementary DNA, such as complementary DNA in a chromosome). Also, some embodiments of any of the methods of the invention comprising further amplifying the library of tagged DNA fragments comprise generating a library of "labeled" amplified tagged DNA fragments comprising one or multiple moieties (e.g., one or multiple affinity-binding molecules) that permit capture on a surface, or one or multiple detectable moieties that permit detection of the labeled tagged DNA fragments (e.g., which anneal to a complementary DNA, such as complementary DNA in a chromosome). In some embodiments, the library of labeled tagged DNA fragments or labeled amplified tagged DNA fragments is generated by using at least one labeled oligonucleotide (e.g., a labeled transferred transposon end oligonucleotide, a labeled ligation tagging oligonucleotide, or at least one labeled amplification primer, such as at least one (or more than one) PCR primer). In some other embodiments, a library of labeled amplified tagged DNA fragments is generated by including a labeled dNTP that is incorporated into the amplification products during the amplification reaction. The labeled dNTP can have any label known in the art that can be used for generating labeled amplified tagged DNA fragments, whether by direct labeling or by indirect labeling. By "direct labeling", we mean that the capture moiety or detectable label is attached directly to the amplified tagged DNA fragments without any other moiety between the capture or detectable moiety and the tagged DNA fragment or amplified tagged DNA fragment. By "indirect labeling", we mean that there is at least one other moiety between the capture or detectable moiety and the tagged DNA fragment or amplified tagged DNA fragment. One example of direct labeling is incorporating a dye-labeled nucleotide into the tagged DNA fragments, whereas one example of indirect labeling is incorporating a biotin-labeled nucleotide into the tagged DNA fragments and then labeling the tagged DNA fragments with a dye detectable moiety by incubating with dye-labeled streptavidin under conditions wherein the dye-labeled streptavidin binds to the biotin-labeled nucleotides. The invention comprises use of any suitable method for generating the library of labeled tagged DNA fragments or labeled amplified tagged DNA fragments, wherein the label is subsequently used for capture or detection.

In some other embodiments, tagged DNA fragments in a library prepared using a method of the invention are subsequently labeled, directly or indirectly, by contacting the library of tagged DNA fragments with a reactive dye molecule (e.g., any of the reactive fluorescent dyes containing an N-hydroxysuccinimidyl or "NHS" ester from Molecular Probes, Eugene, Oreg.) or with a reactive affinity-binding molecule (e.g., a reactive biotinylation reagent, such as a biotin-NHS compound, from Pierce Chemical Company, Rockford, Ill.). For example, in some embodiments, the library of labeled amplified tagged DNA fragments is generated by incorporating a dNTP that contains an aminoallyl-group during the amplification reaction, and then the library of amplified tagged DNA fragments containing the aminoallyl-group is contacted with the labeled fluorescent dye-NETS ester or the biotin-NHS ester to generate a fluorescent dye-labeled amplified tagged DNA fragments or biotin-labeled amplified tagged DNA fragments, respectively. Those with knowledge in the art will know or know how to find many additional specific methods and reagents, including kits, e.g., from Molecular Probes, for labeling the library of amplified tagged DNA fragments for a particular purpose (e.g. to permit capture on a surface or detection). For example, Examples include one or more modified nucleotides that has an aminoallyl-group, a propynyl-group, a biotin group, a fluorescent or other detectable dye, or any other detectable molecule or combination of molecules known in the art, including quantum dots, an enzyme (e.g., a phosphatase, a peroxidase, or a pyrophosphatase), or a detectable protein (e.g., phycobiliprotien, phycoerythrin). In some other embodiments, a library of labeled amplified tagged DNA fragments is generated by incorporation of one or more modified dNTPs that are labeled with an affinity-binding molecule or a detectable moiety during the amplification reaction, e.g., during a PCR amplification reaction, e.g., by incorporation of one or more modified dNTPs that has an aminoallyl-group, a biotin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody).

In some embodiments, the tagged DNA fragments (e.g., 5'- or di-tagged DNA fragments are used for preparation of labeled DNA fragments for hybridization to probes attached to a surface (e.g., as labeled target DNA for hybridization to DNA probes on an array or microarray). In some embodiments, tagged DNA fragments (e.g., comprising 5'- or di-tagged DNA fragments) are used for hybridization to chromosomes or parts of chromosomes in fixed cells or tissue sections (e.g., for fluorescent in situ hybridization or FISH).

In some embodiments, the method comprises generating labeled tagged DNA fragments or labeled amplified tagged DNA fragments (e.g., labeled 5'- or di-tagged DNA fragments or labeled amplified di-tagged DNA fragments) for use in hybridization to chromosomes (e.g., wherein the labeled tagged DNA fragments are prepared from target DNA comprising DNA from one or more specific chromosomes for use as "chromosome paints" (e.g., for hybridization to one or more chromosomes in fixed cells or tissue sections, e.g., using fluorescent in situ hybridization or FISH for applications such as typing chromosomes, or for research, medical diagnostics, identifying the sex of an organism, or other cell biological applications). In some embodiments, the method comprises generating labeled tagged DNA fragments or labeled amplified tagged DNA fragments from target DNA comprising parts of chromosomes (e.g., wherein the tagged DNA fragments are prepared from DNA encoding one or more specific genes or loci of one or more chromosomes (e.g., for hybridization to one or more chromosomes in fixed cells or tissue sections, e.g., using fluorescent in situ hybridization or FISH, or for use as gene-specific or loci-specific probes in in vitro assays for applications such as analyte-specific assays or diagnostic tests for medical, industrial, environmental, or molecular or cell biology research applications).

In some embodiments, hybridization of labeled tagged DNA fragments to probes on a surface (e.g., an array or microarray, a dipstick, a quantum dot, a bead, or a microchannel in a microfluidic device) is used for detecting, quantifying, determining relative quantities, or characterizing one or more DNA molecules or portions thereof that is in or from a natural source (e.g. genomic DNA from a cell; e.g., human DNA for evaluation of copy-number variation or "CNV", or DNA from a pathogenic bacterial, fungal, mycoplasmal, viral, or nematode cell that is a pathogen), or from an in vitro source (e.g., double-stranded cDNA made by reverse transcription of RNA, such as mRNA or non-coding RNA or viral RNA, that is isolated from a natural source or that is amplified from a natural source using a nucleic acid amplification method, such as a DNA or RNA amplification method).

In some other embodiments wherein the method comprises amplifying the tagged DNA fragments, the method comprises generating labeled amplified tagged DNA fragments by incorporating one or more modified dNTPs that has an affinity-binding molecule or a detectable moiety during the amplification reaction, e.g., during a PCR amplification reaction (e.g., by incorporation of one or more modified dNTPs that has an aminoallyl-group, a biotin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody).

In some other embodiments, the tagged DNA fragments or amplified tagged DNA fragments prepared using a method of the invention are labeled by incorporation of one or more modified dNTPs that has an affinity-binding molecule or a detectable moiety during the amplification reaction (e.g., during the respective transcription, RCR or PCR reaction, e.g., by incorporation of one or more modified dNTPs that has an aminoallyl-group, a biotin group, a digoxigenin group, a fluorescent or other detectable dye, or another moiety that permits it to be detected, either directly, or indirectly following labeling with any other detectable molecule or combination of molecules known in the art, including quantum dots, or an enzyme or detectable protein (e.g., phycobiliprotein, phycoerythrin) that is linked to an affinity binding molecule (e.g., as streptavidin, an antibody). In some embodiments, the respective products are used for preparation of labeled nucleic acid fragments for hybridization to probes attached to a surface (e.g., as labeled target nucleic acid for hybridization to DNA probes on an array or microarray). In some embodiments, the respective labeled products are used for hybridization to chromosomes or parts of chromosomes in fixed cells or tissue sections (e.g., for fluorescent in situ hybridization or FISH). In some embodiments, hybridization of labeled products to probes on a surface is used for detecting, quantifying, determining relative quantities, or characterizing one or more portions of a target DNA from a natural source (e.g. genomic DNA from a cell; e.g., for evaluation of copy-number variation or "CNV") or from an in vitro source (e.g., double-stranded cDNA made by reverse transcription of RNA, such as mRNA or non-coding RNA (ncRNA), that is isolated from a natural source or that is amplified from a natural source using an RNA amplification method).

In some embodiments of methods comprising generating a library of tagged circular DNA fragments, the transferred transposon end oligonucleotide, in addition to exhibiting the sequence of the transferred transposon end in its 3' portion, also exhibits a sequence of one strand of a double-stranded RNA polymerase promoter in its 5' portion. In some embodiments of methods comprising generating a library of di-tagged DNA fragments using a ligation tagging oligonucleotide and a template-dependent ligase, the ligation tagging oligonucleotide exhibits a sequence of one strand of a double-stranded RNA polymerase promoter in its 3' portion. In some embodiments of methods wherein the transferred transposon end oligonucleotide or the ligation tagging oligonucleotide does not exhibit an RNA polymerase promoter sequence, the method further comprises PCR amplifying the di-tagged DNA fragments using at least one PCR primer that is a "promoter primer." The promoter primer has a "5'-flap" or "5'-tail" portion that does not anneal to the di-tagged DNA fragments and that exhibits the sequence of one strand of a double-stranded RNA polymerase promoter, and a 3' portion that anneals to the 5' or 3' tag of the 5'- and 3'-tagged DNA fragments or their complements.

In some preferred embodiments wherein the transferred transposon end oligonucleotide, the ligation tagging oligonucleotide, or a PCR primer exhibits an RNA polymerase promoter sequence, the RNA polymerase promoter is a T7-type RNA polymerase promoter and the method further comprises the step of transcribing the 5'- and 3'-tagged DNA fragments in vitro using a T7-type RNA polymerase that recognizes the promoter. Most preferably, the RNA polymerase and promoter are chosen from among T7 RNAP, T3 RNAP and SP6 RNAP and the corresponding cognate promoters. However, transcription steps of a method of the invention can use any RNAP for which a suitable promoter sequence that permits transcription with high specificity is known or can be obtained. Kits and enzymes for in vitro transcription are commercially available from many vendors and the appropriate reaction mixtures and conditions for carrying out steps of the present invention comprising in vitro transcription can use those products as described by the manufacturers. For example, in vitro transcription using T7 RNAP can be carried out using the AMPLISCRIBE™ T7-Flash™ Transcription Kit or the AMPLISCRIBE™ T7 High Yield Transcription Kit from EPICENTRE Biotechnologies, Madison, Wis. as described in the product literature. Similarly, if T3 RNAP or SP6 RNAP is used in a method of the invention for in vitro transcription, an AMPLISCRIBE™ T3-Flash™ High Yield Transcription Kit or with the AMPLISCRIBE™ SP6 High Yield Transcription Kit (EPICENTRE Biotechnologies, Madison, Wis.), respectively, can be used as described.

In some embodiments, the transferred transposon end oligonucleotide, the ligation tagging oligonucleotide, or a PCR primer exhibits, in addition to the RNA polymerase promoter sequence, additional sequences for translation, such as but not limited to a ribosome binding site and a translation start codon (also referred to as a "translation start signal"), and the method additionally comprises translating the transcribed RNA. In some of these embodiments, the method further comprises the step in vitro translation of the resulting RNA transcripts. Systems and kits for in vitro translation of the RNA transcripts are also commercially available from many sources and can be used for the present invention. By way of example but not of limitation, rabbit reticulocyte lysate, wheat germ extract, and E. coli S30 extract systems from PROMEGA Corporation, Madison, Wis. can be used for the present invention. Still further, kits for coupled in vitro transcription and in vitro translation are also commercially available and can be used, such as TNT® Quick Coupled Transcription/Translation Systems from Promega.

In some preferred embodiments of the method, the library of di-tagged DNA fragments generated from target DNA comprising DNA sample from a whole genome of a cell or organism are PCR amplified (i.e., the method comprises or consists of a method for whole genome amplification). In some embodiments, the method for whole genome amplification is used to amplify a whole genome from a single cell. In some embodiments of the whole genome amplification method herein, the library of tagged DNA fragments is generated from a DNA sample from a whole genome of a cell or organism are PCR amplified using the single oligonucleotide primer (or PCR primer) that is complementary to the 3' tag.

In some embodiments, the tagged DNA fragments generated using a method of the invention are generated from target DNA comprising or consisting of genomes and/or double-stranded cDNA prepared from RNA from all organisms (e.g., multiple organisms) that are present in an environmental sample (e.g., for metagenomic or metatranscriptomic applications, including for industrial, medical, or research applications).

In some other embodiments of the method, the library of tagged DNA fragments is generated from target DNA comprising DNA comprising or consisting of a single chromosome or a portion of a chromosome. In some of these embodiments, the method comprises PCR amplifying library of tagged DNA fragments generated from the target DNA comprising or consisting of DNA of a single chromosome or a portion of a chromosome, including a portion of a chromosome comprising one or more genes or gene loci under conditions wherein the PCR-amplified products are labeled with a detectable moiety (e.g., a fluorescent, infrared-fluorescent, chemiluminescent, visible, or other detectable dye; e.g., using a dye-labeled dNTP in the PCR. In some embodiments, the PCR-amplified products that are labeled with the detectable moiety are used for staining fixed cells in situ (e.g., the PCR amplification products are used as chromosome paints). Thus, in some preferred embodiments, the method comprises or consists of a method for making chromosome paints or sub-chromosome paints or chromosome markers.

In some embodiments, the tagged DNA fragments or the amplified tagged DNA fragments generated using the method are used as the target DNA for a second round of fragmentation and tagging using a method of the invention. In some embodiments, the same transposome is used in both the first and second rounds of the method. In some embodiments, a second different transposase and different transposon ends are used for the second round.

In some embodiments, the tagged DNA fragments or the amplified tagged DNA fragments generated using the method are cloned in a vector (e.g., in a COPYCONTROL™ fosmid vector, EPICENTRE Biotechnologies, Madison, Wis., USA). In some embodiments wherein the method further comprises cloning the tagged DNA fragments or the amplified tagged DNA fragments and wherein the tagged DNA fragments or the amplified tagged DNA fragments (e.g., PCR-amplified tagged DNA fragments exhibits an RNA polymerase promoter, the method further comprises transcribing at least one strand of the cloned tagged DNA fragments or the amplified tagged DNA fragments. In some embodiments, the cloned tagged DNA fragments or the amplified tagged DNA fragments are transcribed in vitro using an RNA polymerase that recognizes the RNA polymerase promoter. In some embodiments, the cloned tagged DNA fragments or the amplified tagged DNA fragments are transcribed in vivo in a host cell that is capable of inducible expression of the RNA polymerase that recognizes the RNA polymerase promoter and then transcribing DNA templates that contain the promoter to which the RNA polymerase binds (e.g., the pET system is widely used for expression of proteins in vivo from an induced T7-type RNA polymerase). In some preferred embodiments, the RNA polymerase for in vitro or in vivo expression is a T7-type RNA polymerase and transcription is initiated from a respective cognate T7-type RNAP promoter. In some preferred embodiments, the T7-type RNA polymerase is selected from among T7 RNA polymerase, T3 RNA polymerase, and SP6 RNA polymerase.

In some embodiments of any of the methods, either the transferred transposon end oligonucleotide, the ligation tagging oligonucleotide, or a PCR primer, contains or is joined to an affinity molecule (e.g., biotin or digoxigenin), and the method additionally comprises the steps of: providing a solid surface that is covalently or non-covalently coated with an affinity binding substance that is capable of specifically binding and forming a specific binding pair with the affinity molecule (e.g., streptavidin or avidin for binding biotin, or an antibody for binding digoxigenin); and, either prior to or following the step in which it is involved, contacting the products generated using the transferred transposon end oligonucleotide, the ligation tagging oligonucleotide, or the PCR primer that is chemically joined to the affinity molecule under conditions and for sufficient time wherein it binds to affinity binding substance that is joined to the solid surface.

The invention is not limited to a particular solid surface, which can be porous or non-porous, and of any composition, size or shape that is suitable for the particular method and application. By way of example, but not of limitation, the solid surface can be selected from the group consisting of: magnetic beads, coated beads, slides, the wells of a microtiter plate, tubes, and dipsticks consisting of glass, plastic (e.g., latex or polystyrene), silica, Teflon, or another suitable material. The purpose of the solid surface that is coated with the affinity binding substance is to permit manipulation (e.g., capture and washing to remove from other molecules in a reaction mixture), isolation, and capture of the transferred transposon end oligonucleotide, the ligation tagging oligonucleotide, or the PCR primer that is chemically joined to the affinity molecule, or to permit manipulation, isolation, and capture of the 5'-tagged DNA fragments, the 5'- and 3'-tagged DNA fragments, or the PCR products generated therefrom. In order to prevent non-specific binding, in some embodiments, the solid support is treated with a large excess of a substance selected from the group consisting of: DNA-free tRNA; protein (e.g. BSA), polysaccharide (e.g., glycogen, dextran sulphate, or heparin). The invention is also not limited to a specific affinity molecule or affinity binding substance, so long as they are capable of specifically binding and forming a specific binding pair.

Thus, in some embodiments, the tagged DNA fragments or the amplified tagged DNA fragments are captured, isolated, purified, or used in another method by binding to the solid surface, the method comprising the steps of: contacting the tagged DNA fragments or the amplified tagged DNA fragments that contains the affinity molecule with the solid surface in the presence of reagents and under conditions that facilitate its binding to the affinity-binding substance that is attached to the solid surface, wherein the tagged DNA fragments or the amplified tagged DNA fragments are bound to the surface.

In some preferred embodiments, the affinity molecule is biotin and the affinity binding substance is avidin or streptavidin, or wherein the affinity molecule is digoxigenin and the affinity binding substance is an antibody that specifically binds digoxigenin.

In general, a method, composition, or kit of the invention is not limited to use of a particular transposase or DNA polymerase enzyme from a particular source. Rather, a method, composition, or kit of the present invention comprises any transposase or DNA polymerase enzyme from any source that has an equivalent enzymatic activity to the particular enzymes disclosed herein with respect to the particular method, composition, or kit. Still further, the methods of the present invention also include embodiments wherein any one particular enzyme that is provided and used in a step of the method is replaced by a combination of two or more enzymes which, when used in combination, whether used separately in a stepwise manner or used together at the same time reaction mixture, result in results that are identical to the results obtained using the one particular enzyme. The methods, buffers, and reaction conditions presented herein, including in the examples, are presently preferred for the embodiments of the methods, compositions, and kits of the present invention. However, other enzyme storage buffers, reaction buffers, and reaction conditions for use of some of the enzymes of the invention are known in the art, which may also be suitable for use in the present invention, and are included herein.

Library Amplification Primer

In some embodiments, the step of amplifying the library of tagged DNA fragments comprises performing a polymerase chain reaction (PCR), thereby generating an amplified library of tagged DNA fragments comprising amplified di-tagged DNA fragments. In some preferred embodiments, the PCR reaction is performed using a first PCR primer and a second PCR primer, each having a 3'-portion and a 5'-portion, wherein the 3'-portion of the first PCR primer is complementary to a sequence exhibited by the 3' tag in the di-tagged DNA fragments and the 3'-portion of the second PCR primer is complementary to a sequence that is complementary to a portion of the 5' tag, and wherein each 5' portion comprises a sequencing tag domain that comprises or consists of an appropriate sequencing tag that permits use of the amplified di-tagged DNA fragments generated as templates for next-generation sequencing using a particular next-generation sequencing platform (e.g., the Roche 454A and 454B sequencing tags, the ILLUMINA™ SOLEXA™ sequencing tags, the Applied Biosystems' SOLID™ sequencing tags, the Pacific Biosciences' SMRT™ sequencing tags, the Pollonator Polony sequencing tags, or the Complete Genomics sequencing tags, etc.). In some embodiments, the first PCR primer comprises a first sequencing tag and a first annealing tag, and the second PCR primer comprises a second sequencing tag, an experimental index tag and a second annealing tag. In some embodiments, the first and second sequencing tags can bind to complementary sequencing tags conjugated on a surface (e.g., a parallel sequencing flow cell surface). In some embodiments, the first annealing tag is at least about 80% (such as at least about any of 80%, 85%, 90%, 95%, 96%, 97%, 98%, 99%, or 100%) complementary to the amplification tag. In some embodiments, the second annealing tag is at least about 80% (such as at least about any of 80%, 85%, 90%, 95%, 96%, 97%, 98%, 99%, or 100%) complementary to a sequence that is complementary to the transferred transposon end sequence. In some embodiments, the first PCR primer comprises SEQ ID NO: 14. In some embodiments, the second PCR primer comprises a sequence selected from SEQ ID NOs: 15-20. Any of the available barcode sequences used during sequencing (e.g. barcodes from NEBNext® Multiplex Oligos for Illumina® Kit, Illumina® Multiplexing Sample Preparation Oligonucleotide Kit, or Nextera™ DNA Sample Prep Kits, KAPA DNA Library Preparation Kits, EpiNext DNA Library Preparation Kit, or PicoPLEX® DNA-seq Kit, etc.), or any combinations of A/T/G/C that can identify the samples/experiments while not affecting tagging/library preparation/sequencing, can be employed as experimental index tag. In some embodiments, the experimental index tag comprises a sequence selected from SEQ ID NOs: 24 and 33-37.

Sequencing Primer

In some embodiments, the library of amplified tagged DNA fragments is subjected to DNA sequencing or genome-wide sequencing. In some embodiments, the sequencing primers comprise a first sequencing primer that comprises a 3' end portion at least 80% (such as at least about any of 80%, 85%, 90%, 95%, 96%, 97%, 98%, 99%, or 100%) complementary to the amplification tag. In some embodiments, the first sequencing primer comprises SEQ ID NO: 21. In some embodiments, the sequencing primers comprise a second sequencing primer that comprises a 5' end portion at least 80% (such as at least about any of 80%, 85%, 90%, 95%, 96%, 97%, 98%, 99%, or 100%) complementary to the transferred transposon end sequence. In some embodiments, the second sequencing primer comprises SEQ ID NO: 22. In some embodiments, the sequencing primers further comprise a third sequencing primer (e.g., used for paired-end reads), comprising a 3' end portion at least 80% (such as at least about any of 80%, 85%, 90%, 95%, 96%, 97%, 98%, 99%, or 100%) complementary to a sequence that is complementary to the transferred transposon end sequence. In some embodiments, the third sequencing primer comprises SEQ ID NO: 23.

Starting from the sequence information obtained by sequencing the nucleic acid, molecular interactions can be identified using tools known in the art. For example, data may be analyzed using sequence comparison software that aligns sequenced nucleic acids to genomic sequences. Genomic sequences are generally known and obtainable from freely accessible data sources. A match of a sequenced nucleic acid, which is found in the sample to be analyzed, and a genomic sequence may be used as indicator that said sequenced nucleic acid is bound by a protein of interest, for example a histone or transcription factor, which is recognized by the agent binding to chromatin in the methods of the invention. Where the immunoprecipitating binding agent is a chemical substance, e.g. a drug, the match to a genomic sequence comprised in the nucleic acid fragment to be analyzed indicates binding of the chemical substance, e.g. drug, to a particular nucleic acid region comprised in chromatin.

Based on matching the sequenced nucleic acids to genomic sequences, statistical computational methods can be used to determine regions of significant binding to distinguish them from unspecific background signal. The identified regions can be used to further infer their biological role by correlating them to other datasets including gene-expression, genome annotation, gene ontology or other systems biology datasets.

By accumulating regions derived from said nucleic acid bound by the immunoprecipitating binding agent in particular the chemical substance, e.g. a drug, computational methods can also be used to determine significant sequence features of the said regions. Such approaches can be used to find enrichment for specific DNA binding motifs that are known to be bound by a specific transcription factor.

III. Articles of Manufacture and Kits

The invention also comprises kits and individual compositions for any of the methods of the invention. A kit is a combination of individual compositions useful for carrying out a method of the invention, wherein the compositions are optimized for use together in the method. A composition comprises an individual component or a blend of components for at least one step of a method of the invention. The invention comprises any kit that can be assembled from a combination of any two compositions of the invention, and any novel composition that is used in a kit or method of the invention. In some embodiments, the kit or composition comprises or consists of a subset of any kit or composition described here, in any appropriate combination and for any reason, such as to provide the user flexibility to adapt the method for a particular purpose or application, or to permit the user to employ other compositions together with the kit or composition comprising or consisting of the subset. Alternatively, a kit may be assembled from a single component or composition in a convenient use format, e.g., pre-aliquoted in single use portion, and may optionally include a set of instructions for use of the component or composition.

Thus in some embodiments, there is provided a kit for preparing nucleic acid sequencing library or tagmenting chromatin (or chromatin nucleic acids), comprising: (a) a transposase; (b) transposon end compositions. In some embodiments, there is provided a kit for preparing nucleic acid sequencing library or tagmenting chromatin (or chromatin nucleic acids), comprising: a transposome complex comprising (a) a transposase; and (b) transposon end compositions. In some embodiments, there is provided a kit for preparing nucleic acid sequencing library (and sequencing), comprising: (a) a transposase; (b) transposon end compositions; (c) PCR primers comprising a first PCR primer comprising SEQ ID NO: 14, and the second PCR primer comprising a sequence selected from SEQ ID NOs: 15-20; (d) sequencing primers comprising a first sequencing primer comprising SEQ ID NO: 21, and a second sequencing primer comprising SEQ ID NO: 22. In some embodiments, the kit further comprises a third sequencing primer comprising SEQ ID NO: 23. In some embodiments, the transposase is Tn5 (e.g., EZ-Tn5™). In some embodiments, the kit further comprises an CircLigase™ enzyme or *Methanobacterium* thermoautotrophicum RNA ligase 1 (MthRn1). In some embodiments, the kit further comprises an USER™ enzyme, or a mixture of Uracil DNA glycosylase (UDG) and the DNA glycosylase-lyase Endonuclease VIII. In some embodiments, the kit further comprises an Exo III. In some embodiments, the kit further comprises magnetic beads for DNA clean up.

EXEMPLARY EMBODIMENTS

Embodiment 1

A method of analyzing the binding sequences on a chromosome to which a protein of interest binds, comprising:
(a) randomly inserting a plurality of transposon end compositions comprising transposon end into the chromatin or double-stranded nucleic acid fragments thereof in the presence of a transposase;
(b) subjecting the double-stranded nucleic acid fragments inserted with transposon end compositions comprising transposon end to immunoprecipitation using an antibody specifically recognizing the protein of interest; and
(c) analyzing the nucleic acid fragment sequences to which the protein of interest binds.

Embodiment 2

The method of embodiment 1, wherein the protein of interest binds directly or indirectly to the chromatin.

Embodiment 3

The method of embodiment 1 or 2, wherein the protein of interest is selected from the group consisting of transcription factor, histone, histone modification, chromatin remodeler, chromatin modifier, transcription machinery elements, insulator binding protein such as CTCF.

Embodiment 4

The method of any one of embodiments 1-3, wherein step (a) further comprises extracting chromatin from a sample.

Embodiment 5

The method of any one of embodiments 1-4, wherein the chromatin in step (a) is cross-linked with a reversible cross-linking agent.

Embodiment 6

The method of embodiment 5, wherein the reversible cross-linking agent is formaldehyde.

Embodiment 7

The method of embodiment 6, wherein the final formaldehyde concentration during cross-linking is about 0.05% to about 1%.

Embodiment 8

The method of embodiment 7, wherein the final formaldehyde concentration during cross-linking is about 0.5%.

Embodiment 9

The method of embodiment 7 or 8, wherein the cross-linking time is no more than about 10 min.

Embodiment 10

The method of embodiment 9, wherein the cross-linking time is about 5 min to about 10 min.

Embodiment 11

The method of any one of embodiments 1-10, wherein the chromatin in step (a) is pre-fragmented before transposon insertion.

Embodiment 12

The method of embodiment 11, wherein the pre-fragmentation is generated by sonication or enzyme digestion.

Embodiment 13

The method of embodiment 12, wherein at least about 50% to about 95% of the fragmented chromatin is about 100 bp to about 5000 bp.

Embodiment 14

The method of embodiment 13, wherein at least about 50% to at least about 95% of the fragmented chromatin is about 100 bp to about 500 bp.

Embodiment 15

The method of any one of embodiments 1-14, wherein the transposase and transposon end compositions in step (a) are pre-incubated to form a transposome complex comprising a transposase and two transposon end compositions comprising transposon end.

Embodiment 16

The method of any one of embodiments 1-15, wherein the transposase in step (a) is from an organism selected from the group consisting of bacteria, plants, insects, or animals.

Embodiment 17

The method of embodiment 16, wherein the transposase is from bacteria.

Embodiment 18

The method of embodiment 17, wherein the transposase is an *E. coli* transposase.

Embodiment 19

The method of embodiment 18, wherein the transposase is Tn5.

Embodiment 20

The method of any one of embodiments 1-19, wherein the transposon end composition comprising transposon end further comprises an amplification tag and a restriction site tag, wherein the transposon end composition comprises, from 5' to 3': an amplification tag, a restriction site tag, and a transposon end.

Embodiment 21

The method of any one of embodiments 1-20, wherein the transposon end is a double-stranded nucleic acid.

Embodiment 22

The method of any one of embodiments 1-21, wherein the transferred strand of the transposon end comprises SEQ ID NO: 1.

Embodiment 23

The method of any one of embodiments 20-22, wherein the amplification tag is a single-strand nucleic acid.

Embodiment 24

The method of any one of embodiments 20-23, wherein the amplification tag comprises high GC content with a melting temperature Tm of about 65° C. in NEB Q5® DNA polymerase buffer.

Embodiment 25

The method of any one of embodiments 20-24, wherein the amplification tag comprises SEQ ID NO: 3.

Embodiment 26

The method of any one of embodiments 20-25, wherein the restriction site tag is a single-strand nucleic acid.

Embodiment 27

The method of any one of embodiments 20-26, wherein the restriction site tag is deoxyUridine (U).

Embodiment 28

The method of any one of embodiments 20-27, wherein the transposon end composition comprising amplification tag, restriction site tag, and transposon end further comprises one or more of a sample index tag, a unique molecular identifier tag, and an amplification facilitating tag at the 5' end of the transposon end.

Embodiment 29

The method of embodiment 28, wherein the transposon end composition comprises, from 5' to 3': a sample index tag, an unique molecular identifier tag, an amplification tag, a restriction site tag, an amplification facilitating tag, and a transposon end.

Embodiment 30

The method of embodiment 28 or 29, wherein the sample index tag is a single-strand nucleic acid.

Embodiment 31

The method of any one of embodiments 28-30, wherein the sample index tag comprises a sequence selected from SEQ ID NOs: 24-32.

Embodiment 32

The method of any one of embodiments 28-31, wherein the unique molecular identifier tag is a single-strand nucleic acid.

Embodiment 33

The method of any one of embodiments 28-32, wherein the unique molecular identifier tag comprises about 3 nt to about 20 nt random dNTP.

Embodiment 34

The method of embodiment 33, wherein the unique molecular identifier tag comprises about 5 nt random dNTP.

Embodiment 35

The method of any one of embodiments 28-34, wherein the amplification facilitating tag is a single-strand nucleic acid.

Embodiment 36

The method of any one of embodiments 28-35, wherein the amplification facilitating tag comprises SEQ ID NO: 4.

Embodiment 37

The method of any one of embodiments 28-36, wherein step (b) further comprises pooling at least two chromatin samples inserted with transposon end compositions comprising different sample index tags.

Embodiment 38

The method of any one of embodiments 1-37, wherein the antibody in step (b) can be one or more antibodies specifically recognizing different proteins of interest.

Embodiment 39

The method of any one of embodiments 1-37, wherein the antibody in step (b) can be one or more antibodies specifically recognizing the same protein of interest.

Embodiment 40

The method of any one of embodiments 1-39, wherein the antibody in step (b) are pre-incubated with beads compatible with immunoprecipitation assay.

Embodiment 41

The method of embodiment 40, wherein the beads are magnetic, Agarose, or other resin.

Embodiment 42

The method of any one of embodiments 1-41, wherein step (c) comprises sequencing the nucleic acid fragments.

Embodiment 43

The method of embodiment 42, wherein the sequencing primers comprise a first sequencing primer that can bind to at least a portion of the amplification tag.

Embodiment 44

The method of embodiment 43, wherein the first sequencing primer comprises SEQ ID NO: 21.

Embodiment 45

The method of embodiment 43 or 44, wherein the sequencing primers further comprise a second sequencing primer that can bind to at least a portion of the transposon end.

Embodiment 46

The method of embodiment 45, wherein the second sequencing primer comprises SEQ ID NO: 22.

Embodiment 47

The method of embodiment 45 or 46, wherein the sequencing primers further comprise a third sequencing primer comprising SEQ ID NO: 23.

Embodiment 48

The method of any one of embodiments 1-41, wherein step (c) comprises quantifying the nucleic acid fragments of interest.

Embodiment 49

The method of any one of embodiments 1-48, wherein step (c) further comprises denaturing the double-stranded nucleic acid fragments associated with the protein of interest specifically recognized by the antibody from step (b) into single-strand nucleic acid fragments.

Embodiment 50

The method of embodiment 49, wherein the denaturation is carried out by heating.

Embodiment 51

The method of any one of embodiments 1-50, wherein step (c) further comprises removing the protein of interest from the nucleic acid fragments.

Embodiment 52

The method of embodiment 51, wherein removing the protein of interest from the nucleic acid fragments is carried out by reverse-crosslinking.

Embodiment 53

The method of any one of embodiments 49-52, wherein the denaturing and/or reverse-crosslinking is carried out at about 95° C. for about 60 min.

Embodiment 54

The method of any one of embodiments 1-53, wherein step (c) further comprises removing nucleotide(s) from 3'-hydroxyl termini of the double-stranded nucleic acid fragments associated with the protein of interest until the nicking is blocked by the protein of interest or associated protein thereof.

Embodiment 55

The method of embodiment 54, wherein the nucleotide removing is carried out by a 3'→5' exonuclease.

Embodiment 56

The method of embodiment 55, wherein the 3'→5' exonuclease is Exonuclease III.

Embodiment 57

The method of any one of embodiments 49-56, wherein step (c) further comprises self-circularizing the single-strand nucleic acid fragments after denaturation.

Embodiment 58

The method of embodiment 57, wherein the self-circularization is carried out by a single-strand DNA (ssDNA) ligase.

Embodiment 59

The method of embodiment 58, wherein the ssDNA ligase is CircLigase™ or *Methanobacterium* thermoautotrophicum RNA ligase 1 (MthRn1).

Embodiment 60

The method of any one of embodiments 57-59, wherein step (c) further comprises linearizing the self-circularized single-strand nucleic acid fragments by generating a breakage at the restriction site tag.

Embodiment 61

The method of embodiment 60, wherein linearizing the self-circularized single-strand nucleic acid fragments by generating a breakage at the restriction site tag is carried out by USER™ enzyme, or a mixture of Uracil DNA glycosylase (UDG) and the DNA glycosylase-lyase Endonuclease VIII.

Embodiment 62

The method of embodiment 60 or 61, wherein step (c) further comprises PCR amplifying the linearized single-strand nucleic acid fragments.

Embodiment 63

The method of embodiment 62, wherein the PCR primers comprise a first PCR primer comprising a first sequencing tag and a first annealing tag, and a second PCR primer comprising a second sequencing tag, an experimental index tag and a second annealing tag.

Embodiment 64

The method of embodiment 63, wherein the first and second sequencing tags can bind to complementary sequencing tags conjugated on a surface.

Embodiment 65

The method of embodiment 64, wherein the surface is a parallel sequencing flow cell surface.

Embodiment 66

The method of any one of embodiments 63-65, wherein the first annealing tag can bind to at least a portion of the amplification tag, wherein the second annealing tag can bind to at least a portion of the transposon end.

Embodiment 67

The method of any one of embodiments 63-66, wherein the first PCR primer comprises SEQ ID NO: 14, and the second PCR primer comprises a sequence selected from SEQ ID NOs: 15-20.

Embodiment 68

The method of any one of embodiments 1-67, wherein the chromosome is from an organism selected from bacteria, plant, invertebrates, insects, fish, reptiles, amphibians, arachnids, avian, non-human mammals, and human.

Embodiment 69

A method of sequencing a nucleic acid sequence on a chromosome, comprising:
(a) randomly inserting a plurality of transposon end compositions comprising transposon end into the chromatin or double-stranded nucleic acid fragments thereof in the presence of a transposase, wherein the transposon end composition comprises, from 5' to 3': a sample index tag, an amplification tag, a restriction site tag, and a transposon end; and
(b) determining the nucleic acid fragment sequences.

Embodiment 70

The method of embodiment 69, wherein step (a) further comprises extracting chromatin from a sample.

Embodiment 71

The method of embodiment 69 or 70, wherein the chromatin in step (a) is cross-linked with a reversible cross-linking agent.

Embodiment 72

The method of embodiment 71, wherein the reversible cross-linking agent is formaldehyde.

Embodiment 73

The method of embodiment 72, wherein the final formaldehyde concentration during cross-linking is about 0.05% to about 1%.

Embodiment 74

The method of embodiment 73, wherein the final formaldehyde concentration during cross-linking is about 0.5%.

Embodiment 75

The method of embodiment 73 or 74, wherein the cross-linking time is no more than about 10 min.

Embodiment 76

The method of embodiment 75, wherein the cross-linking time is about 5 min to about 10 min.

Embodiment 77

The method of any one of embodiments 69-76, wherein the chromatin in step (a) is pre-fragmented.

Embodiment 78

The method of embodiment 77, wherein the pre-fragmentation is generated by sonication or enzyme digestion.

Embodiment 79

The method of embodiment 78, wherein at least about 50% to about 95% of the fragmented chromatin is about 100 bp to about 5000 bp.

Embodiment 80

The method of embodiment 79, wherein at least about 50% to at least about 95% of the fragmented chromatin is about 100 bp to about 500 bp.

Embodiment 81

The method of any one of embodiments 69-80, wherein the transposase and transposon end compositions in step (a) are pre-incubated to form a transposome complex comprising a transposase and two transposon end compositions comprising transposon end.

Embodiment 82

The method of any one of embodiments 69-81, wherein the transposase in step (a) is from an organism selected from the group consisting of bacteria, plants, insects, or animals.

Embodiment 83

The method of embodiment 82, wherein the transposase is from bacteria.

Embodiment 84

The method of embodiment 83, wherein the transposase is an *E. coli* transposase.

Embodiment 85

The method of embodiment 84, wherein the transposase is Tn5.

Embodiment 86

The method of any one of embodiments 69-85, wherein the transposon end is a double-stranded nucleic acid.

Embodiment 87

The method of any one of embodiments 69-86, wherein the transferred strand of the transposon end comprises SEQ ID NO: 1.

Embodiment 88

The method of any one of embodiments 69-87, wherein the sample index tag is a single-strand nucleic acid.

Embodiment 89

The method of any one of embodiments 69-88, wherein the sample index tag comprises a sequence selected from SEQ ID NOs: 24-32.

Embodiment 90

The method of any one of embodiments 69-89, wherein the amplification tag is a single-strand nucleic acid.

Embodiment 91

The method of any one of embodiments 69-90, wherein the amplification tag comprises high GC content with a melting temperature Tm of about 65° C. in NEB Q5® DNA polymerase buffer.

Embodiment 92

The method of any one of embodiments 69-91, wherein the amplification tag comprises SEQ ID NO: 3.

Embodiment 93

The method of any one of embodiments 69-92, wherein the restriction site tag is a single-strand nucleic acid.

Embodiment 94

The method of any one of embodiments 69-93, wherein the restriction site tag is deoxyUridine (U).

Embodiment 95

The method of any one of embodiments 69-94, wherein the transposon end composition comprising sample index tag, amplification tag, restriction site tag, and transposon end further comprises one or both of a unique molecular identifier tag and an amplification facilitating tag at the 5' end of the transposon end.

Embodiment 96

The method of embodiment 95, wherein the transposon end composition comprises, from 5' to 3': a sample index tag, an unique molecular identifier tag, an amplification tag, a restriction site tag, an amplification facilitating tag, and a transposon end.

Embodiment 97

The method of any one of embodiments 69-96, wherein the unique molecular identifier tag is a single-strand nucleic acid.

Embodiment 98

The method of any one of embodiments 69-97, wherein the unique molecular identifier tag comprises about 3 nt to about 20 nt random dNTP.

Embodiment 99

The method of embodiment 98, wherein the unique molecular identifier tag comprises about 5 nt random dNTP.

Embodiment 100

The method of any one of embodiments 95-99, wherein the amplification facilitating tag is a single-strand nucleic acid.

Embodiment 101

The method of any one of embodiments 95-100, wherein the amplification facilitating tag comprises SEQ ID NO: 4.

Embodiment 102

The method of any one of embodiments 69-101, wherein step (b) further comprises pooling at least two chromatin samples inserted with transposon end compositions comprising different sample index tags.

Embodiment 103

The method of any one of embodiments 69-102, wherein step (b) comprises sequencing the nucleic acid fragments.

Embodiment 104

The method of embodiment 103, wherein the sequencing primers comprise a first sequencing primer and a second sequencing primer, wherein the first sequencing primer can bind to at least a portion of the amplification tag, wherein the second sequencing primer can bind to at least a portion of the transposon end.

Embodiment 105

The method of embodiment 104, wherein the sequencing primers comprise a first sequencing primer comprising SEQ ID NO: 21.

Embodiment 106

The method of embodiment 105, wherein the sequencing primers further comprise a second sequencing primer comprising SEQ ID NO: 22.

Embodiment 107

The method of embodiment 106, wherein the sequencing primers further comprise a third sequencing primer comprising SEQ ID NO: 23.

Embodiment 108

The method of any one of embodiments 69-102, wherein step (b) comprises quantifying the nucleic acid fragment of interest.

Embodiment 109

The method of any one of embodiments 69-108, wherein step (b) further comprises denaturing the double-stranded nucleic acid fragments from step (a) into single-strand nucleic acid fragments.

Embodiment 110

The method of embodiment 109, wherein the denaturation is carried out by heating.

Embodiment 111

The method of any one of embodiments 69-110, wherein step (b) further comprises removing any protein associated with the nucleic acid fragments.

Embodiment 112

The method of embodiment 111, wherein removing the protein from the nucleic acid fragments is carried out by reverse-crosslinking.

Embodiment 113

The method of any one of embodiments 109-112, wherein the denaturing and/or reverse-crosslinking is carried out at about 95° C. for about 60 min.

Embodiment 114

The method of any one of embodiments 69-113, wherein step (b) further comprises removing nucleotide(s) from 3'-hydroxyl termini of the double-stranded nucleic acid fragments associated with the protein of interest until the nicking is blocked by the protein of interest or associated protein thereof.

Embodiment 115

The method of embodiment 114, wherein the nucleotide removing is carried out by a 3'→5' exonuclease.

Embodiment 116

The method of embodiment 115, wherein the 3'→5' exonuclease is Exonuclease III.

Embodiment 117

The method of any one of embodiments 109-116, wherein step (b) further comprises self-circularizing the single-strand nucleic acid fragments after denaturation.

Embodiment 118

The method of embodiment 117, wherein the self-circularization is carried out by a single-strand DNA (ssDNA) ligase.

Embodiment 119

The method of embodiment 118, wherein the ssDNA ligase is CircLigase™ or *Methanobacterium* thermoautotrophicum RNA ligase 1 (MthRn1).

Embodiment 120

The method of any one of embodiments 117-119, wherein step (b) further comprises linearizing the self-circularized single-strand nucleic acid fragments by generating a breakage at the restriction site tag.

Embodiment 121

The method of embodiment 120, wherein linearizing the self-circularized single-strand nucleic acid fragments by generating a breakage at the restriction site tag is carried out by USER™ enzyme or a mixture of Uracil DNA glycosylase (UDG) and the DNA glycosylase-lyase Endonuclease VIII.

Embodiment 122

The method of embodiment 120 or 121, wherein step (b) further comprises PCR amplifying the linearized single-strand nucleic acid fragments.

Embodiment 123

The method of embodiment 122, wherein the PCR primers comprise a first PCR primer comprising a first sequencing tag and a first annealing tag, and a second PCR primer comprising a second sequencing tag, an experimental index tag and a second annealing tag.

Embodiment 124

The method of embodiment 123, wherein the first and second sequencing tags can bind to complementary sequencing tags conjugated on a surface.

Embodiment 125

The method of embodiment 124, wherein the surface is a parallel sequencing flow cell surface.

Embodiment 126

The method of any one of embodiments 123-125, wherein the first annealing tag can bind to at least a portion of the amplification tag, wherein the second annealing tag can bind to at least a portion of the transposon end.

Embodiment 127

The method of any one of embodiments 123-126, wherein the first PCR primer comprises SEQ ID NO: 14, and the second PCR primer comprises a sequence selected from SEQ ID NOs: 15-20.

Embodiment 128

The method of any one of embodiments 69-108, wherein the chromatin is from an organism selected from bacteria, plant, invertebrates, insects, fish, reptiles, amphibians, arachnids, avian, non-human mammals, and human.

Embodiment 129

A transposon end composition comprising, from 5' to 3': an amplification tag, a restriction site tag, and a transposon end.

Embodiment 130

The transposon end composition of embodiment 129, wherein the transposon end is double-stranded nucleic acid.

Embodiment 131

The transposon end composition of embodiment 129 or 130, wherein the transferred strand of the transposon end comprises SEQ ID NO: 1.

Embodiment 132

The transposon end composition of any one of embodiments 129-131, wherein the amplification tag is a single-strand nucleic acid.

Embodiment 133

The transposon end composition any one of embodiments 129-132, wherein the amplification tag comprises SEQ ID NO: 3.

Embodiment 134

The transposon end composition of any one of embodiments 129-133, wherein the restriction site tag is a single-strand nucleic acid.

Embodiment 135

The transposon end composition of any one of embodiments 129-134, wherein the restriction site tag is deoxyUridine (U).

Embodiment 136

The transposon end composition of any one of embodiments 129-135, further comprises one or more of a sample index tag, a unique molecular identifier tag, and an amplification facilitating tag at the 5' end of the transposon end.

Embodiment 137

The transposon end composition of embodiment 136, wherein the transposon end composition comprises, from 5' to 3': a sample index tag, an unique molecular identifier tag, an amplification tag, a restriction site tag, an amplification facilitating tag, a transposon end.

Embodiment 138

The transposon end composition of embodiment 136 or 137, wherein the sample index tag is a single-strand nucleic acid.

Embodiment 139

The transposon end composition of any one of embodiments 136-138, wherein the sample index tag comprises a sequence selected from SEQ ID NOs: 24-32.

Embodiment 140

The transposon end composition of any one of embodiments 136-139, wherein the unique molecular identifier tag is a single-strand nucleic acid.

Embodiment 141

The transposon end composition of any one of embodiments 136-140, wherein the unique molecular identifier tag comprises about 3 nt to about 20 nt random dNTP.

Embodiment 142

The transposon end composition of embodiment 141, wherein the unique molecular identifier tag comprises about 5 nt random dNTP.

Embodiment 143

The transposon end composition of any one of embodiments 136-142, wherein the amplification facilitating tag is a single-strand nucleic acid.

Embodiment 144

The transposon end composition of any one of embodiments 136-143, wherein the amplification facilitating tag comprises SEQ ID NO: 4.

Embodiment 145

A transposome complex comprises a transposase and two transposon end compositions of any one of embodiments 129-144.

Embodiment 146

A kit for preparing nucleic acid sequencing library, comprising:
(a) a transposase;
(b) transposon end compositions of any one of embodiments 129-144;
(c) PCR primers comprising a first PCR primer comprising SEQ ID NO: 14, and the second PCR primer comprising a sequence selected from SEQ ID NOs: 15-20; and
(d) sequencing primers comprising a first sequencing primer comprising SEQ ID NO: 21, and a second sequencing primer comprising SEQ ID NO: 22.

Embodiment 147

The kit of embodiment 146, wherein the transposase is Tn5.

Embodiment 148

The kit of embodiment 146 or 147, further comprises an CircLigase™ enzyme or *Methanobacterium* thermoautotrophicum RNA ligase 1 (MthRn1).

Embodiment 149

The kit of any one of embodiments 146-148, further comprises an USER™ enzyme, or a mixture of Uracil DNA glycosylase (UDG) and the DNA glycosylase-lyase Endonuclease VIII.

Embodiment 150

The kit of any one of embodiments 146-149, further comprises an Exonuclease III.

Embodiment 151

The kit of any one of embodiments 146-150, further comprises magnetic beads for DNA clean up.

EXAMPLES

The examples below are intended to be purely exemplary of the invention and should therefore not be considered to limit the invention in any way. The following examples and detailed description are offered by way of illustration and not by way of limitation.

Materials and Methods

Provided herein are exemplary buffers and reagents used in some embodiments of the present invention.

| Shearing buffer | |
| --- | --- |
| Reagent | Final |
| 1M Tris HCl, pH 8.0 | 100 mM |
| 5M NaCl | 140 mM |
| 0.5M EDTA | 0.5 mM |

| Shearing buffer (continued) | |
| --- | --- |
| Reagent | Final |
| 0.5M EGTA | 0.25 mM |
| 10% Triton X-100 | 0.5% |
| 10% Na Deoxycholate | 0.05% |
| 10% SDS | 0.02% |
| 10% N-lauroylsarcosine | 0.1% |

*Protease inhibitor is added before use

| 6× ChIP buffer | |
| --- | --- |
| Reagent | Final |
| 1M HEPES pH 7.5 | 60 mM |
| 5M NaCl | 700 mM |
| 0.5M EDTA | 6 mM |
| 0.5M EGTA | 3 mM |
| 10% Triton X-100 | 5% |
| 10% Na Deoxycholate | 0.6% |
| 10% SDS | 0.6% |
| 10% N-lauroylsarcosine | 3% |

*Protease inhibitor is added before use

| 1$^{st}$ washing buffer | |
| --- | --- |
| Reagent | Final |
| 1M Tris HCl pH 8.0 | 20 mM |
| 5M NaCl | 150 mM |
| 0.5M EDTA | 2 mM |
| 10% Triton X-100 | 1% |
| 10% SDS | 0.1% |

| 2$^{nd}$ washing buffer | |
| --- | --- |
| Reagent | Final |
| 1M Tris HCl pH 8.0 | 20 mM |
| 5M NaCl | 500 mM |
| 0.5M EDTA | 2 mM |
| 10% Triton X-100 | 1% |
| 10% SDS | 0.1% |

| 3$^{rd}$ washing buffer | |
| --- | --- |
| Reagent | Final |
| 1M Tris HCl pH 8.0 | 20 mM |
| 5M LiCl | 250 mM |
| 0.5M EDTA | 2 mM |
| 10% Triton X-100 | 1% |
| 10% NP-40 | 0.1% |
| 10% Na deoxycholate | 0.5% |
| 10% SDS | 0.1% |

| HEGX buffer | |
| --- | --- |
| Reagent | Final |
| 1M HEPES, pH 7.5 | 50 mM |
| 5M NaCl | 800 mM |

-continued

HEGX buffer

| Reagent | Final |
| --- | --- |
| 0.5M EDTA | 1 mM |
| 10% Triton X-100 | 0.1% |
| Glycerol | 10% |

Storage buffer

| Reagent | Final |
| --- | --- |
| 1M Tris HCl pH 7.5 | 50 mM |
| 5M NaCl | 100 mM |
| 0.5M EDTA | 0.1 mM |
| Glycerol | 50% |

TA Reaction buffer

| Reagent | Final |
| --- | --- |
| Tris-acetate pH 7.6 | 33 mM |
| KOAc | 66 mM |
| Mg(OAc)$_2$ | 10 mM |
| spermidine | 4 mM |

Regular ChIP buffer

| Reagent | Final |
| --- | --- |
| 1M HEPES pH 7.5 | 15 mM |
| 5M NaCl | 140 mM |
| 0.5M EDTA | 1 mM |
| 0.5M EGTA | 0.5 mM |
| 10% Triton X-100 | 1% |
| 10% Na Deoxycholate | 0.1% |
| 10% SDS | 0.1% |
| 10% N-lauroylsarcosine | 0.5% |

Elution buffer

| Reagent | Final |
| --- | --- |
| 1M Tris-HCl, pH 7.5 | 50 mM |
| 0.5M EDTA | 1 mM |
| 10% SDS | 0.5% |

Commercial reagents

| Name | Cat. # | Company |
| --- | --- | --- |
| SureBeads Protein A/G Beads | 1614013 or 1614023 | Bio-Rad |
| EZ-Tn5 ™ Transposase | TNP92110 | Epicentre (an Illumina Company) |
| CircLigase ™ ssDNA Ligase | CL4111K or CL4115K | Epicentre (an Illumina Company) |
| USER ™ Enzyme | M5505S or M5505L | NEB |
| EXO III | M0206S or M0206L | NEB |
| NEBNext Q5 Master Mix | M0543S or M0543L | NEB |
| Agencourt AMPure XP | A63880 or A63881 | Beckman Coulter |

Example 1. Tn5 Purification

Protein Production

BL21 (DE3)—pTXB1. Tn5 colony was picked into 50 mL LB and grown overnight with ampicillin. 1 L LB was inoculated to OD$_{600}$ 0.05 and grown to OD$_{600}$ 0.6-0.9. 500 μM IPTG was added to induce Tn5 expression. Bacterial culture was allowed to continue growing at 37° C. for 3 h till OD$_{600}$ reached about 3.0 or at 18° C. overnight. Cells were harvested and spinned down, the cell pellet could be stored at −80° C.

Protein Purification (Performed on Ice or in Cold Room)

Cells were resuspended with HEGX+proteinase inhibitor (p8849 1:100) 20 ml/1 L cell culture. Cells were lysed by sonication: output 20%, 1 s On/5 s Off for 30 s, repeated for 6 times. The cell lysate was clarified by centrifugation at 15,000×g for 30 min. 10% PEI was then added with constant stirring to 0.1% final concentration (200 μl for 1 L culture) and centrifuged at 15,000×g for 30 min. Chitin resin was washed with HEGX 5 times by centrifugation, then mixed with the cell culture supernatant in 0.1% PEI, rotated for 1 h. Chitin resin was washed with HEGX+p8849 (1:200) three times, then the bead and solution mixture was loaded onto a column. The Chitin resin on column was washed at 1 mL/min with 30 columns volumes (CV) HEGX with p8849 (1:1000), then with 2 CV HEGX+100 mM DTT, and drained the buffer to the top of the resin. ½ CV HEGX+100 mM DTT was added to the column to wash in the DTT solution. The column was closed 48 h at 4° C. to allow intein cleavage. Elution from the column (1$^{st}$ elution) was collected. The column was further eluted with 1 CV HEGX 6 times. The resin was kept with 1 CV HEGX+100 mM DTT for further cleavage, in case no sufficient cleavage. Protein concentration was measured at A$_{280}$, and the resin portion was checked by running a SDS gel. Different protein elution fractions were pooled. The protein was concentrated by spinning in Centricon YM10, and diluted to desired concentration with storage buffer (see Materials).

Example 2. Assembling Transposon End Composition and Tn5 Transposase

Each indexed transferred transposon end oligo (e.g., from Table 1, SEQ ID NOs: 5-13; or other designed oligos described in below Examples) were mixed with non-transferred transposon end oligo (SEQ ID NO: 2) at a 1:1 molar ratio at a final stock concentration of 40 μM in 200 mM Tris-HCl, pH 8.0. The oligo pairs were annealed by heating at 95° C. for 5 min, followed by a slow decrease in temperature to 20° C. at −0.1° C./s. Pre-cooled 100% glycerol was added to each annealed oligos (transposon end compositions), and stored at −20° C.

3 μL annealed oligos in glycerol were mixed with 100 μL EZ-Tn5™ Transposase, and incubated at 20° C. for 1 h. The assembled transposome complex comprising the Tn5 transposase and indexed transposon end composition was stored at −20° C. for later use.

Example 3. The Length of Transposon End Composition Oligonucleotide Affects Tn5 Activity Transposon end composition oligonucleotides with different lengths (vary in amplification tag lengths) were ordered from Integrated DNA Technologies (IDT). The transferred strand and non-transferred strand were annealed and assembled with Tn5 purified as in Example 1. Same Molar concentration of transposon end composition oligos with varying lengths pre-assembled with same Molar concentration of Tn5 (see Examples 1 and 2 for Tn5 purification and assembling) were added to the same amount of plasmid DNA (T-vector) to test the effect of the length of transposon end composition oligonucleotide on Tn5 activity.

As can be seen from FIG. 5, with the same Molar concentration of transposon end composition oligos, the longer the oligos, the more free oligos are left unassembled, and the bigger the size of the tagmented DNA. The ideal oligo size for assembling Tn5 should be less than about 50 nt.

Example 4. Detergent Affects Tn5 Activity

To test the effect of detergent on Tn5 activity, oligos SEQ ID NO: 2 and SEQ ID NO: 6 were annealed and assembled with Tn5 (see methods in Example 2) and used in the following experiments for either chromatin of Ciona embryos or plasmid DNA.

Ciona embryos were washed with PBS once, crosslinked with fresh prepared 1% formaldehyde in PBS for 10 min. Cross-linking was quenched with 2.5M glycine at final concentration of 0.125M for 10 min on ice. Cells were centrifuged for 5 min at 2,000 g at 4° C. Supernant was discarded, and the pellet was subjected for chromatin shearing (Ciono embryo homogenization before shearing is optional).

Effect of Different SDS Concentrations on Tn5 Activity

For testing Tn5 activity in the absence SDS (FIG. 6A, "chromatin without SDS" lanes), Ciona embryo pellets were washed with PBS once, resuspended in TA Reaction buffer (see Materials) without detergent, then chromatin was briefly sheared in 100 μL TA Reaction buffer without detergent with sonicator for 30 seconds, 60 seconds, or 90 seconds. Then 0 μL, 8 μL (2 pmol), or 16 μL (4 pmol) of assembled Tn5 transposome complex was added into the 100 differentially sonicated chromatin, and incubated at 37° C. on thermoshaker for 60 min.

For testing Tn5 activity in the presence of SDS (FIG. 6A, "chromatin with 0.1% SDS" lanes), Ciona embryo pellets were washed with TA Reaction buffer with 0.1% SDS once, resuspended in TA Reaction buffer with 0.1% SDS, then chromatin was briefly sheared in 100 μL TA Reaction buffer with 0.1% SDS with sonicator for 30 seconds. Then 8 μL (2 pmol) or 16 μL (4 pmol) of assembled Tn5 transposome complex was added into the 100 μL sonicated chromatin, and incubated at 37° C. on thermoshaker for 60 min.

As a control, 80 ng plasmid DNA (T vector) in TA Reaction buffer without detergent was incubated with 8 (2 pmol) or 16 μL (4 pmol) of assembled Tn5 transposome complex, and incubated at 37° C. on thermoshaker for 60 min.

As can be seen from FIG. 6A, Tn5 could be used for tagmenting cross-linked chromatin with no or little SDS (see lanes marked "Chromatin without SDS" and "Chromatin with 0.1% SDS"), although the sonication efficiency in the absence of SDS significantly dropped (compare lanes "Chromatin without SDS" 30 s sonication 8/16 μL and "Chromatin with 0.1% SDS" 30 s sonication 8/16 μL; also compare the lane of "Chromatin without SDS" 90 s sonication with "0" Tn5 in FIG. 6A and lanes sheared 80 s in regular ChIP buffer with 0.1% SDS and Shearing buffer with 0.02% SDS in FIG. 6B). See FIG. 6B for Ciona chromatin sonication comparison using either regular ChIP buffer (has 0.1% SDS) or Shearing buffer (has 0.02% SDS), demonstrating that the 0.02% of SDS can have similar sonication shearing effect as higher concentration of SDS. SDS amount above 0.05% was found to kill Tn5 chromatin-incorporation activity (see lanes marked "Chromatin with 0.1% SDS"), as demonstrated by the significant amount of free Tn5 oligos at the bottom of the gel. As a control, DNA plasmid was efficiently tagmented with Tn5 transposome complex. Thus, in later Examples, the SDS concentration in the Shearing buffer was designed to be less than 0.05% (final, after dilution) for tagmentation.

Effect of Different Detergent on Tn5 Activity

Since sonication needs detergents to be present in order to achieve higher efficiency, the effect of different detergents on Tn5 activity was further tested on plasmid DNA (T vector). Shearing buffers without any detergent, or with different amounts of Triton, Na deoxycholate, or N-lauroylsarcosine were prepared.

Index-tagmentation using different Shearing buffer (with or without detergent) was set up as below, and incubated at 37° C. on thermoshaker for 60 min.

| | |
|---|---|
| 100 mM MgCl$_2$ | 30 μl |
| Plasmid DNA in Shearing buffer | 60 μl |
| Indexed bidirectional Tn5 transposome complex | 16 μl (4 pmol) |
| H$_2$O | 184 μl |

As can be seen from FIG. 7, the normally used concentrations of all three detergents (these detergents are normally used in ChIP shearing buffer) all affected Tn5 tagmentation efficacy, especially when N-lauroylsarcosine was present (a concentrated band of fixed size rather than a smear (see "TA Reaction buffer" lane and "ChIP Shearing buffer without detergent" lane) on the gel).

Effect of Dilution of Shearing Buffer on Tn5 Activity

Since both SDS and N-lauroylsarcosine are critical detergents for shearing chromatin, the effect of dilution of the Shearing buffer was tested on Tn5 tagmentation activity. Shearing buffers were prepared with different final concentrations of SDS and N-lauroylsarcosine. Then the Shearing buffer was diluted 5 times or 10 times, to mimic the final concentrations of SDS and N-lauroylsarcosine used after fragmenting with sonicator and before tagmenting with Tn5 transposome complexes.

Index-tagmentation using different diluted Shearing buffer was set up as below, and incubated at 37° C. on thermoshaker for 60 min.

| | |
|---|---|
| 100 mM MgCl$_2$ | 30 μl |
| 80 ng plasmid DNA in diluted Shearing buffer | X μl |
| Indexed bidirectional Tn5 transposome complex | 20 μl |
| H$_2$O | Y μl |
| Total | 300 μl |

Untreated plasmid DNA was used as a control. As can be seen from FIG. 8, less initial amount of SDS and N-lauroylsarcosine in the Shearing buffer, and more dilution before Tn5 tagmentation showed the best Tn5 tagmentation activity (darker smear towards smaller DNA size). Thus, the working solution of Shearing buffer used in this invention was optimized to contain final concentrations of SDS of 0.02%, and N-lauroylsarcosine of 0.1%

Example 5. Exemplary ChIP-SMITH Workflow

This example provides an exemplary protocol of ChIP-SMITH (see FIG. 2).

Cells (demonstrated with Ciona embryos) were washed with PBS once, crosslinked with fresh prepared 1% formaldehyde in PBS for 10 min. Cross-linking was quenched with 2.5M glycine at final concentration of 0.125M for 10 min on ice. Cells were centrifuged for 5 min at 2,000 g at 4° C. Supernant was discarded, and the pellet was subjected for ChIP (pellet can be stored at −80° C.).

SureBeads were prepared for ChIP following Bio-Rad manual. Briefly, SureBeads were thoroughly resuspended in their solution by vortexing, and 100 µl washed SureBeads were transferred to 1.5 ml EP tubes. Beads were stabilized with magnets, and supernatant was discarded. The beads were washed with 1 ml PBS-BSA (0.5%) three times, 10 µg antibodies in 1 ml PBS-BSA was added to the beads, rotated for 2 h at 4° C. Beads were washed with 1 ml PBS-BSA three times, then supernatant was removed.

Cell pellets were washed with Shearing buffer (see Materials; the Shearing buffer composition was made for efficient sonication, and did not compromise tagmentation after 5 fold dilution) once, resuspended in Shearing buffer, then chromatin was briefly sheared in Shearing buffer with sonicator (brief shearing is preferred for increasing the accessibility of transposome complexes without introducing bias; if using embryos, can optionally homogenize before sonication). A small portion of sheared chromatin was isolated as control (for preparing input DNA library). Index-tagmentation for each biological sample was set up as below, and incubated at 37° C. on thermoshaker for 60 min.

| | |
|---|---|
| 100 mM MgCl$_2$ | 30 µl |
| 50 × PI (protease inhibitor) | 10 µl |
| Chromatin in Shearing buffer | 60 µl |
| Indexed bidirectional Tn5 transposome complex | 20 µl |
| H$_2$O | 180 µl |

60 µL 6× ChIP buffer (see Materials) was added into each sample to quench index-tagmentation. Indexed samples were pooled together into a 1.5 ml EP tube. Antibody-coated beads were added to the pooled samples and allowed for ChIP overnight (pooled samples can be aliquoted for different ChIP experiments; for limited materials, regularly sonicated chromatin can be added into the pooled sample as carrier chromatin).

Beads were washed with 1$^{st}$ washing buffer twice, then washed with 2$^{nd}$ washing buffer twice. Beads were then resuspended with 3$^{rd}$ washing buffer, then beads were transferred to PCR tube. These modified washing buffers were able to efficiently remove un-incorporated transposon end compositions (or transposome complex).

The beads were washed with 1×NEBuffer 1.0, then freshly prepared Exo III digestion solution was added as below. Digestion was pursued at 37° C. for 20 min, the Exo III was deactivated along with reverse crosslinking at 95° C. for 60 min (Exo III digestion was designed for cleaning up any un-incorporated transposon end compositions, but it also increased the resolution of ChIP-SMITH).

| | |
|---|---|
| 10 × NEBuffer 1.0 | 2 µl |
| EXO III | 0.5 µl |
| H$_2$O | 17.5 µl |

Digested DNA was then transferred into a new PCR tube, and was set up for self-ligation (self-circularization) reaction as below. Self-ligation was carried out at 60° C. for 1 hour, then the CircLigase was deactivated by heating at 80° C. for 20 min.

| | |
|---|---|
| Reverse crosslinked ssDNA | 20 µl |
| 1 mM ATP | 1.25 µl |
| 50 mM MnCl$_2$ | 1.25 µl |
| CircLigase | 1 µl |
| 0.5M Tris 8.0 | 1.5 µl |

1 µl USER enzyme was then added to the circularized ssDNA, and incubated at 37° C. for 15 min (all reactions, from Exo III to USER digestion, all had compatible buffers which avoided DNA clean up in between, greatly decreasing DNA loss). USER digestion was employed to avoid the step of annealing reverse complementary oligos (like in iCLIP (König J et al., Nat Struct Mol Biol. 2010 July; 17(7): 909-15)).

DNA was cleaned up with 60 µl Agencourt AMPure XP beads following the manual. Beads capturing DNA were resuspended with 18 µl H$_2$O, and 16 µl of supernatant was transferred into a new PCR tube to set up the below reaction (also see FIG. 4). See Table 2 for PCR primer sequences.

| | |
|---|---|
| NEBNext Q5 Hot Start HiFi Master Mix | 20 µl |
| DNA (beads purified) | 16 µl |
| Primer SMITHP5 | 2 µl |
| Primer SMITHP7.X | 2 µl |

PCR program was set up as below:

| | | | |
|---|---|---|---|
| Step 1 | 98° C. | 30 s | |
| Step 2 | 98° C. | 10 s | |
| Step 3 | 65° C. | 75 s | back to Step 2 for 15-18 cycles |
| Step 4 | 65° C. | 5 min | |
| Step 5 | 4° C. | hold | |

Amplified DNA (library) was cleaned up with 60 µl Agencourt AMPure XP beads following manual. Due to the low efficiency of self-ligating ssDNA above 500 nt, which has similar outcome of size selection step to get rid of big fragments, size selection with AMPure beads was optional to obtain desired sizes of DNA. Library size was checked with Bioanalyzer. The DNA library was then subjected to next-generation sequencing. Sequencing primers are provided in Table 3 (also see FIG. 4).

Example 6. ChIP-SMITH has Similar Quality as Traditional ChIP-Seq

Ciona embryos were washed with PBS once, crosslinked with fresh prepared 1% formaldehyde in PBS for 10 min. Cross-linking was quenched with 2.5M glycine at final concentration of 0.125M for 10 min on ice. Cells were centrifuged for 5 min at 2,000 g at 4° C. Supernatant was discarded, and the pellet was subjected for ChIP (pellet can be stored at −80° C.).

SureBeads were prepared for ChIP following Bio-Rad manual. Briefly, SureBeads were thoroughly resuspended in their solution by vortexing, and 100 µl washed SureBeads were transferred to 1.5 ml EP tubes. Beads were stabilized with magnets, and supernatant was discarded. The beads were washed with 1 ml PBS-BSA (0.5%) three times, 10 µg anti-RNA polymerase II antibodies (Active motif, Catalog No: 39097) in 1 ml PBS-BSA was added to the beads, rotated for 2 h at 4° C. Beads were washed with 1 ml PBS-BSA three times, then supernatant was removed.

Ciona embryos pellets were washed with Shearing buffer (see Materials) once, resuspended in Shearing buffer, then chromatin was briefly sheared in Shearing buffer with sonicator. A small portion of sheared chromatin was isolated as control (for preparing input DNA library).

Regular ChIP-Seq

Antibody-coated beads were added to sheared chromatin and allowed for ChIP overnight.

Beads carrying ChIPed chromatin were washed with $1^{st}$ washing buffer without SDS twice, with $2^{nd}$ washing buffer without SDS twice, and $3^{rd}$ washing buffer without SDS once, then beads were resuspended with 200 µl Elution buffer (see Materials). 4 µl proteinase K was added into the resuspended beads, and reverse crosslinked at 65° C. for >6 hr. The beads were then centrifuged, and reverse-crosslinked DNA in the supernatant was recovered by phenol-chloroform extraction. Input DNA was similarly cross-linked and purified.

Purified DNA was transferred to PCR tubes, and library preparation was performed using NEBNext® ChIP-Seq Library Prep Reagent Set for Illumina® following Instruction Manual. DNA cleanup and library size selection were performed according to the Manual using AMPure® XP beads. Library size was checked with Bioanalyzer. The DNA library was then subjected to next-generation sequencing on HiSeq 2500 Platform using standard Illumina sequencing primers.

Index-Tagmented ChIP-Seq Using Modified Nextera® Dual-Transposon Design

See FIG. 10 for an exemplary workflow.

The modified Nextera® dual-transposon design was performed as below. Oligos as shown in Table 4 were designed and ordered from IDT (SEQ ID NOs: 39 and 42 demonstrate general design). As can be seen from FIG. 10, the 3' end of the transferred strand oligo was the same as that in Nextera® Tn5 transposome complex; 4 barcode nucleic acids were introduced to minimize the length of the transferred strand oligo; the connector sequence at the 5' end was designed for annealing with NEBNext® Multiplex Oligos as well as regular Illumina PCR primers. For Tn5-A transposon end compositions, oligos Tn5-A.1 (SEQ ID NO: 40) or Tn5-A.2 (SEQ ID NO: 41) was annealed with non-transferred transposon end oligo (SEQ ID NO: 2). For Tn5-B transposon end compositions, oligos Tn5-B.1 (SEQ ID NO: 43) or Tn5-B.2 (SEQ ID NO: 44) was annealed with non-transferred transposon end oligo (SEQ ID NO: 2). Then Tn5-A transposon end compositions and Tn5-B transposon end compositions were mixed together with the same ratio, and assembled with Tn5 as shown in Example 2, resulting in Tn5 transposome complexes Tn5-AA, Tn5-AB, and Tn5-BB (see Step 2 in FIG. 10). Two sets of dual-design Tn5 transposome complexes were prepared, each set with different sample barcode.

Index-tagmentation for each briefly sheared Ciona chromatin (two replicates) was set up as below, and incubated at 37° C. on thermoshaker for 60 min. Each replicate was individually index-tagmented with one set of dual-design Tn5 transposome complex, so that the 2 replicates can be distinguished.

| 100 mM MgCl$_2$ | 30 µl |
| 50 × PI (protease inhibitor) | 10 µl |
| Chromatin in Shearing buffer | 60 µl |
| Modified dual-design Tn5 transposome complex | 20 µl |
| H$_2$O | 180 µl |

60 µL 6× ChIP buffer (see Materials) was added into each sample to quench index-tagmentation, 2 samples were pooled, and transferred into a 1.5 ml EP tube. Antibody-coated beads were added and allowed for ChIP overnight.

Beads carrying ChIPed chromatin were washed with $1^{st}$ washing buffer twice, with $2^{nd}$ washing buffer twice, and $3^{rd}$ washing buffer once, then beads were resuspended with 200 µl Elution buffer. 4 µl proteinase K was added into the resuspended beads, and reverse crosslinked at 65° C. for >6 hr. The beads were then centrifuged, and reverse-crosslinked DNA in the supernatant was recovered by phenol-chloroform extraction. Input DNA was similarly cross-linked and purified.

Purified tagged DNA was transferred to PCR tubes. Then these tagged DNA were PCR amplified using Nextera® Multiplex Oligos following Instruction Manual. Library size was checked with Bioanalyzer. The DNA library was then subjected to next-generation sequencing on HiSeq 2500 platform using standard Illumina sequencing primers.

ChIP-SMITH Followed by Sequencing

Index-tagmentation for briefly sheared Ciona chromatin was set up as below, and incubated at 37° C. on thermoshaker for 60 min.

| 100 mM MgCl$_2$ | 30 µl |
| 50 × PI (protease inhibitor) | 10 µl |
| Chromatin in Shearing buffer | 60 µl |
| Indexed bidirectional Tn5 transposome | 20 µl |
| H$_2$O | 180 µl |

60 µL 6× ChIP buffer (see Materials) was added into the sample to quench index-tagmentation, and transferred into a 1.5 ml EP tube. Antibody-coated beads were added to the sample and allowed for ChIP 2 hr.

Beads were washed with $1^{st}$ washing buffer twice, then washed with $2^{nd}$ washing buffer twice. Beads were then resuspended with $3^{rd}$ washing buffer, then beads were transferred to PCR tube.

The beads were washed with 1×NEBuffer 1.0, then freshly prepared Exo III digestion solution was added as below. Digestion was pursued at 37° C. for 20 min, the Exo III was deactivated along with reverse crosslinking at 95° C. for 60 min.

| 10 × NEBuffer 1.0 | 2 µl |
| EXO III | 0.5 µl |
| H$_2$O | 17.5 µl |

Digested DNA was then transferred into a new PCR tube, and was set up for self-ligation (self-circularization) reaction as below. Self-ligation was carried out at 60° C. for 1 hour, then the CircLigase was deactivated by heating at 80° C. for 20 min.

| Reverse crosslinked ssDNA | 20 µl |
| 1 mM ATP | 1.25 µl |
| 50 mM MnCl$_2$ | 1.25 µl |
| CircLigase | 1 µl |
| 0.5M Tris 8.0 | 1.5 µl |

1 µl USER enzyme was then added to the circularized ssDNA, and incubated at 37° C. for 15 min.

DNA was cleaned up with 60 µl Agencourt AMPure XP beads following the manual. Beads capturing DNA were resuspended with 18 µl H$_2$O, and 16 µl of supernatant was transferred into a new PCR tube to set up the below reaction.

| | | | |
|---|---|---|---|
| NEBNext Q5 Hot Start HiFi Master Mix | | | 20 µl |
| DNA (beads purified) | | | 16 µl |
| Primer SMITHP5 | | | 2 µl |
| Primer SMITHP7.1 | | | 2 µl |

PCR program was set up as below:

| | | | |
|---|---|---|---|
| Step 1 | 98° C. | 30 s | |
| Step 2 | 98° C. | 10 s | |
| Step 3 | 65° C. | 75 s | back to Step 2 for 15-18 cycles |
| Step 4 | 65° C. | 5 min | |
| Step 5 | 4° C. | hold | |

Amplified DNA (library) was cleaned up with 60 µl Agencourt AMPure XP beads following manual. Library was size selected with AMPure beads according to Agencourt Manual. Library size was checked with Bioanalyzer. The DNA library was then subjected to next-generation sequencing on HiSeq 2500 platform using sequencing primers SMITHSeqP1 and SMITHSeqP2.

As can be seen from FIG. 9, ChIP-SMITH method and the bidirectional transposon compositions described herein provided a similar ChIP-seq effect to regular ChIP, or index-tagmented ChIP using the modified design of Nextera® Tn5 dual-transposon. However, ChIP-SMITH method employing the bidirectional transposon compositions described herein only used 5% of the starting Ciona materials as compared to regular ChIP, and 50% of the starting Ciona materials as compared to index-tagmented ChIP using the modified design of Tn5 dual-transposon. Furthermore, ChIP-SMITH method was completed within 2 days, while a week was spent for regular ChIP-seq protocol, and 3-4 days were spend with index-tagmented ChIP using the modified design of Tn5 dual-transposon. These results showed that ChIP-SMITH method and the bidirectional transposon end composition described in provided a much efficient and effective method for genomic studies.

SEQUENCE LISTING (transferred transposon end nucleic acid sequence)
SEQ ID NO: 1
AGATGTGTATAAGAGACAG (non-transferred transposon end nucleic acid sequence; 5'-phosphate is not shown when used as an oligo for assembling transposon end composition)
SEQ ID NO: 2
CTGTCTCTTATACACATCT (amplification tag nucleic acid sequence)
SEQ ID NO: 3
GACGCTGCCGACGA (amplification facilitating tag nucleic acid sequence)
SEQ ID NO: 4
CTCGG

TABLE 1

Exemplary transposon end composition transferred strand nucleic acid sequences

| SEQ ID NO: | Oligo # | Sequence |
|---|---|---|
| 5 | SMITH50.X | NNNNNNnnnnnGACGCTGCCGACGAU*CTCGG*AGATGTGTATAAGAGACAG |
| 6 | SMITH50.1 | ATGTCAnnnnnGACGCTGCCGACGAU*CTCGG*AGATGTGTATAAGAGACAG |
| 7 | SMITH50.2 | AGACGTnnnnnGACGCTGCCGACGAU*CTCGG*AGATGTGTATAAGAGACAG |
| 8 | SMITH50.3 | TCAGTAnnnnnGACGCTGCCGACGAU*CTCGG*AGATGTGTATAAGAGACAG |
| 9 | SMITH50.4 | TATCATnnnnnGACGCTGCCGACGAU*CTCGG*AGATGTGTATAAGAGACAG |
| 10 | SMITH50.5 | GACGTCnnnnnGACGCTGCCGACGAU*CTCGG*AGATGTGTATAAGAGACAG |
| 11 | SMITH50.6 | GCACGCnnnnnGACGCTGCCGACGAU*CTCGG*AGATGTGTATAAGAGACAG |
| 12 | SMITH50.7 | CAGTAGnnnnnGACGCTGCCGACGAU*CTCGG*AGATGTGTATAAGAGACAG |
| 13 | SMITH50.8 | CGTCTGnnnnnGACGCTGCCGACGAU*CTCGG*AGATGTGTATAAGAGACAG |

(Sample index tag is underlined; amplification facilitating tag is italicized; transferred transposon end nucleic acid is shaded; restriction site deoxyUridine (U) is bolded; N or n can be any nucleic acid; 5'-phosphate is not shown)

TABLE 2

Exemplary PCR primer nucleic acid sequences

| SEQ ID NO: | PCR primer # | Sequence |
|---|---|---|
| 14 | SMITHP5 | AATGATACGGCGACCACCGAGATCTACACTCGTCGGCAGCGTC |
| 15 | SMITHP7.X | CAAGCAGAAGACGGCATACGAGAT<u>NNNNNN</u>GGCG*CTCGG*AGATGTGTATAAGAGACAG |
| 16 | SMITHP7.1 | CAAGCAGAAGACGGCATACGAGAT<u>CGTGAT</u>GGCG*CTCGG*AGATGTGTATAAGAGACAG |
| 17 | SMITHP7.2 | CAAGCAGAAGACGGCATACGAGAT<u>ACATCG</u>GGCG*CTCGG*AGATGTGTATAAGAGACAG |
| 18 | SMITHP7.3 | CAAGCAGAAGACGGCATACGAGAT<u>GCCAAT</u>GGCG*CTCGG*AGATGTGTATAAGAGACAG |
| 19 | SMITHP7.4 | CAAGCAGAAGACGGCATACGAGAT<u>GATCAG</u>GGCG*CTCGG*AGATGTGTATAAGAGACAG |
| 20 | SMITHP7.5 | CAAGCAGAAGACGGCATACGAGAT<u>CAGATC</u>GGCG*CTCGG*AGATGTGTATAAGAGACAG |

(Sequencing barcode/experimental index is underlined; sequence identical to amplification facilitating tag is italicized; sequence identical to transferred transposon end nucleic acid is shaded; sequence reverse-complimentary to amplification tag is bolded; N can be any nucleic acid)

TABLE 3

Exemplary sequencing primer nucleic acid sequences

| SEQ ID NO: | Sequencing primer # | Sequence |
|---|---|---|
| 21 | SMITHSeqP1 | GAGATCTACACTCGTCGGCAGCGTC |
| 22 | SMITHSeqP2 | <u>CTGTCTCTTATACACATCT</u>*CCGAG*CGCC |
| 23 | SMITHSeqP3 (optional for paired end sequencing) | GGCG*CTCGG*AGATGTGTATAAGAGACAG |

(sequence reverse-complimentary to transferred transposon end nucleic acid is underlined; sequence reverse-complimentary to amplification tag is bolded; sequence reverse-complimentary to amplification facilitating tag is italicized; sequence identical to transferred transposon end nucleic acid is shaded; sequence identical to amplification facilitating tag is italicized)

(sample index tag or experimental index nucleic acid sequence; N can be any nucleic acid)
SEQ ID NO: 24
NNNNNN (sample index tag nucleic acid sequence)
SEQ ID NO: 25
ATGTCA (sample index tag nucleic acid sequence)
SEQ ID NO: 26
AGACGT (sample index tag nucleic acid sequence)
SEQ ID NO: 27
TCAGTA (sample index tag nucleic acid sequence)
SEQ ID NO: 28
TATCAT (sample index tag nucleic acid sequence)
SEQ ID NO: 29
GACGTC (sample index tag nucleic acid sequence)
SEQ ID NO: 30
GCACGC (sample index tag nucleic acid sequence)
SEQ ID NO: 31
CAGTAG (sample index tag nucleic acid sequence)
SEQ ID NO: 32
CGTCTG (experimental index tag nucleic acid sequence)
SEQ ID NO: 33
CGTGAT (experimental index tag nucleic acid sequence)
SEQ ID NO: 34
ACATCG (experimental index tag nucleic acid sequence)
SEQ ID NO: 35
GCCAAT (experimental index tag nucleic acid sequence)
SEQ ID NO: 36
GATCAG (experimental index tag nucleic acid sequence)
SEQ ID NO: 37
CAGATC (UMI tag nucleic acid sequence; N can be any nucleic acid)
SEQ ID NO: 38
NNNNN

TABLE 4

Exemplary nucleic acid sequences for making modified dual-transposon design
(Sample barcode is underlined, N or n can be any nucleic acid)

| SEQ ID NO: | Oligo # | Sequence |
|---|---|---|
| 39 | Tn5-A.N | CGTGTGCTCTTCCGATCTNNNNTCGTCGGCAGCGTCAGATGTGTATAAGAGACAG |
| 40 | Tn5-A.1 | CGTGTGCTCTTCCGATCTATCGTCGTCGGCAGCGTCAGATGTGTATAAGAGACAG |
| 41 | Tn5-A.2 | CGTGTGCTCTTCCGATCTTGACTCGTCGGCAGCGTCAGATGTGTATAAGAGACAG |
| 42 | Tn5-B.n | CGACGCTCTTCCGATCTnnnnGTCTCGTGGGCTCGGAGATGTGTATAAGAGACAG |
| 43 | Tn5-B.1 | CGACGCTCTTCCGATCTCTAGGTCTCGTGGGCTCGGAGATGTGTATAAGAGACAG |
| 44 | Tn5-B.2 | CGACGCTCTTCCGATCTGCATGTCTCGTGGGCTCGGAGATGTGTATAAGAGACAG |

(sample barcode nucleic acid sequence of modified dual-transposon design; N can be any nucleic acid)
SEQ ID NO: 45

NNNN (deoxyUridine sequence as restriction site tag)
SEQ ID NO: 46

U (amplification facilitating tag & transferred transposon end)
SEQ ID NO: 47

CTCGGAGATGTGTATAAGAGACAG (sequence reverse complimentary to SEQ ID NO: 15; N can be any nucleic acid)
SEQ ID NO: 48

CTGTCTCTTATACACATCTCCGAGCGCCNNNNNNNATCTCGTATGCCGTCT
TCTGCTTG (sequence reverse complimentary to SEQ ID NO: 14)
SEQ ID NO: 49

GACGCTGCCGACGAGTGTAGATCTCGGTGGTCGCCGTATCATT

What is claimed is:

1. A method of analyzing the binding sequences on a chromatin comprising chromatin protein and chromatin DNA to which a protein of interest binds, comprising:
   (a) randomly inserting a plurality of transposon end compositions into the chromatin in the presence of a transposase; wherein the transposon end composition comprises from 5' to 3': an amplification tag, a restriction site tag, and a transposon end; thereby generating fragmented chromatin tagged with at least one transposon end composition through the transposon end to chromatin DNA ("chromatin DNA tagged with transposon end");
   (b) subjecting fragmented chromatin tagged with at least one transposon end composition to immunoprecipitation using an antibody specifically recognizing the protein of interest;
   (c) denaturing chromatin DNA from immunoprecipitated fragmented chromatin tagged with at least one transposon end composition from step (b), thereby generating single-strand immunoprecipitated chromatin DNA tagged with transposon end;
   (d) self-circularizing the single-strand immunoprecipitated chromatin DNA tagged with transposon end from step (c);
   (e) linearizing the self-circularized single-strand immunoprecipitated chromatin DNA tagged with transposon end from step (d) by generating a breakage at the restriction site tag; and
   (f) analyzing the linearized single-strand immunoprecipitated chromatin DNA tagged with transposon end from step (e), thereby determining the binding sequences to which the protein of interest binds.

2. The method of claim 1, wherein the chromatin in step (a) is cross-linked with a reversible cross-linking agent.

3. The method of claim 2, wherein the reversible cross-linking agent is formaldehyde.

4. The method of claim 1, wherein the chromatin in step (a) is pre-fragmented before transposon end composition insertion.

5. The method of claim 1, wherein the transposase is Tn5.

6. The method of claim 1, wherein the restriction site tag is deoxyUridine (U).

7. The method of claim 1, wherein the transposon end composition further comprises at the 5' end of the transposon end one or more of a sample index tag, a unique molecular identifier tag, and an amplification facilitating tag.

8. The method of claim 7, wherein the transposon end composition comprises, from 5' to 3': a sample index tag, an unique molecular identifier tag, an amplification tag, a restriction site tag, an amplification facilitating tag, and a transposon end.

9. The method of claim 7, wherein the transposon end composition further comprises a sample index tag at the 5' end of the transposon end, and wherein step (b) further comprises pooling at least two chromatin samples inserted with transposon end compositions comprising different sample index tags.

10. The method of claim 1, wherein step (f) comprises sequencing the linearized single-strand immunoprecipitated chromatin DNA tagged with transposon end.

11. The method of claim 1, wherein step (c) further comprises removing the protein of interest and chromatin protein from chromatin DNA.

12. The method of claim 1, wherein step (b) further comprises digesting from 3'-hydroxyl termini of chromatin DNA from immunoprecipitated fragmented chromatin tagged with at least one transposon end composition until the digestion is blocked by the protein of interest or chromatin protein.

13. The method of claim 12, wherein the digestion is carried out by a 3'→5' exonuclease.

14. The method of claim 1, wherein the self-circularization is carried out by a single-strand DNA (ssDNA) ligase.

15. The method of claim 1, wherein step (f) comprises amplifying the linearized single-strand immunoprecipitated chromatin DNA tagged with transposon end with a first PCR primer capable of hybridizing to the amplification tag, and a second PCR primer comprising a sequence identical to that of the transposon end.

16. A method of sequencing a nucleic acid sequence on a chromosome comprising chromatin, comprising:
   (a) randomly inserting a plurality of transposon end compositions into the chromatin in the presence of a transposase, wherein the transposon end composition comprises from 5' to 3': an amplification tag, a restriction site tag, and a transposon end; thereby generating fragmented chromatin tagged with at least one transposon end composition through the transposon end to chromatin DNA ("chromatin DNA tagged with transposon end");
   (b) denaturing chromatin DNA tagged with transposon end from step (a), thereby generating single-strand chromatin DNA tagged with transposon end;
   (c) self-circularizing single-strand chromatin DNA tagged with transposon end from step (b);
   (d) linearizing the self-circularized single-strand chromatin DNA tagged with transposon end from step (c) by generating a breakage at the restriction site tag; and
   (e) determining the nucleic acid sequence of the linearized single-strand chromatin DNA tagged with transposon end.

17. The method of claim 16, wherein step (b) further comprises removing chromatin protein from chromatin DNA.

18. The method of claim 16, wherein the self-circularization is carried out by an ssDNA ligase.

19. The method of claim 16, wherein the transposon end composition further comprises a sample index tag at the 5' end of the transposon end, and wherein step (b) further comprises pooling at least two chromatin samples inserted with transposon end compositions comprising different sample index tags.

20. A transposon end composition comprising, from 5' to 3': an amplification tag, a restriction site tag which is deoxyUridine (U), and a transposon end.

* * * * *